(12) United States Patent
Suki et al.

(10) Patent No.: US 12,078,578 B2
(45) Date of Patent: Sep. 3, 2024

(54) SYSTEM AND METHOD FOR DETERMINING A PHYSIOLOGICAL CONDITION OF BIOLOGICAL TISSUE

(71) Applicants: Trustees of Boston University, Boston, MA (US); Beth Israel Deaconess Medical Center, Inc., Boston, MA (US)

(72) Inventors: Bela Suki, Newton, MA (US); Jae Hun Kim, Natick, MA (US); Joseph Hall, Boston, MA (US); Ramaswamy Krishnan, Boston, MA (US); Niccole Schaible, Boston, MA (US)

(73) Assignees: Trustees of Boston University, Boston (MA), Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 18/211,046

(22) Filed: Jun. 16, 2023

(65) Prior Publication Data
US 2023/0408376 A1    Dec. 21, 2023

Related U.S. Application Data

(60) Provisional application No. 63/352,667, filed on Jun. 16, 2022.

(51) Int. Cl.
*G01N 1/06*   (2006.01)
*G01N 1/31*   (2006.01)
(Continued)

(52) U.S. Cl.
CPC .............. *G01N 1/06* (2013.01); *G01N 1/312* (2013.01); *G01N 3/08* (2013.01); *G01N 35/00009* (2013.01); *G01N 2035/00019* (2013.01)

(58) Field of Classification Search
CPC ............ G01N 1/06; G01N 1/312; G01N 3/08; G01N 35/00009; G01N 2035/00019;
(Continued)

(56) References Cited

U.S. PATENT DOCUMENTS

| 6,783,503 B1 * | 8/2004 | Duda ................. G01N 3/40 600/587 |
| 11,360,010 B1 | 6/2022 | Neu et al. |

(Continued)

FOREIGN PATENT DOCUMENTS

CN        112996438 A        6/2021

OTHER PUBLICATIONS

Imsirovic et al. "Design of a novel equi-biaxial stretcher for live cellular and subcellular imaging." PLoS One 10(10): e0140283 pp. 1-14 (2015).

(Continued)

*Primary Examiner* — Brandi N Hopkins
(74) *Attorney, Agent, or Firm* — NIXON PEABODY LLP; Ronald I. Eisenstein; Jeanne N. Jodoin

(57) ABSTRACT

Provided herein are systems for determining a stretch condition of a tissue and assessing the stiffness of the tissue. Also provided herein are methods for using the systems for measuring stiffness of a tissue, assessing the effect of an agent on a tissue, and identifying subjects having a disease or disorder associated with increased or decreased stiffness of a tissue.

20 Claims, 62 Drawing Sheets
(5 of 62 Drawing Sheet(s) Filed in Color)

(51) Int. Cl.
*G01N 3/08* (2006.01)
*G01N 3/42* (2006.01)
*G01N 35/00* (2006.01)

(58) Field of Classification Search
CPC ........... G01N 11/10; G01N 2021/6441; G01N 33/564; G01N 33/4833; G01N 3/24; G01N 33/6893; G01N 15/1056; G01N 33/4905; G01N 33/5302; G01N 33/54326; C12Q 1/6883; A61B 5/442; G01Q 10/045
See application file for complete search history.

(56) References Cited

U.S. PATENT DOCUMENTS

2012/0186365 A1* 7/2012 Beyeler ................ G01Q 30/025
73/862.541
2012/0271555 A1* 10/2012 Levental .................. G01N 3/42
702/19
2018/0002667 A1 1/2018 Keskar et al.

OTHER PUBLICATIONS

Mondonedo et al. "A high-throughput system for cyclic stretching of precision-cut lung slices during acute cigarette smoke extract exposure." Frontiers in Physiology 11: 566 pp. 1-10 (2020).
Ram-Mohan et al. "Tissue traction microscopy to quantify muscle contraction within precision-cut lung slices." American Journal of Physiology-Lung Cellular and Molecular Physiology 318(2): L323-L330 (2020).

* cited by examiner

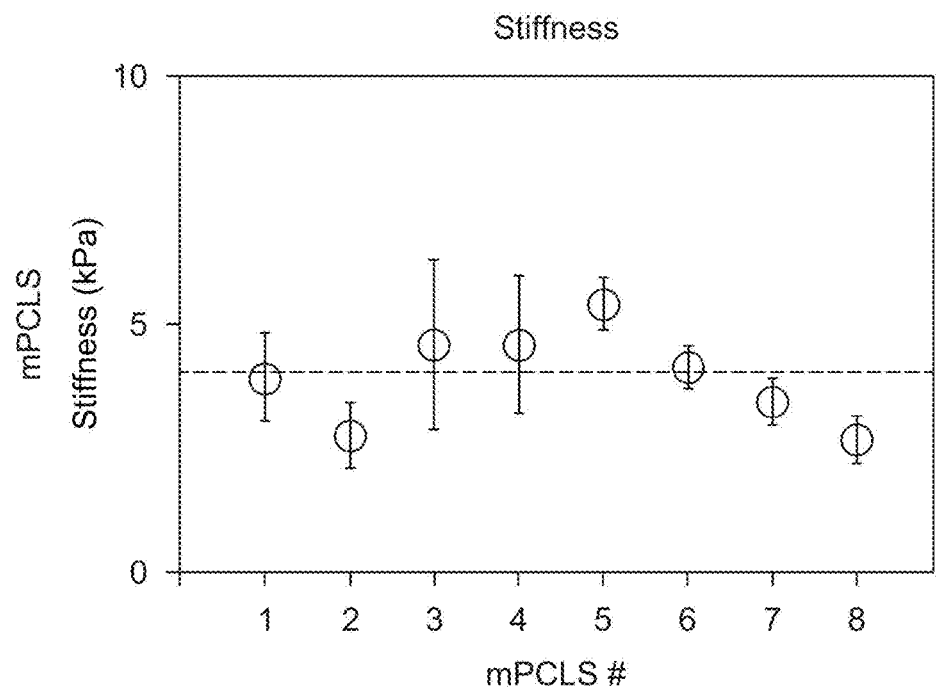
FIG. 18A
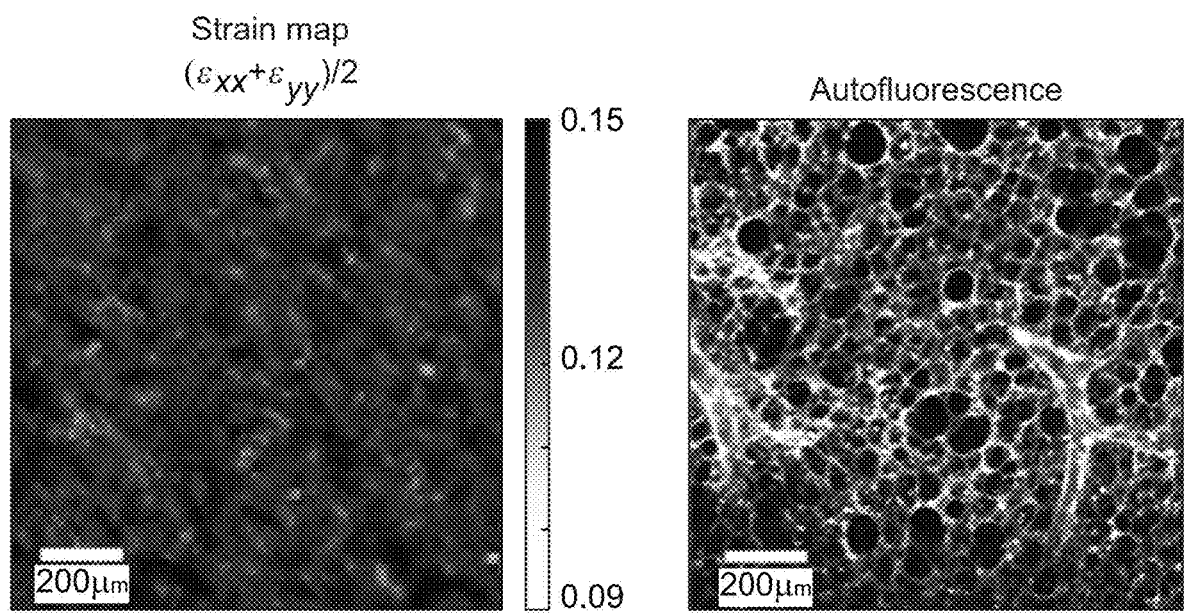
FIG. 18B
FIG. 18C

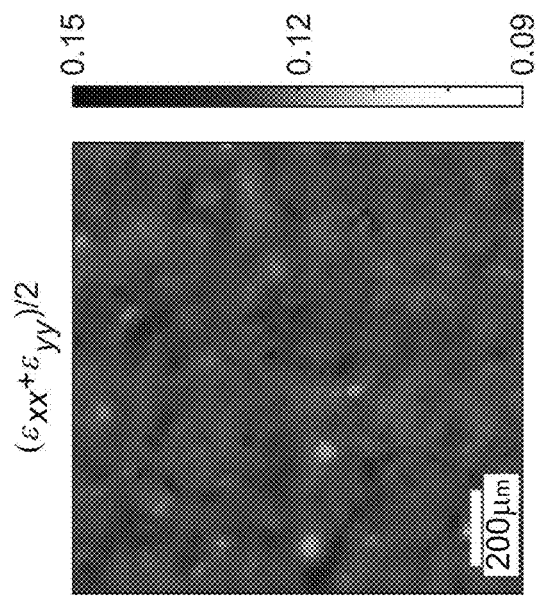
FIG. 23
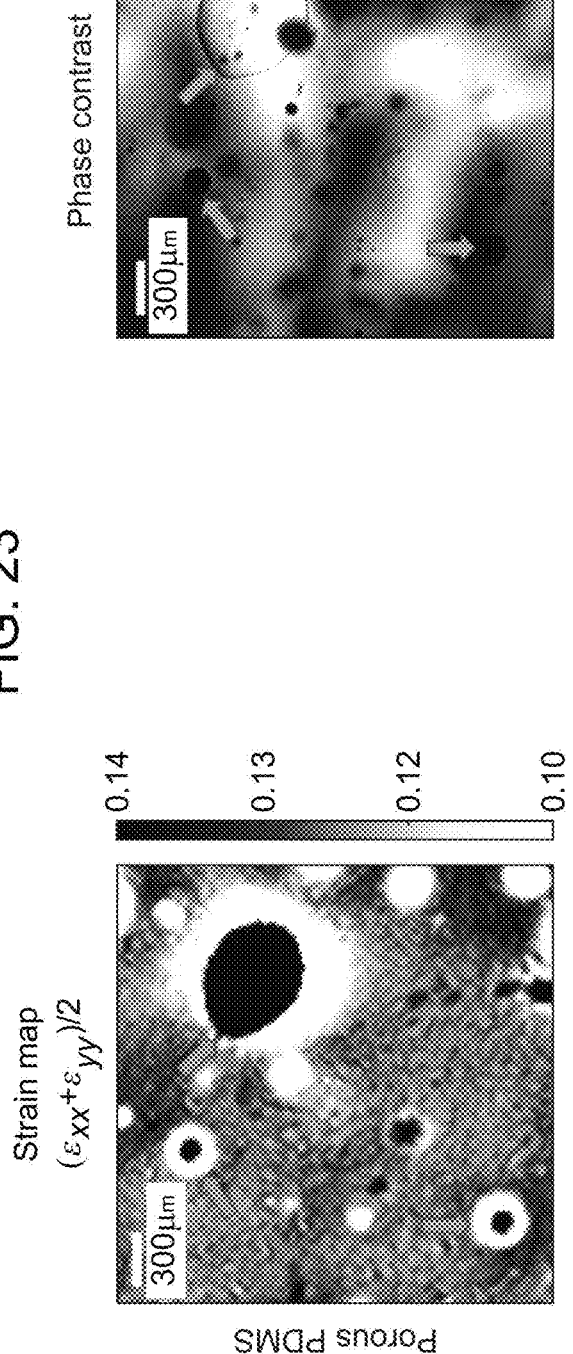
FIG. 24B
FIG. 24A

|  | Porous | | Non-Porous | |
|---|---|---|---|---|
|  | sample # | stiffness (kPa) | sample # | stiffness (kPa) |
| Current device | 1 | 2.75 | 1 | 3.35 |
|  | 2 | 2.57 | 2 | 3.2 |
|  | Mean±SD | 2.66±0.13 | Mean±SD | 3.28±0.11 |
| Uniaxial stretcher | 1 | 2.6 | 1 | 3.03 |
|  | 2 | 2.65 | 2 | 3.07 |
|  | Mean±SD | 2.63±0.04 | Mean±SD | 3.05±0.03 |

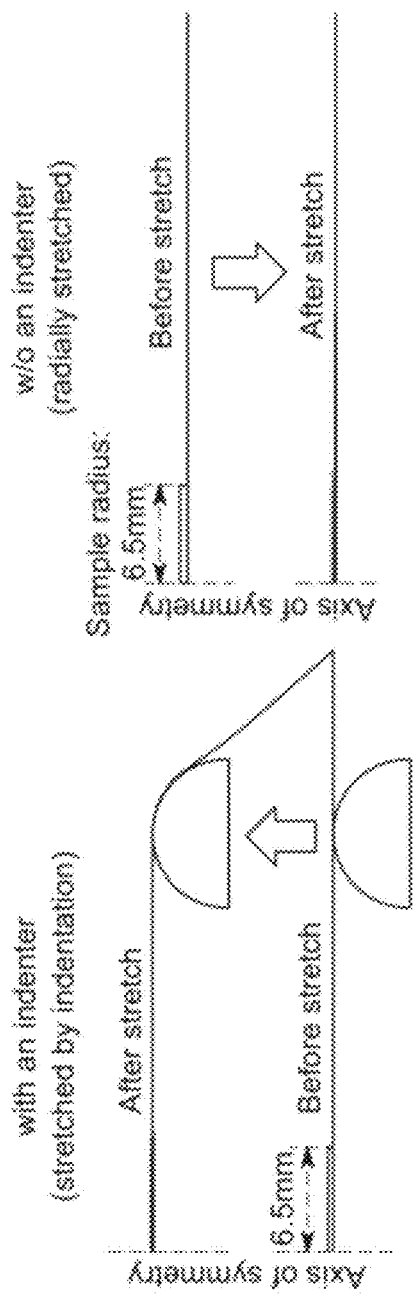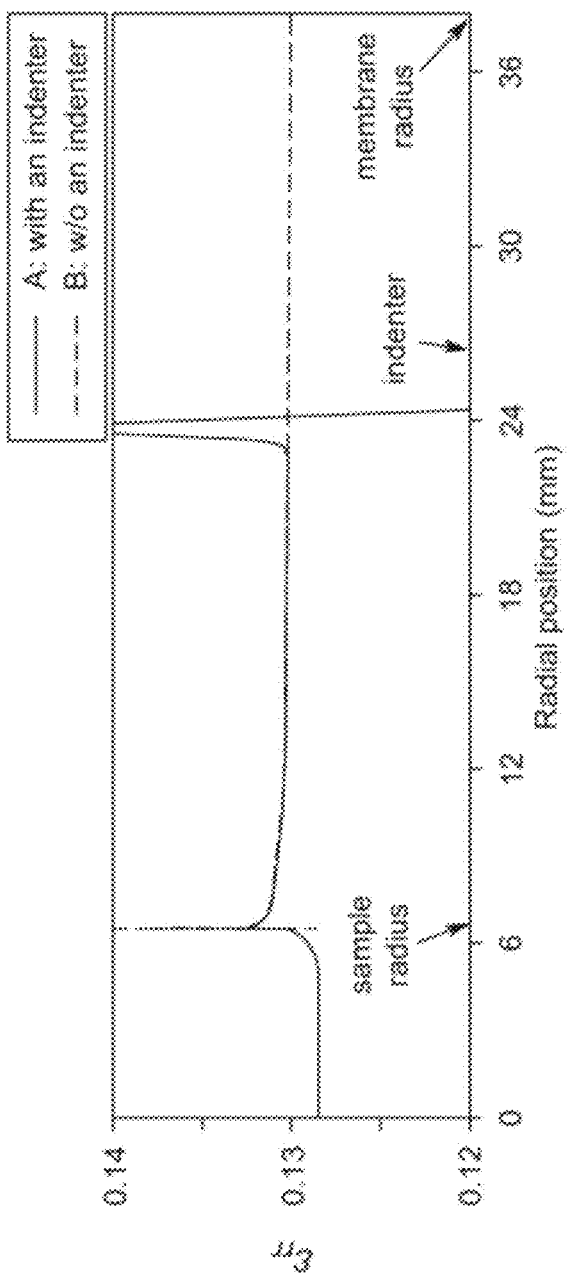
FIG. 26A
FIG. 26B
FIG. 26C

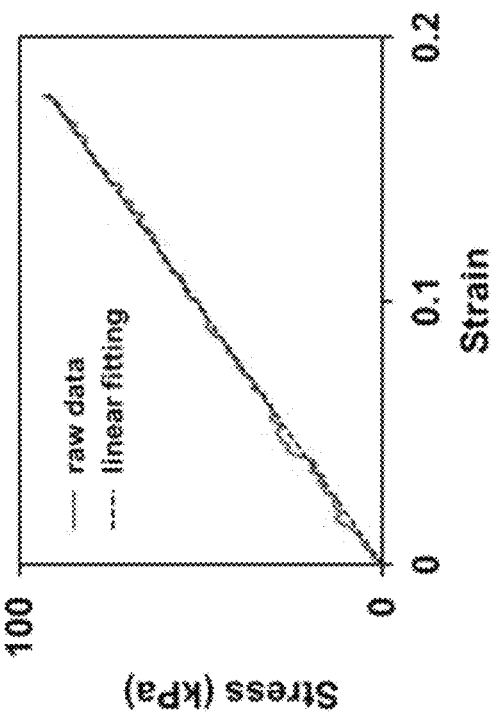
FIG. 29A
FIG. 29B
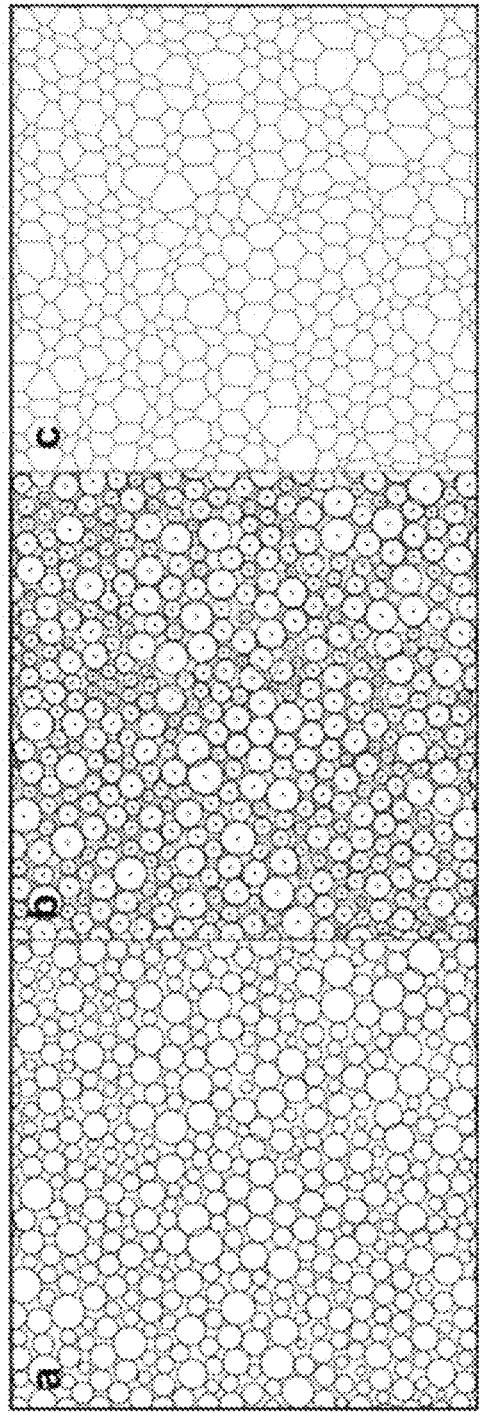
FIG. 30A   FIG. 30B   FIG. 30C

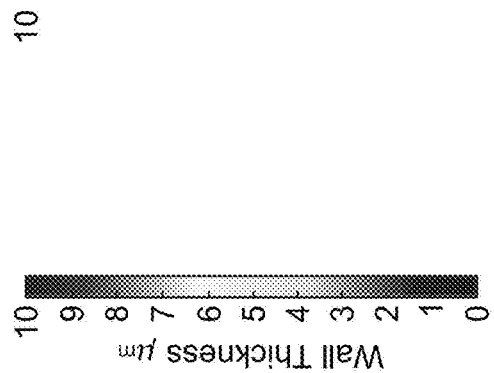
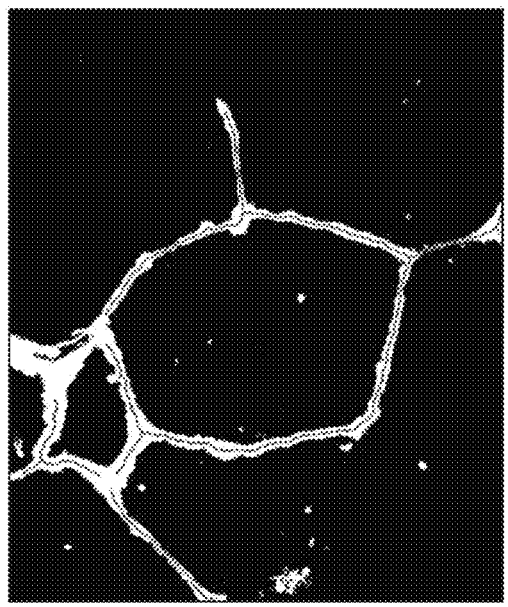
FIG. 32B
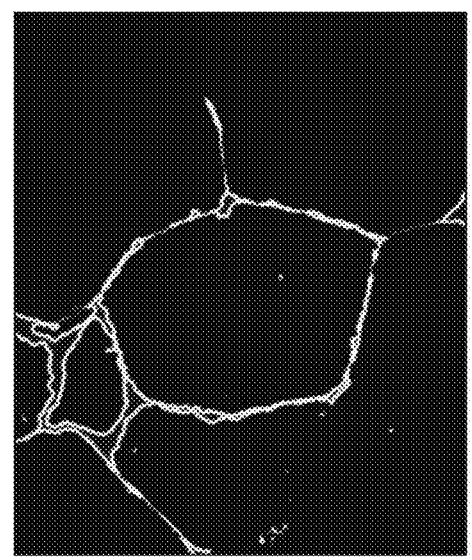
FIG. 32C
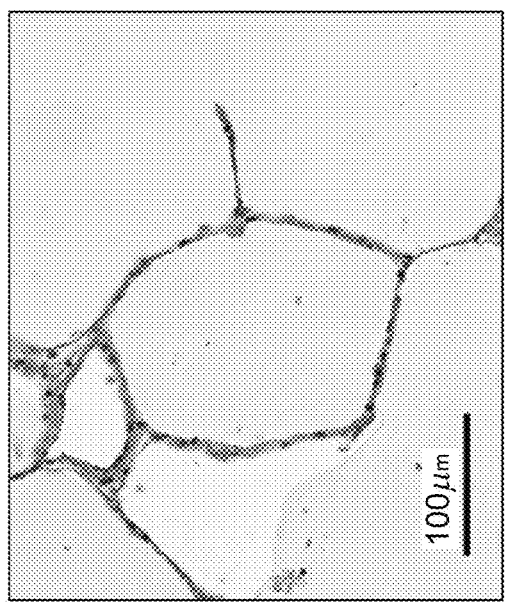
FIG. 32A

| Coordinate | Enzyme |
|---|---|
| A1,2 | Reference spots |
| A3,4 | ADAM8 |
| A5,6 | ADAM9 |
| A7,8 | ADAMTS1 |
| A9,10 | ADAMTS13 |
| A11,12 | Cathepsin A |
| A13,14 | Cathepsin B |
| A15,16 | Cathepsin C |
| A17,18 | Cathepsin D |
| A19,20 | Reference spots |
| B3,4 | Cathepsin E |
| B5,6 | Cathepsin L |
| B7,8 | Cathepsin S |
| B9,10 | Cathepsin V |
| B11,12 | Cathepsin X/Z/P |
| B13,14 | CD26 |
| B15,16 | Kallikrein 3 |
| B17,18 | Kallikrein 5 |
| C3,4 | Kallikrein 6 |
| C5,6 | Kallikrein 7 |
| C7,8 | Kallikrein 10 |
| C9,10 | Kallikrein 11 |
| C11,12 | Kallikrein 13 |

| Coordinate | Enzyme |
|---|---|
| C13,14 | MMP-1 |
| C15,16 | MMP-2 |
| C17,18 | MMP-3 |
| D3,4 | MMP-7 |
| D5,6 | MMP-8 |
| D7,8 | MMP-9 |
| D9,10 | MMP-10 |
| D11,12 | MMP-12 |
| D13,14 | MMP-13 |
| D15,16 | Neprilysin |
| D17,18 | Presenilin |
| E1,2 | Reference spots |
| E3,4 | Proprotein convertase 9 |
| E5,6 | Proteinase 3 |
| E7,8 | Urokinase |
| E9,10 | Negative control |

FIG. 35B

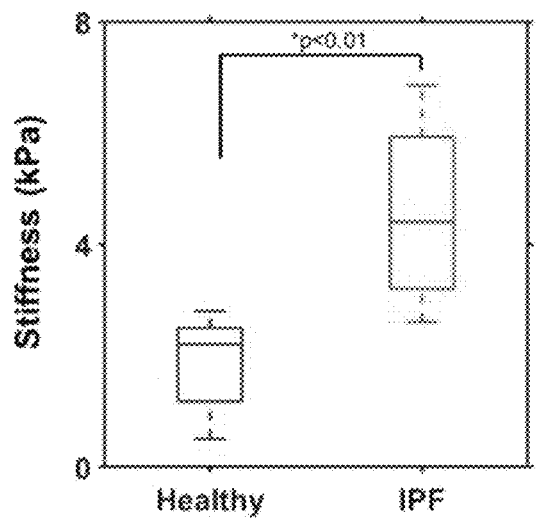
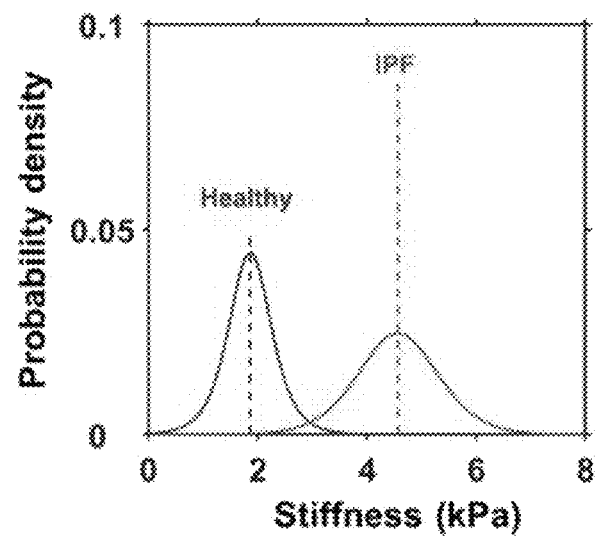
FIG. 39A  FIG. 39B
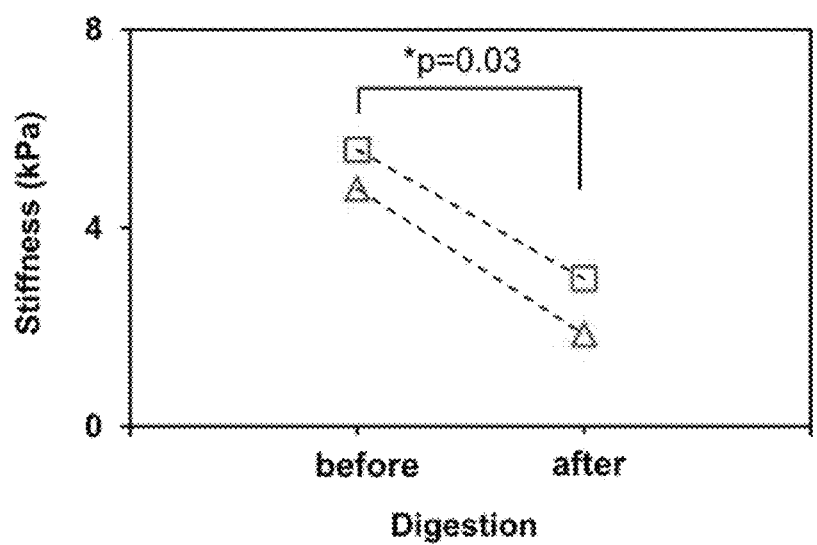
FIG. 40

SYSTEM AND METHOD FOR DETERMINING A PHYSIOLOGICAL CONDITION OF BIOLOGICAL TISSUE

CROSS-REFERENCE TO RELATED APPLICATIONS

This application claims the benefit of, and priority to, U.S. Provisional Patent Application No. 63/352,667, filed Jun. 16, 2022, which is hereby incorporated by reference herein in its entirety.

GOVERNMENT SUPPORT

This invention was made with government support under Grant Numbers OD024993; HL147673; HL139466 and AI151695, awarded by the National Institutes of Health. The Government has certain rights in the invention.

FIELD OF THE INVENTION

The present invention relates generally to determining biological properties, and more specifically, to measuring stiffness of a biological tissue sample.

BACKGROUND OF THE INVENTION

Overall, many potential drugs have been found via current high-throughput assays, but the majority of new molecular entities approved by the US food and drug administration (FDA) continue to be discovered via traditional phenotypic assays. Moreover, because 50% of drug candidates currently fail in phase II clinical trials, it has been suggested that decreased failure rates and reduced development costs might be attained if disease-relevant endpoints were brought into drug discovery at an earlier stage. To fill this gap, the present inventors have developed novel measurements of multiscale tissue stiffness, which serves as the targeted physiological endpoint.

Pulmonary fibrosis and emphysema, a common component of chronic obstructive pulmonary disease (COPD), for example, are debilitating diseases that remodel the lung leading to increased and reduced tissue stiffness, respectively. Thus, understanding disease progression requires assessing lung stiffness at both the tissue and alveolar scales. Here, the inventors introduce an approach to determine multiscale tissue stiffness and apply it to precision-cut lung slices (PCLS). First, the inventors established a framework for measuring stiffness of thin, disk-like samples. The inventors then designed a device to verify this concept and validated its measuring capabilities using samples of known stiffness. Next, the inventors measured the stiffness of fibrotic and emphysematous human PCLS, and found that the former was approximately twice as stiff whereas latter was 50% softer than healthy human PCLS. Through computational network modeling, the inventors discovered that the reduced macroscopic tissue stiffness of emphysematous PCLS was due to both microscopic septal wall remodeling and structural deterioration. Finally, through protein expression profiling, the inventors identified a wide spectrum of enzymes that can drive septal wall remodeling, which together with mechanical forces, lead to rupture and structural deterioration of the emphysematous lung parenchyma.

Accordingly, described herein is a novel, improved system, and methods thereof for measuring stiffness of a sample, for example, a biological or non-biological sample. Moreover, the system described herein is widely adaptable to facilitate drug discovery and drug repurposing in any circumstance in which modulation of tissue stiffness is a logical therapeutic target, including but not limited to pulmonary diseases, including COPD, pulmonary fibrosis, asthma, pneumonia, and viral infections such as COVID-19, and cancer, and other diseases, including cardiovascular diseases, orthopedic diseases and diseases in kidney, bladder, liver or muscles.

SUMMARY OF THE INVENTION

The term embodiment and like terms, e.g., implementation, configuration, aspect, example, and option, are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter. This summary is also not intended to be used in isolation to determine the scope of the claimed subject matter. The subject matter should be understood by reference to appropriate portions of the entire specification of this disclosure, any or all drawings, and each claim.

According to certain aspects of the present disclosure, a system is directed to determining a stretch condition of a biological tissue, the system including a free-standing composite layer configured to receive a tissue sample of the biological tissue. The free-standing composite layer has a first surface, a second surface that is opposing to the first surface, and two opposing ends. The free-standing composite layer includes a flexible membrane extending between the two opposing ends, a plurality of fiduciary markers interspersed with the flexible membrane, and an adhesive area extending at least a portion of the first surface. The adhesive area is configured to receive with a no-slip interface the tissue sample. The system further includes a stretching device that includes an indenter having a plurality of inner points configured to contact the second surface of the free-standing composite layer. The stretching device further includes a rim aligned with the indenter along a central axis, the rim having a plurality of outer points configured to contact the first surface near the two opposing ends of the free-standing composite layer. The plurality of outer points are farther from the central axis than the plurality of inner points. At least one of the indenters and the rim is movable to cause a uniform equibiaxial mechanical stretch of the free-standing composite layer and the tissue sample.

According to other aspects of the present disclosure, a system is directed to determining a stretch condition of a biological tissue. The system includes a free-standing composite layer configured to receive a tissue sample of the biological tissue. The free-standing composite layer has a first surface, a second surface that is opposing to the first surface, and two opposing ends. The free-standing composite layer includes a first layer in the form of a flexible membrane that forms a base of the free-standing composite layer. The free-standing composite layer further includes a second layer with a tunable stiffness overlaying in a no-slip interface with the first layer, the second layer including a plurality of fiduciary markers, The free-standing composite layer further includes a third layer overlaying in a no-slip interface with the second layer, the third layer having an adhesive surface opposing the no-slip interface with the second layer. The adhesive surface is configured to receive with a no-slip interface the tissue sample. The system further includes a stretching device with an indenter having a plurality of inner points configured to contact the second surface of the free-standing composite layer. The stretching device further has a rim aligned with the indenter along a central axis, the rim having a plurality of outer points configured to contact the first surface near the two opposing ends of the free-standing composite layer. The plurality of outer points are farther from the central axis than the plurality of inner points. At least one of the indenter and the rim is movable to cause an uniform equibiaxial mechanical stretch of the free-standing composite layer and the tissue sample.

A method of classifying a sample, the method comprising determining a global radial strain of a substrate layer that is measured when the layer is stretched without a sample using any of the systems described herein; adhering the sample to the to a freestanding composite layer; and applying radial stretch the freestanding composite layer having an adhered sample and determining a global radial strain of the substrate layer that is measured when the layer is stretched, wherein measuring is done via a formula of:

$$\varepsilon_{rr}^{o} = \Delta r_{memb}/r_{memb}^{o} \times 100$$

wherein $\Delta r_{memb}$ denotes the change of the radius, and $r_{memb}^{o}$ is the stress-free radius, and the local radial strain $\varepsilon_{rr}$ that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^{0} - \varepsilon_{rr}}{\varepsilon_{rr}^{0} h} = AE$$

wherein h is the thickness of the sample, A is a constant that is computed through a linear regression, and E is the stiffness of a sample, and wherein samples are classified as either having increased stiffness, decreased stiffness, or normal parameters.

A method of assessing the effect of at least one agent on classification of a sample, the method comprising determining a global radial strain of a substrate layer that is measured when the layer is stretched without a sample using any of the systems described herein; adhering the sample to the to a freestanding composite layer; contacting the sample with the at least one agent; and applying radial stretch the freestanding composite layer having an adhered sample and determining a global radial strain of the substrate layer that is measured when the layer is stretched, wherein measuring is done via a formula of:

$$\varepsilon_{rr}^{o} = \Delta r_{memb}/r_{memb}^{o} \times 100$$

wherein $\Delta r_{memb}$ denotes the change of the radius, and $r_{memb}^{o}$ is the stress-free radius, and the local radial strain E rr that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^{0} - \varepsilon_{rr}}{\varepsilon_{rr}^{0} h} = AE$$

wherein h is the thickness of the sample, A is a constant that is computed through a linear regression, and E is the stiffness of a sample, and wherein samples are classified as either having increased stiffness, decreased stiffness, or normal parameters.

A method of assessing the effect of at least one agent on the classification of a sample, the method comprising: calculating a first stiffness of the sample; contacting the sample with at least one agent; calculating a second stiffness of the sample, wherein samples are classified as either having increased stiffness, decreased stiffness, or normal parameters.

A method of identifying a subject as having a disease or disorder associated with increased or decreased stiffness of a tissue, the method comprising: obtaining a sample from a subject; calculating a stiffness of the sample; comparing the stiffness the sample to a stiffness of an appropriate control sample; and identifying the subject as having a disease or disorder with increased stiffness of a tissue if the stiffness of the sample is greater than the stiffness of the appropriate control sample, or identifying the subject as having a disease or disorder with increased stiffness of a tissue if the stiffness of the sample obtained from a subject is greater than the stiffness of the appropriate control sample.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims. Additional aspects of the disclosure will be apparent to those of ordinary skill in the art in view of the detailed description of various embodiments, which is made with reference to the drawings, a brief description of which is provided below.

Definitions

As used herein, "assessing the effect" refers to comparing a characteristic (i.e., stiffness) of a sample that has been contacted by an agent to said characteristic of a sample thereof that has not been contacted by an agent. For example, the stiffness of a sample that has been contacted by an agent is assessed and compared to an identical sample that has not been contacted by an agent. A change in stiffness between these populations is the measured response. In one embodiment, stiffness of a tissue that has been contacted by an agent is compared to a non-identical sample that has not been contacted by an agent. In one embodiment, stiffness of a sample that has been contacted by an agent is compared to the stiffness of the sample prior to contact with an agent or at various time points while being contacted by an agent. For example, the stiffness of the sample can be assessed prior to being contacted by an agent, 12 hours after contact by an agent, and 24 hours after contacted by an agent. The stiffness at these three time points would be compared.

As used herein, the term "contacting" when used in reference to a sample (e.g., a cell population or tissue) encompasses both introducing or administering an agent, surface, hormone, etc. to the cell, tissue, or organ in a manner that permits physical contact of the cell with the agent, surface, hormone etc., and introducing an element, such as a genetic construct or vector, that permits the expression of an agent, such as a miRNA, polypeptide, or other expression product in the cell. It should be understood that a cell genetically modified to express an agent, is "contacted" with the agent, as are the cell's progeny that express the agent.

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., an autoimmune or cancer. A subject can be male or female.

A subject can be one who has been previously diagnosed with or identified as suffering from or having a disease or disorder in need of treatment or one or more complications related to such a disease or disorder, and optionally, have already undergone treatment for the disease or disorder or the one or more complications related to the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

As used herein, an "agent" refers to e.g., a molecule, protein, peptide, antibody, or nucleic acid, that inhibits expression of a polypeptide or polynucleotide, or binds to, partially or totally blocks stimulation, decreases, prevents, delays activation, inactivates, desensitizes, or down regulates the activity of the polypeptide or the polynucleotide. Agents that inhibit a gene, e.g., inhibit expression, e.g., translation, post-translational processing, stability, degradation, or nuclear or cytoplasmic localization of a polypeptide, or transcription, post transcriptional processing, stability or degradation of a polynucleotide or bind to, partially or totally block stimulation, DNA binding, transcription factor activity or enzymatic activity, decrease, prevent, delay activation, inactivate, desensitize, or down regulate the activity of a polypeptide or polynucleotide. An agent can act directly or indirectly.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

The term "decrease", "reduced", "reduction", or "inhibit" are all used herein to mean a decrease by a statistically significant amount. In some embodiments, "decrease", "reduced", "reduction", or "inhibit" typically means a decrease by at least 10% as compared to an appropriate control and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to an appropriate control.

The terms "increase", "enhance", or "activate" are all used herein to mean an increase by a reproducible statistically significant amount. In some embodiments, the terms "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, a 20 fold increase, a 30 fold increase, a 40 fold increase, a 50 fold increase, a 6 fold increase, a fold increase, a 100 fold increase, etc. or any increase between 2-fold and 10-fold or greater as compared to an appropriate control. In the context of a marker, an "increase" is a reproducible statistically significant increase in such level.

As used herein, the term "alters" refers to an effect including increasing or decreasing a given parameter as those terms are defined herein.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with an autoimmune disease, or a biological sample that has not been contacted with an agent disclosed herein).

As used herein, an "appropriate control" refers to an untreated, otherwise identical cell or population (e.g., a patient who was not administered an agent described herein, or was administered by only a subset of agents described herein, as compared to a non-control cell).

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

BRIEF DESCRIPTION OF THE DRAWINGS

This patent or application file contains at least one drawing executed in color. Copies of this patent or patent application publication with color drawings will be provided by the Office upon request and payment of the necessary fee.

The disclosure, and its advantages and drawings, will be better understood from the following description of representative embodiments together with reference to the accompanying drawings. These drawings depict only representative embodiments, and are therefore not to be considered as limitations on the scope of the various embodiments or claims.

(FIG. 17A) Axisymmetric finite element (FE) model simulates stretching of a sample of 6.5 mm radius attached to a membrane of 38 mm radius. Color codes depict the radial normal strain, $\varepsilon_{rr}$. Inset: zoomed in view of strain. (FIG. 17B) $\varepsilon_{rr}$ versus radial position measured at the interface between the bottom of the sample and the membrane with varying sample stiffnesses. Black solid line represents the global strain without a sample, $\varepsilon_{rr}^{\circ}$. (FIG. 17C) The difference of strains ($\varepsilon_{rr}^{\circ}-\varepsilon_{rr}$) normalized with $\varepsilon_{rr}^{\circ}$ and sample thickness h increases with increasing sample stiffness. Black dotted line depicts a linear regression across all simulations. (FIG. 17D) A histogram plot of strain components, $\varepsilon_{xx}$ and $\varepsilon_{yy}$, computed from each pixel in the FIG. 3B. Dotted lines depict averages of all pixels. Numbers indicate average strains and standard errors of $\varepsilon_{xx}$ and $\varepsilon_{yy}$. (FIG. 17E) Stiffness of agarose samples measured using the current device (Red). Dashed line, green and purple markers indicate the stiffnesses previously measured using the unconfined compression (13) and AFM (14,15), respectively.

FIGS. 18A-18L shows stiffness and correlation maps of mouse and human PCLS. (FIG. 18A) Stiffness of mPCLS is between 2 and 6 kPa (magenta markers). Dotted line indicates the median of all mPCLS (3.91 kPa). (FIG. 18B), (FIG. 18E) and (FIG. 18H) are color coded maps of average strain, $(\varepsilon_{xx}+\varepsilon_{yy})/2$, measured in a mPCLS, a healthy hPCLS, and an emphysematous hPCLS, respectively. (FIG. 18C), (FIG. 18F) and (FIG. 18I) are autofluorescent images (from a different field of view) acquired from an mPCLS, a healthy hPCLS, and an emphysematous hPCLS, respectively. (FIG. 18D) Stiffness of a healthy PCLS ranges between 1 and 7 kPa (blue). Dotted line indicates the median (2.28 kPa).

(FIG. 18G) Stiffness of an emphysematous PCLS is between 0.1 and 2 kPa. Dotted line indicates the median (0.96 kPa). (FIG. 18J) Bayesian estimation of the posterior distribution of stiffness of healthy and emphysematous hPCLS. Inset: box plot comparing stiffness of healthy and emphysematous hPCLS shown in FIG. 18D and FIG. 18G. *The stiffness of emphysematous hPCLS is significantly lower than that of the healthy hPCLS (one-tailed t-test, p=0.026, one-tailed Bayesian factor: 2.54). Boxplot shows medians and quartiles. Whiskers are maximum and minimum values. (FIG. 18K) Autocorrelation of strains acquired from mPCLS, healthy hPCLS, and emphysematous hPCLS group. A total of 6-8 strain maps were analyzed for each group. (FIG. 18L) Autocorrelation of autofluorescence tissue images acquired from mPCLS, healthy hPCLS, and emphysematous hPCLS group. 16 images obtained from 4 tissues were used in each group. Error bars indicate standard errors. On FIG. 18K and FIG. 18L, the dotted lines indicate $C(\rho)=0.5$ and the tables show $\rho$ values at which $C(\rho)=0.5$.

(FIG. 19A) An example of color-coded alveolar airspaces identified from autofluorescent images taken from an hPCLS sample. (FIG. 19B) Comparison of the probability distributions of alveolar areas obtained from images similar to that in FIG. 19A. The blue and red symbols denote measured distributions and the corresponding solid lines are lognormal fits to the data obtained from healthy and emphysematous hPCLSs, respectively. (FIG. 19C) Spring network representations of hPCLS in 2D. Left shows a network of healthy hPCLS and the right demonstrates airspace enlargement in an emphysematous hPCLS. The insets zoom into the square regions of each network. (FIG. 19D) Variation of strain energy with strain in ten network pairs with area distributions pooled from the lognormal fits in panel B. Blue and red curves correspond to networks representing healthy and emphysematous hPCLS, respectively. (FIG. 19E) Posterior distributions of the alveolar septal wall stiffness parameter for the networks representing healthy (blue) and emphysematous (red) hPCLS. Inset: comparison of the means by t-test (p=0.08) and Bayesian analysis (Bayesian factor: 1.65).

(FIG. 20A) Raw protein array images from the healthy (top) and emphysematous (bottom) hPCLSs. The darkness and size of the dots determine the relative quantities detected. Each enzyme is detected in duplicates. The red numbers refer to enzymes in FIG. 20C. (FIG. 20B) Logarithm of the expression in arbitrary units of 27 enzymes included in the protein array. Those enzymes that had no detectable levels in both the healthy and emphysematous hPCLSs are not included. CATS denotes cathepsin. Notice that 3 enzymes, Kallikrein 13, MMP-10 and Urokinase were not detectable in the healthy hPCLS. (FIG. 20C) Ratio of expressions of enzyme levels in the emphysematous and healthy hPCLSs for a subset of enzymes. Only those enzymes are included for which the level in emphysematous tissue is at least 1.5 times that in the healthy tissue. The numbers in front of the enzymes refer to the locations shown in red on panel a (bottom). The number above the bars are the actual ratios. Note that Kallikrein 13, MMP-10 and Urokinase are not included in the panel.

(FIG. 21A) Radial strain $\varepsilon_{rr}$ (purple) and hoop strain $\varepsilon_{\theta\theta}$ (dark red) versus radial position measured at the interface between the sample and the membrane. $E_{rr}=\varepsilon_{\theta\theta}$ and both strains are nearly constant within the sample region. Black solid line depicts strains from the case without a sample, $\varepsilon_{rr}^{\circ}$ and $\varepsilon_{\theta\theta}^{\circ}$. (FIG. 21B) $\varepsilon_{\theta\theta}$ with varying sample stiffness (colored lines).

(FIG. 22A) $\varepsilon_{rr}$ versus radial position with sample thickness varying from 100 to 700 μm (colored lines). Regardless of sample thickness, E rr is nearly constant within the sample area up to −3 mm of radial position. Black solid line depicts strains from the case without a sample, $\varepsilon_{rr}^{\circ}$. (FIG. 22B) The normalized strains do not change with $\varepsilon_{rr}^{\circ}$ varying from 0.09 to 0.14.

FIG. 23 shows example strain map of a 1.5% agarose sample. A color-coded map of average strain $(\varepsilon_{xx}+\varepsilon_{yy})/2$, measured in a 1.5% agarose sample. A global stretch of approximately 13.9% was applied.

FIGS. 24A-24C show stiffness of porous and non-porous PDMS samples. (FIG. 24A) A color-coded map of the average strain, $(\varepsilon_{xx}+\varepsilon_{yy})/2$, measured in a porous PDMS sample. (FIG. 24B) A phase contrast image corresponding to (FIG. 24A). Arrows depict pores trapped within the sample. (FIG. 24C) Stiffness values of porous and non-porous PDMS samples. Porous PDMS samples were 14% and 18% softer than non-porous samples, as determined by the current device and by a well-established uniaxial stretcher device (see Methods), respectively). Two porous and two non-porous samples were used.

FIG. 25 shows Bayesian estimation of the distribution of stiffness variance of normal and emphysematous hPCLS. The dashed lines show the mode of the distributions.

FIGS. 26A-26C show far beyond the sample region, the strain profiles from finite element models with and without a hollow indenter are nearly identical. (FIG. 26A) A FE model with a hollow indenter. A membrane is equi-biaxially stretched by displacement of the hollow indenter. (FIG. 26B) FE model without a hollow indenter. A membrane is radially stretched. (FIG. 26C) Radial strain E rr measured at the interface between the sample and the membrane. Blue and red depict strains measured from the models in (FIG. 26A) and (FIG. 26B), respectively. The strain profiles from the two different models are nearly identical far beyond the sample region up to −20 mm of radial position.

(FIG. 27A) 3D model with a circular sample aligned at the center of a membrane. (FIG. 27D) 3D model with an elliptical sample aligned at the center of a membrane. (FIG. 27H) 3D model with a circular sample aligned at 2 mm off from the center of a membrane. The origin of XY-axes is at the center of a sample. (FIG. 27B), (FIG. 27E) and (FIG. 27H) are strains measured along the X axis at the interface between the sample and the membrane. (FIG. 27C), (FIG. 27F) and (FIG. 27I) are strains measured along the Y axis. The measured average strain $(\varepsilon_{xx}+\varepsilon_{yy})/2$ is the same (0.128) in all 3 cases of (FIG. 27A), (FIG. 27D) and (FIG. 27G).

FIGS. 29A and 29B show stiffness of the membrane composite. (FIG. 29A) A representative stress-strain curve measured in the uniaxial stretch device. (FIG. 29B) Summary of measurements.

FIGS. 30A-30C show creation of polygonal network from densely-packed input circles. (FIG. 30A) Densely-packed 'input circles' with areas matching an input distribution, (FIG. 30B) modified Voronoi Diagram to convert circles into a polygonal network, and (FIG. 30C) resulting polygonal network, with each edge modeled as a spring that represents an alveolar septal wall.

(FIG. 31A) and (FIG. 31C) Area distributions from the emphysematous fluorescent images compared to the area distributions from the healthy network shown in (FIG. 31B) and the emphysematous network shown in (FIG. 31D).

FIGS. 32A-32D show example of wall thickness measurement. (FIG. 32A) Original histological image, (FIG. 32B) Binarized image with centerline shown in red, with non-wall regions manually removed, (FIG. 32C) Heat map of distance from edge of tissue, and (FIG. 32D) PDF of wall thicknesses for given image, taken along red centerline.

(FIG. 33A) Manual tracing of alveolar areas from histological images (FIG. 33B) Bayesian estimation of the posterior distribution of shrinkage caused by fixation, (FIG. 33C) and (FIG. 33E) Probability distributions of Emphysematous Alveolar areas from fluorescent and histological images, pre and post correction with Bayesian scaling, respectively, (FIG. 33D) and (FIG. 33F) Probability distributions of healthy alveolar areas from fluorescent and histological images, pre and post correction with Bayesian scaling, respectively.

FIGS. 35A and 35B show description of protein array. Blots with coordinates (FIG. 35A) and description of enzymes corresponding to the coordinates (FIG. 35B).

(FIG. 36A) Blots with coordinates corresponding to various enzymes listed in Supplementary Figure S15. (FIG. 36B) and (FIG. 36C) Vertically integrated intensity profiles in rectangular boxes along lanes A, B, C, D, and E for healthy and emphysematous hPCLSs, respectively.

(FIG. 37A) and (FIG. 37B) show H&E-stained images from the healthy and the emphysematous donors, respectively, at high magnification. Arrows denote fibroblasts (yellow), alveolar epithelial type II cells (blue), macrophages (purple) and blood cells such as lymphocytes (black). The red arrows point to locations of rupture.

(FIG. 38A) A phase contrast image of a mPCLS obtained on an inverted widefield scope (Olympus, ix83). (FIG. 38B), (FIG. 38D) Zoomed images of phase contrast and fluorescence channels obtained at the same position, depicting the parenchymal structure (FIG. 38B) and beads (FIG. 38D), respectively. (FIG. 38C), (FIG. 38E) Strain maps computed from phase contrast (FIG. 38C) and fluorescence (FIG. 38E) images, respectively. The average in-plane strains computed from structure (13.31%) and beads (13.33%) were identical. The stiffness of the mPCLS was determined to be 3.1 kPa.

FIG. 39A-39B shows stiffness of healthy and IPF hPCLS. IPF hPCLS (red) are approximately twice stiff as healthy (blue) PCLS (one-tailed t test, p<0.01) (FIG. 38A). Boxplot shows medians and quartiles. Whiskers are maximum and minimum values. Bayesian estimation of the posterior distribution of stiffness showed little overlap between them with a one-sided Bayesian factor of 6.72 (FIG. 38B).

FIG. 40 shows stiffness of healthy mPCLS before (blue) and after digestion (red), respectively. Square and triangle markers depict each of mPCLS before and after digestion. Stiffness of healthy mPCLS was reduced to approximately a half after digestion (one-tailed t test, p=0.03).

DETAILED DESCRIPTION

Figure 1:
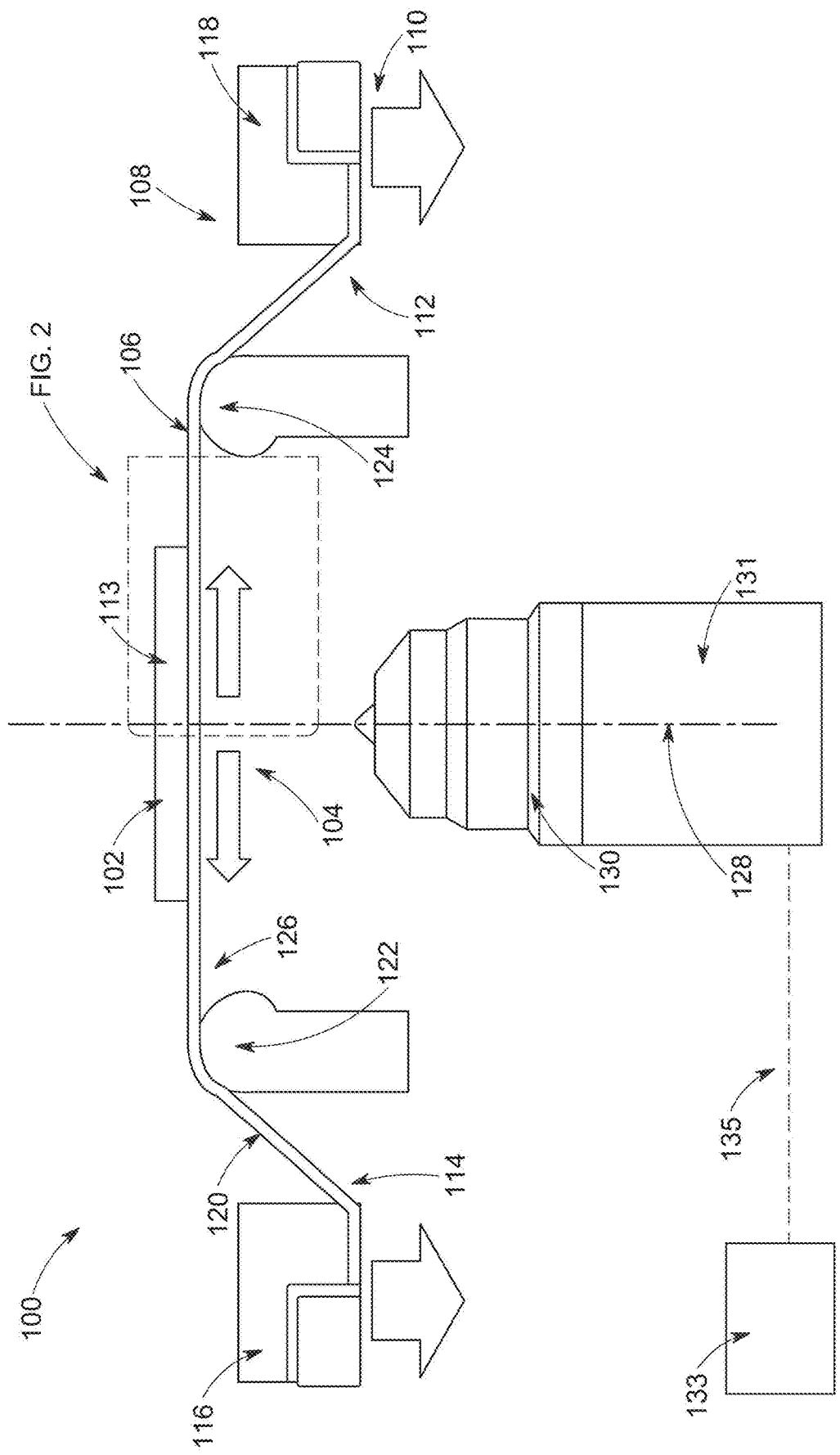
FIG. 1 is an illustrative view of a system for determining a stretch condition for a tissue sample, according to one exemplary embodiment.

Various embodiments are described with reference to the attached figures, where like reference numerals are used throughout the figures to designate similar or equivalent elements. The figures are not necessarily drawn to scale and are provided merely to illustrate aspects and features of the present disclosure. Numerous specific details, relationships, and methods are set forth to provide a full understanding of certain aspects and features of the present disclosure, although one having ordinary skill in the relevant art will recognize that these aspects and features can be practiced without one or more of the specific details, with other relationships, or with other methods. In some instances, well-known structures or operations are not shown in detail for illustrative purposes. The various embodiments disclosed herein are not necessarily limited by the illustrated ordering of acts or events, as some acts may occur in different orders and/or concurrently with other acts or events. Furthermore, not all illustrated acts or events are necessarily required to implement certain aspects and features of the present disclosure.

For purposes of the present detailed description, unless specifically disclaimed, and where appropriate, the singular includes the plural and vice versa. The word "including" means "including without limitation." Moreover, words of approximation, such as "about," "almost," "substantially," "approximately," and the like, can be used herein to mean "at," "near," "nearly at," "within 3-5% of," "within acceptable manufacturing tolerances of," or any logical combination thereof. Similarly, terms "vertical" or "horizontal" are intended to additionally include "within 3-5% of" a vertical or horizontal orientation, respectively. Additionally, words of direction, such as "top," "bottom," "left," "right," "above," and "below" are intended to relate to the equivalent direction as depicted in a reference illustration; as understood contextually from the object(s) or element(s) being referenced, such as from a commonly used position for the object(s) or element(s); or as otherwise described herein.

Referring to FIG. 1, a system 100 is directed generally to determining a stretch condition for a tissue sample 102. According to one example, the system 100 applies an equibiaxial mechanical stretch 104 to a free-standing composite layer 106 that holds the tissue sample 102. The tissue sample 102, according to some examples, has a tissue-like size and shape. The system 100 includes a stretching device 108 that includes a rim 110 for holding the free-standing composite layer 106 in place at two opposing ends 112, 114, while an indenter 112 applies the equibiaxial mechanical stretch 104 to a central area 113 of the free-standing composite layer 106.

More specifically, the rim 110 has a plurality of outer points 116, 118 that are configured to contact a first surface 120 of the free-standing composite layer 106. The outer points 116, 118 contact the first surface 120 near the two opposing ends 112, 114 of the free-standing composite layer 106.

The indenter 112 has a plurality of inner points 122, 124 configured to contact a second surface 126 of the free-standing composite layer 106. The inner points 122, 124 contact the second surface 126 near the central area 113 of the free-standing composite layer 106.

The rim 110 and the indenter 112 are generally aligned along a central axis 128, along which an imaging path allows capturing images of the tissue sample 102 using a microscope objective 130. The outer points 116, 118 are farther from the central axis 128 than the inner points 122, 124.

The microscope objective 130 is part of a microscope 131 that is communicatively coupled with a controller 133, which is configured for processing images captured via the microscope 131. The microscope 131 is optionally an inverted microscope.

A communication protocol 135 between the microscope 131 and the controller 133 is a wired or wireless protocol. The controller 133 is optionally integrated within a computer, a server, a mobile device, or any other computing device having a computing processor. As disclosed in more detail below, the controller is configured to determine a global radial strain of the free-standing composite layer that is measured when the layer is stretched without a sample via a formula of:

$$\varepsilon_{rr}^{o} = \Delta r_{memb} / r_{memb}^{o} \times 100$$

wherein $\Delta r_{memb}$ denotes the change of the radius, and $r_{memb}^{o}$ is the stress-free radius, and the local radial strain $E_{rr}$ that is measured when the composite layer and a tissue sample 102 adhered to that layer is stretched. The difference between the global radial strain and the local strain is converted to a readout of the stiffness of the sample through a formula that is derived by the inventors as described below, wherein samples are classified as either having increased stiffness, decreased stiffness, or normal parameters.

Figure 2:
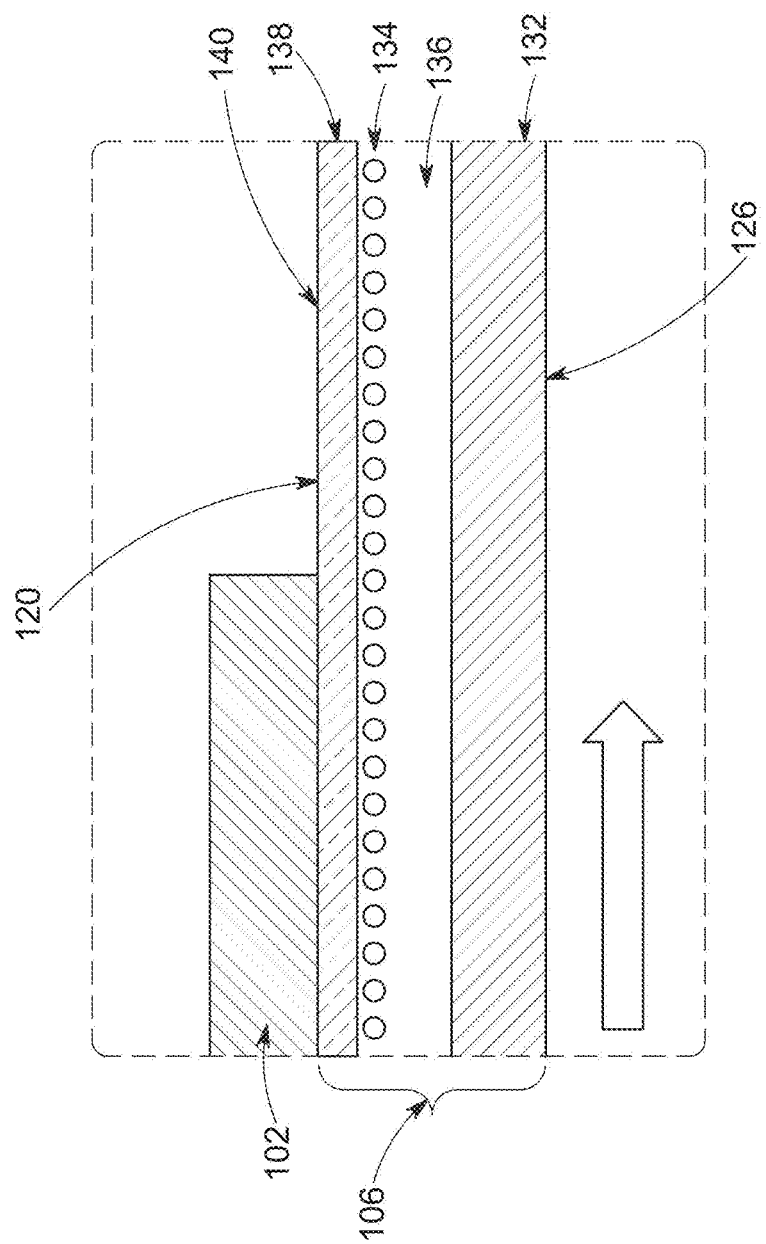
FIG. 2 is an enlarged view illustrating a free-standing composite layer with the tissue sample of FIG. 1.

Referring to FIG. 2, the free-standing composite layer 106 includes a flexible membrane 132 that extends between the two opposing ends 112, 114 (shown in FIG. 1). The flexible membrane 132, according to one exemplary embodiment, is a first layer that forms a base of the free-standing composite layer 106. The flexible membrane 132 optionally includes one or more of a silicon material and a polydimethylsiloxane (PDMS) material.

According to another exemplary embodiment, the flexible membrane 132 is the only layer of the free-standing composite layer 106. In other words, the free-standing composite layer consists of a single layer in the form of the flexible membrane 132. For ease of understanding, the flexible membrane 132 is further referred to below as the first layer 132 when referring to an embodiment in which the free-standing composite layer 106 includes more than one layer.

The free-standing composite layer 106 further includes a plurality of fiduciary markers 134 that are interspersed to facilitate mapping a spatial distribution of displacements and strains underneath the tissue sample 102. In one exemplary embodiment (which is not illustrated), the fiduciary markers 134 are interspersed with the flexible membrane 132. In other exemplary embodiments, the fiduciary markers 134 are interspersed with other portions or layers of the free-standing composite layer 106 (as disclosed below).

According to alternative embodiments, the fiduciary markers 134 are interspersed on or within the respective layer or layers of the free-standing composite layer 106. In other words, the fiduciary markers 134 can be located below a surface of the free-standing composite layer 106 or on top of the surface, such as the first surface 120.

According to some embodiments, at least one of the fiduciary markers 134 is in the form of a fluorescent bead. Optionally, the fiduciary markers 134 consist of fluorescent beads of different colors.

The free-standing composite layer 106 further includes, optionally, a second layer 136 that overlays in a no-slip interface with the first layer 132. Optionally, as illustrated in FIG. 2, the fiduciary markers 134 are interspersed with the second layer 136. The second layer 136 optionally consists of a PDMS material.

The free-standing composite layer 106 further includes, optionally, a third layer 138 overlaying in a no-slip interface with the second layer 136. The third layer 138 has an adhesive surface 140 opposing the no-slip interface with the second layer 136. The adhesive surface 140 is configured to receive with a no-slip interface the tissue sample 102. The third layer 138 optionally consists of a PDMS material (i.e., it is a sticky PDMS layer).

In some embodiments the adhesive surface 140 is the same as at least a portion of the first surface 120 of the free-standing composite layer 106. Thus, the adhesive surface 140 extends its "sticky" properties to portions of or the entirety of the first surface 120. In accordance with alternative embodiments in which the free-standing composite layer 106 includes only the flexible membrane 132 as the only (first) layer 132, the adhesive surface 120 is integrated along at least a portion of the flexible membrane 132.

Figure 3:
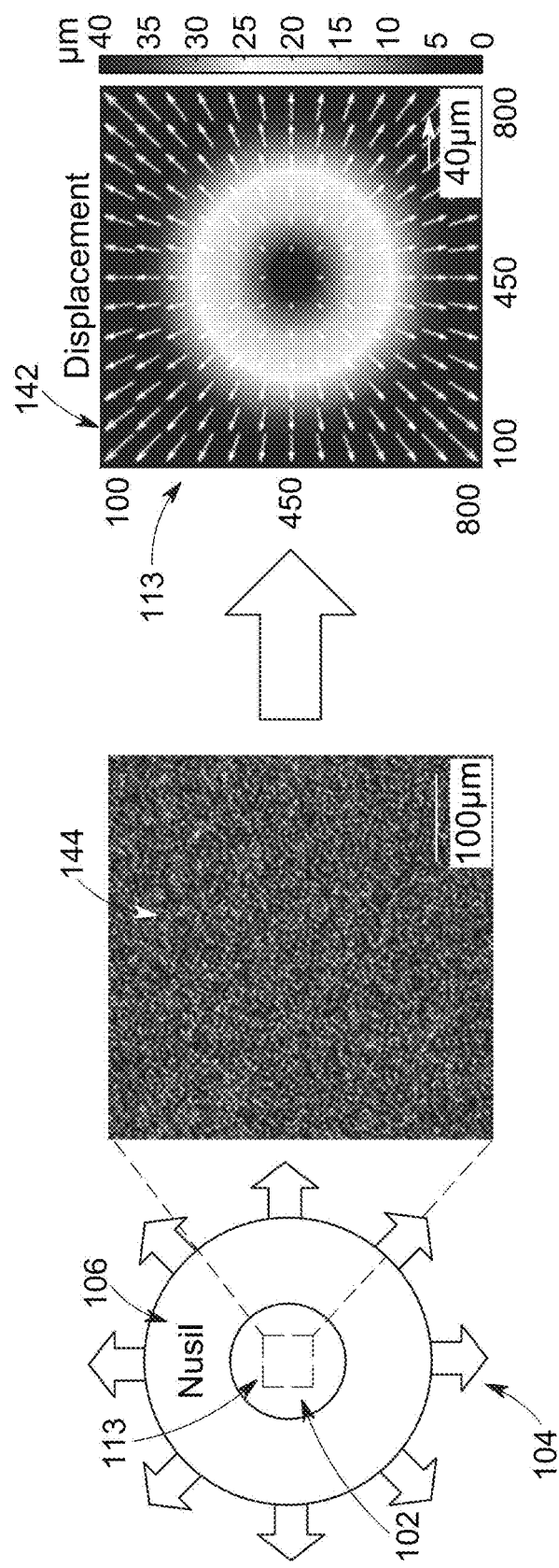
FIG. 3A is an illustrative view of the free-standing composite layer and the tissue sample of FIG. 2 being subjected to an uniform equibiaxial mechanical stretch.
FIG. 3B is an image of the free-standing composite layer of FIG. 3A with fluorescent beads embedded on a surface of a gel membrane.
FIG. 3C is a map of bead displacements overlaid with vectors near a center area of the free-standing composite layer and tissue sample of FIG. 3A.
Figure 4:
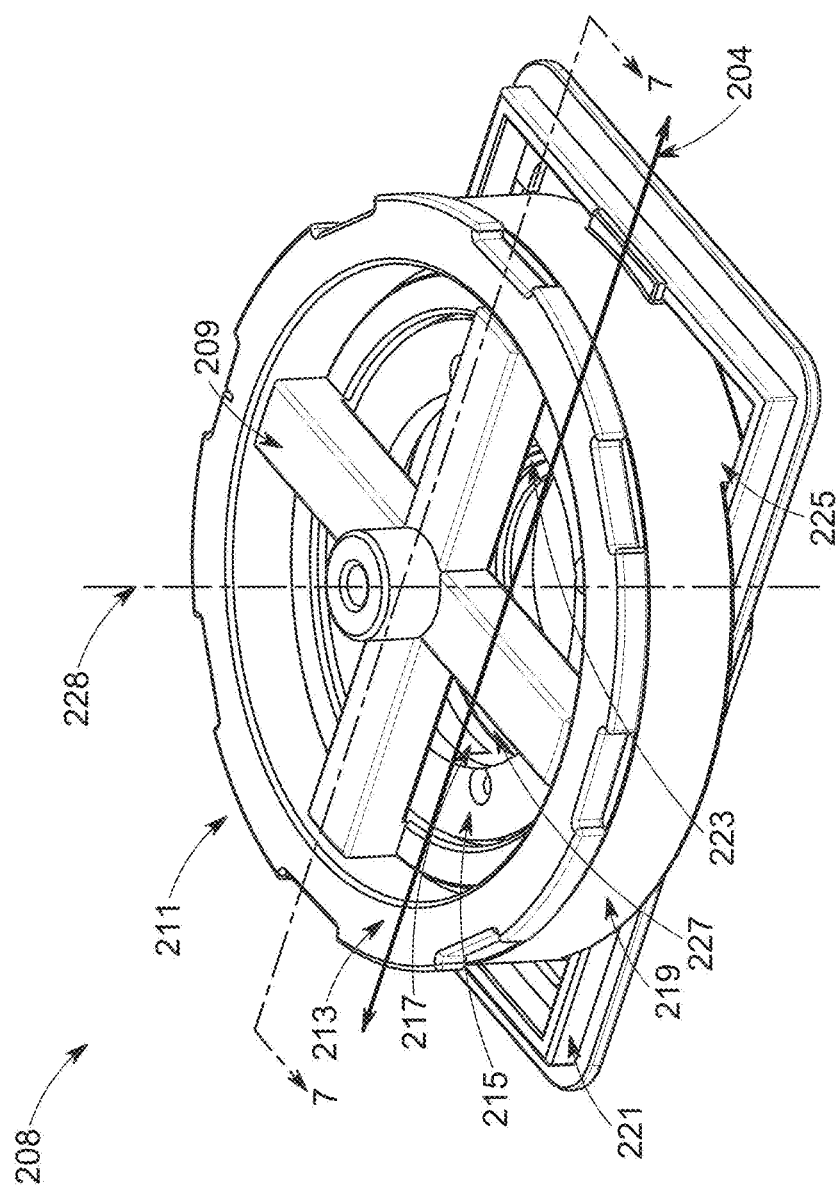
FIG. 4 is a perspective view of a stretching device, according to one exemplary embodiment.

Referring generally to FIGS. 3A-3C, the equibiaxial mechanical stretch 104 stretches the free-standing composite layer 106 (FIG. 3A), and along with it the tissue sample 102, to allow capturing an image of the caused displacement (FIG. 3B), and resulting in a map of bead displacements (FIG. 3C). Thus, the system 100 applies the equibiaxial mechanical stretch 104 to the free-standing composite layer 106 (and tissue sample 102), while simultaneously mapping a spatial distribution of displacements underneath the sample.

Referring more specifically to FIGS. 3A and 3C, a representative 0.9×0.9 square millimeters (mm$^2$) displacement map 142 is acquired near the center 113 of the free-standing composite layer 106 while being biaxially stretched. Circular patterns in the displacement map and overlaid vectors suggest that the displacements are radially symmetric.

Referring more specifically to FIG. 3B, the image is a displaced image 144 of the fiduciary markers 134 in response to the equibiaxial mechanical stretch 104. Optionally, the displaced image 142 is captured via the inverted microscope 131 (FIG. 1) and processed with the controller 133 (FIG. 1).

Referring to FIGS. 4-7, a stretching device 208 is configured to apply an uniform equibiaxial mechanical stretch 204, as disclosed above, in accordance with an alternative embodiment. The stretching device 208 includes an air-blow fixture 209 that is positioned near a top end 211 of the stretching device 208, within a main rim-body 213. The stretching device 208 further includes a top rim-element 215 that is positioned on top of the main rim-body 213 and partially within the air-blow fixture 209.

The stretching device 208 further includes a lifting rim-element 217 that is positioned below the main rim-body 213. The stretching device 208 further includes a housing 219 that generally mates with the main rim-body 213 and in which a plurality of components are positioned in whole or in part.

The stretching device 208 further includes a microscope insert 221 that generally mates with an exterior surface of the housing 219. The stretching device 208 further includes a main indenter-body 223 that is positioned within and on the top of a bottom end 225 of the housing 219.

Figure 5:
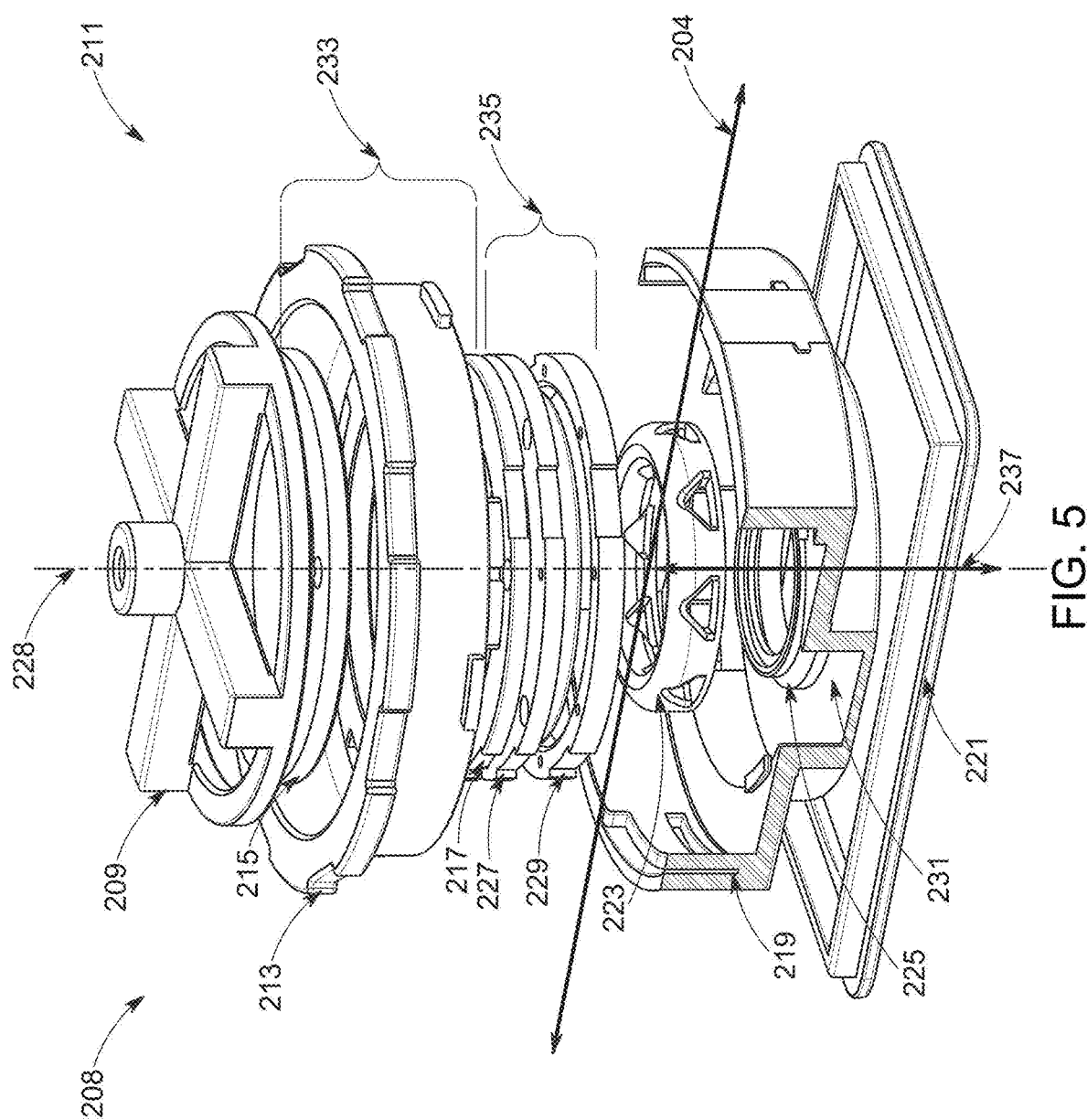
FIG. 5 is an exploded perspective view of the stretching device illustrated in FIG. 4.
Figure 6:
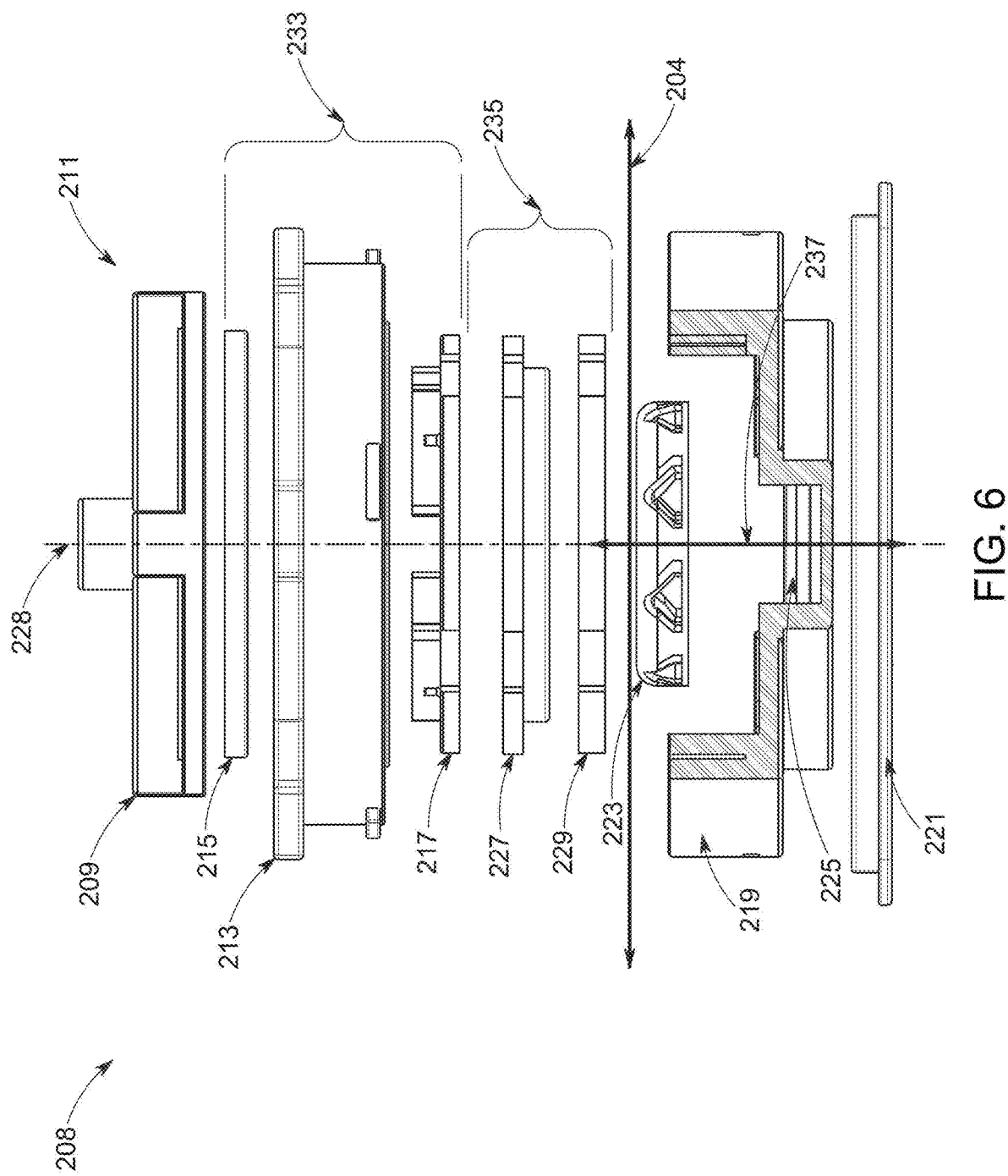
FIG. 6 is an exploded side view of the stretching device illustrated in FIG. 4.
Figure 7:
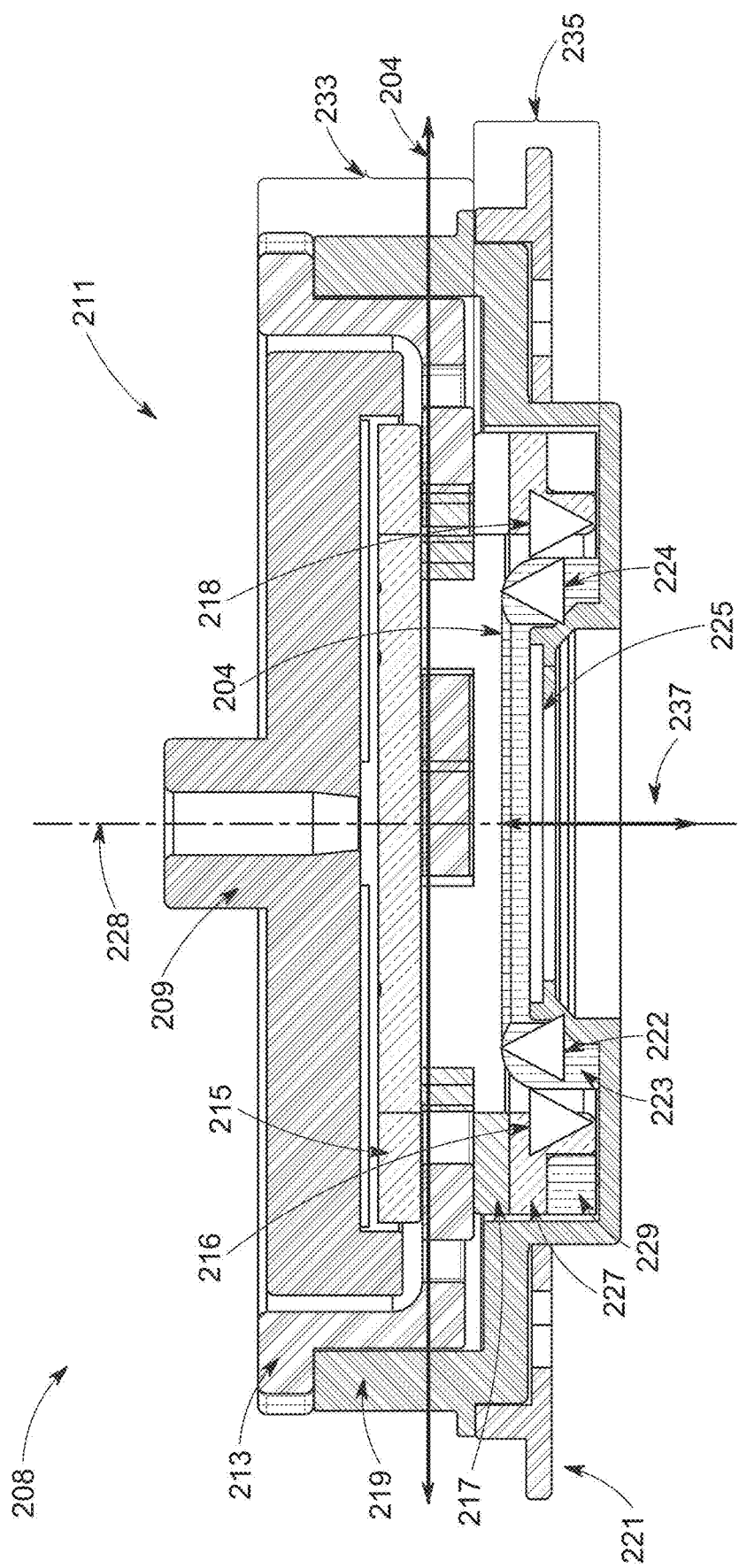
FIG. 7 is a cross-sectional view along lines "7"-"7" of FIG. 4.

The stretching device 208 further includes an upper well-element 227 that is positioned generally flush with the lifting rim-element 217, within the housing 219. The stretching device 208 further includes a lower well-element 229 that flushes with the upper well-element 227, within the housing 219. The upper well-element 227 and lower well-element 229 are collectively referred to as the well, or the well assembly 235 (as shown in FIGS. 5, 6, and 7). The lower well-element 229 is also generally flush with a bottom surface 231 of the housing 219.

The components of the stretching device 208 are centrally aligned along a central axis 228, with some of the components being relatively movable to facilitate the equibiaxial mechanical stretch 204. For example, according to one example, the main rim-body 213, the top rim-element 215, the lifting rim-element 217 (collectively referred to as the rim, or rim assembly, 233 and shown in FIGS. 5 and 6), and the well assembly 235 are configured to travel vertically along the central axis 228 towards the indenter body 223 and the bottom surface 231 of the housing 219. Thus, in the illustrated example (FIGS. 5 and 6), the well assembly 235 is positioned above the indenter 223. However, in other configurations (FIG. 7), the indenter 223 is positioned above the well assembly 235. According to other configurations, the rim assembly 233 and the well assembly 235 include less or more components than those illustrated, or include components only partially, and disclosed herein by way of example.

According to another exemplary configuration, the well assembly 235 (together with the rim assembly 233) is movable towards the indenter 223 to cause the uniform equibiaxial mechanical stretch 204. According to another exemplary configuration, both the well assembly 235 and the indenter 223 are mounted within the housing 219.

According to the disclosed illustrations, all the components of the stretching device 208, except for the microscope insert 221, have a generally circular shape, including the housing 219, the rim assembly 233, the well assembly 235, and the indenter 223. According to other exemplary configurations, one or more components of the stretching device 208 have various shapes and sized configured to facilitate the equibiaxial mechanical stretch 204.

According to the disclosed illustrations, the components of the stretching device 208 have a hollow interior that provides an imaging path 237 (shown in FIGS. 5, 6 and 7) along the central axis 228. The imaging path 237 allows the capturing of images for the tissue sample 102, as disclosed above in reference to FIG. 1.

Referring more specifically to FIG. 7, the well assembly 235 has a plurality of outer points 216, 218 that are configured to contact the first surface 120 of the free-standing composite layer 106 (illustrated in FIG. 1). The indenter 223 has a plurality of inner points 222, 224 configured to contact the second surface 126 of the free-standing composite layer 106 (illustrated in FIG. 1), along the direction of the uniform equibiaxial mechanical stretch 204. As illustrated, the outer points 216, 218 are farther from the central axis 228 and lower than the inner points 222, 224. According to this example, the inner points 222 and 224 are part of the bottom surface of the free-standing composite layer 106 that is pulled, and therefore bent, by the indenter 223 and the well assembly 235. The outer points 216, 218 are, part of the top surface of the free-standing composite layer 106 that is pulled, and therefore bent, by the indenter 223 and the well assembly 235.

Figure 8A:
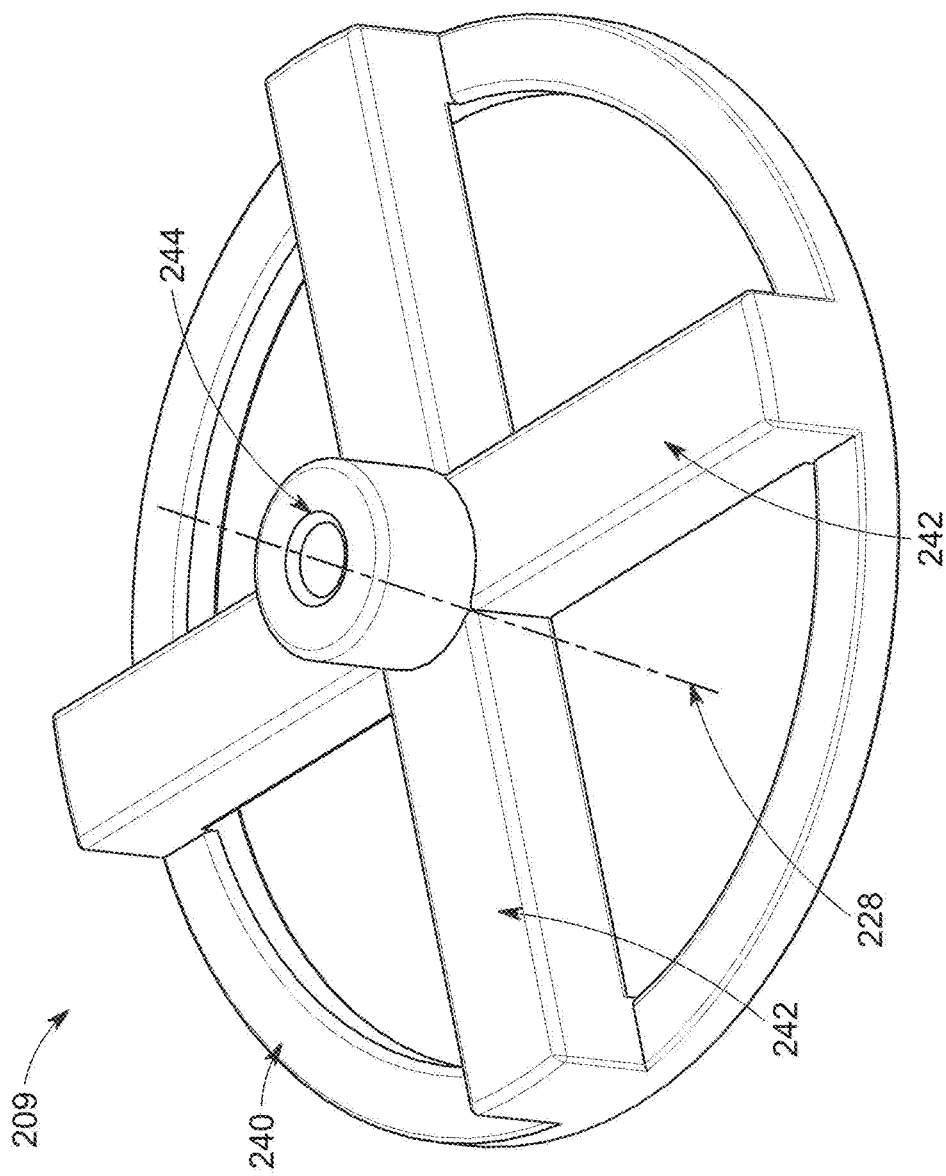
FIG. 8A is a top perspective view of an air-blow fixture for the stretching device illustrated in FIG. 4, according one exemplary embodiment.
Figure 8B:
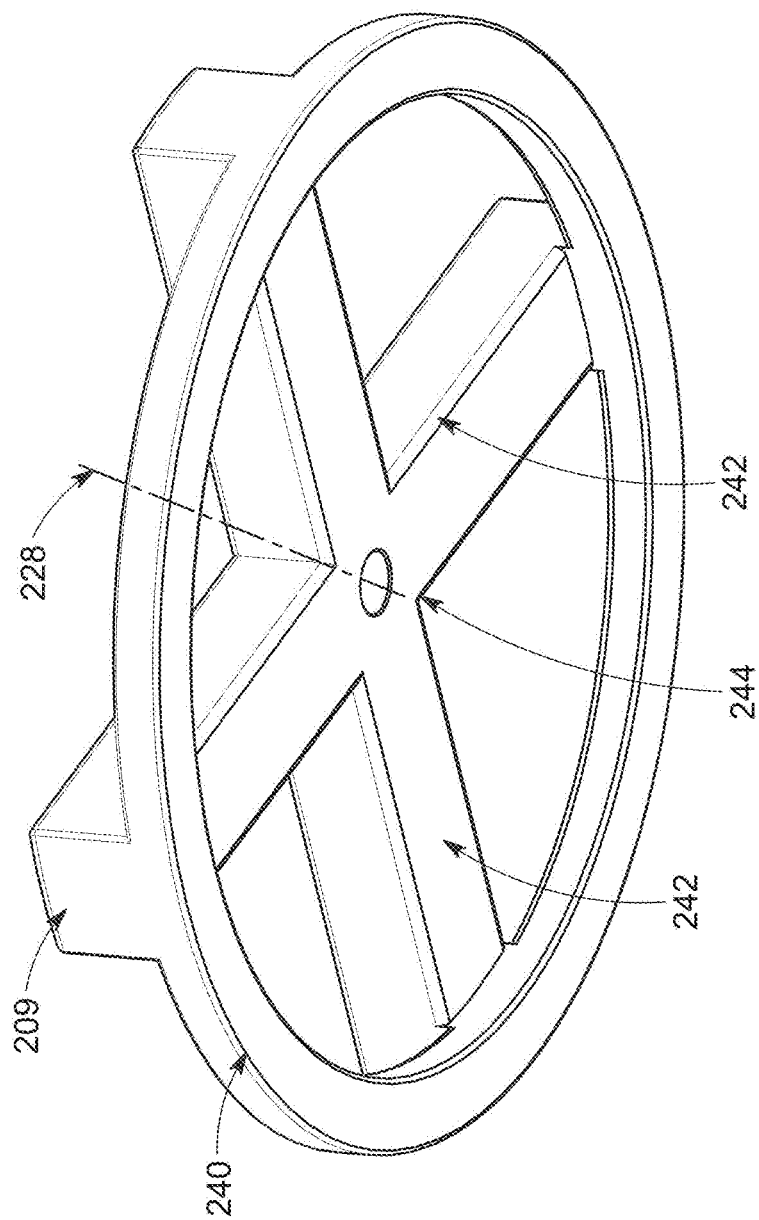
FIG. 8B is a bottom perspective view of the air-blow fixture illustrated in FIG. 8A.

Referring to FIGS. 8A and 8B, the air-blow fixture 209 has a generally circular outer base 240 and a plurality of cross-members 242. An air-blow through-hole 244 is positioned in a central area, along the central axis 228 to provide the hollow interior for the flow of air.

Figure 9A:
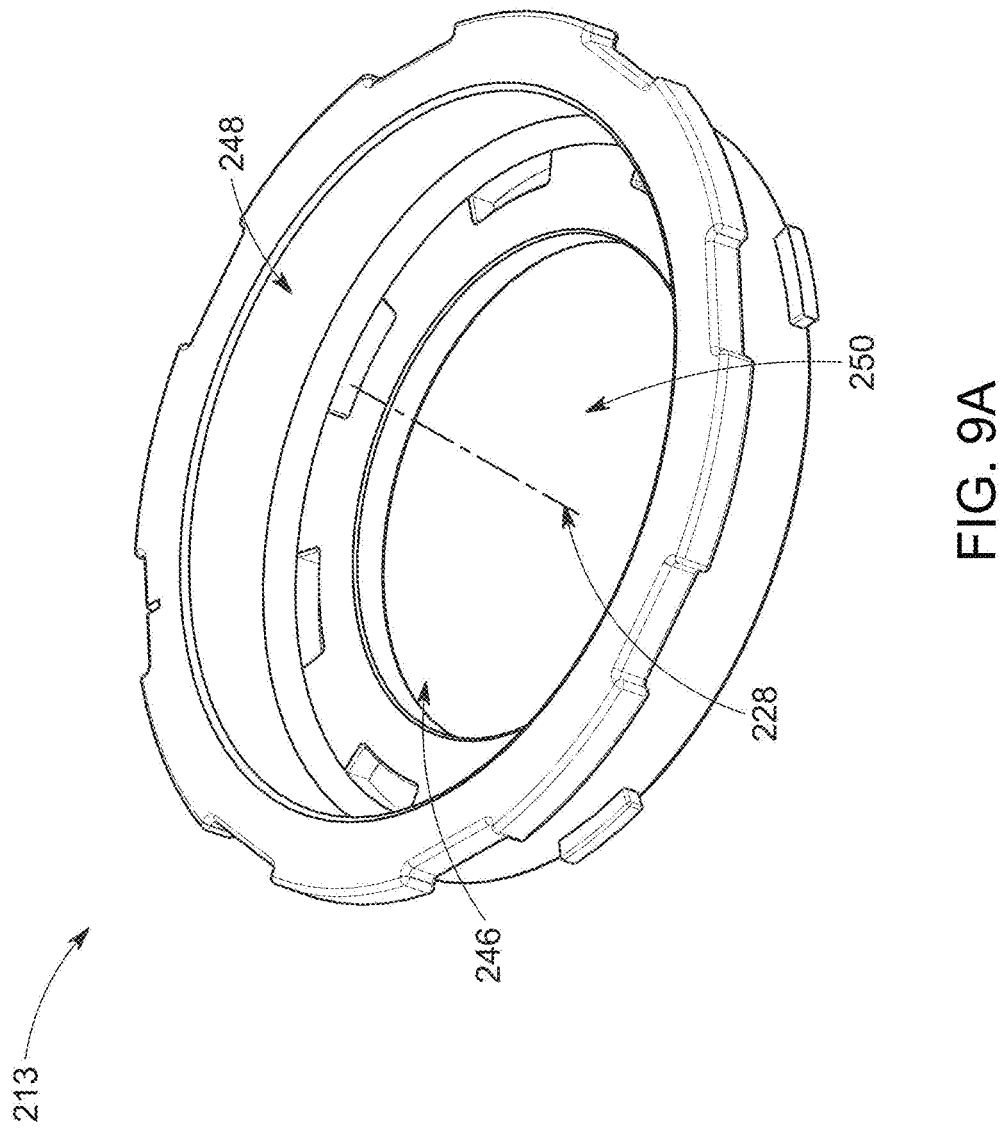
FIG. 9A is a top perspective view of a main rim-body for the stretching device illustrated in FIG. 4, according to one exemplary embodiment.
Figure 9B:
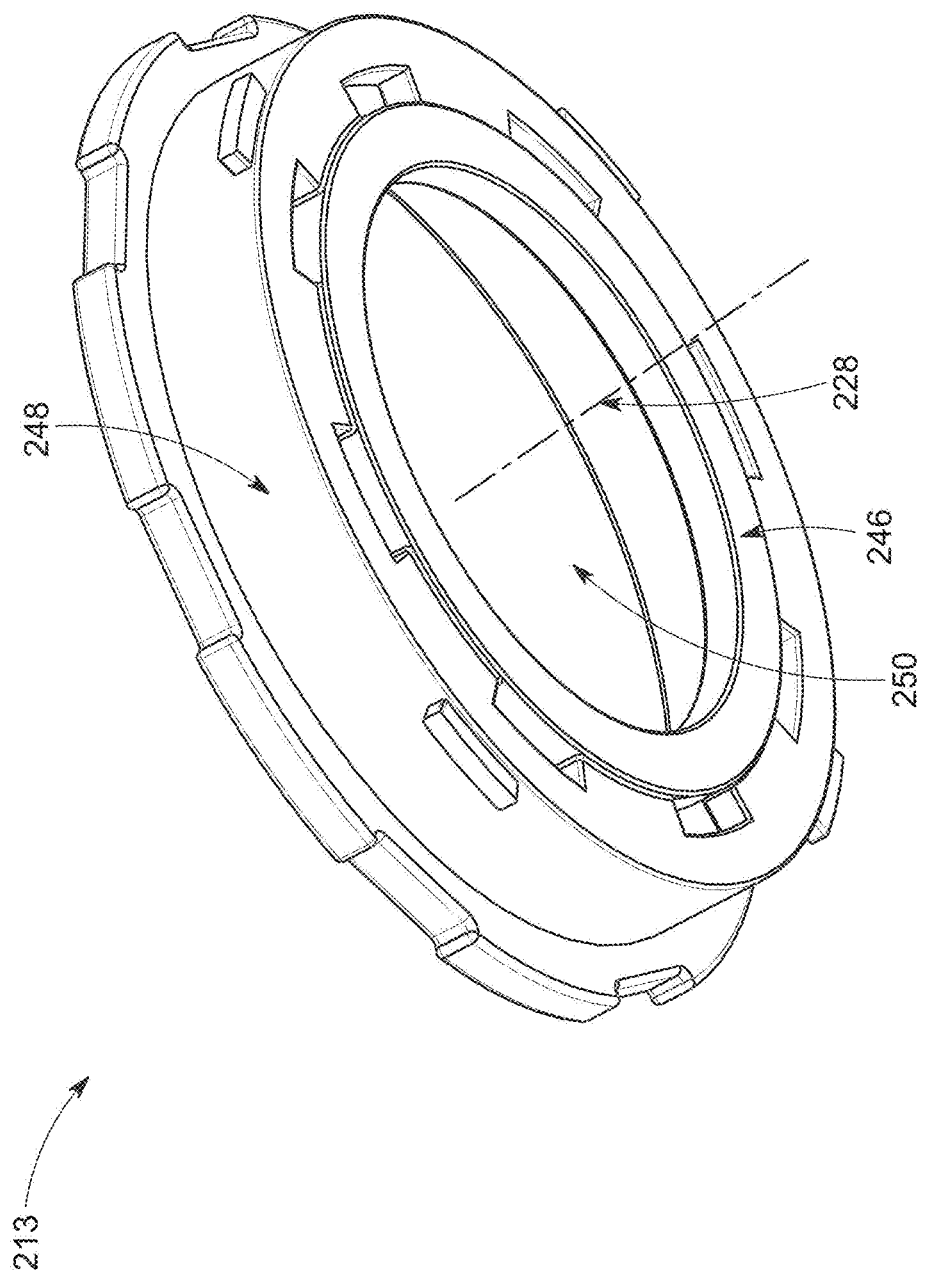
FIG. 9B is a bottom perspective view of the main rim-body illustrated in FIG. 9A.

Referring to FIGS. 9A and 9B, the main rim-body 213 has a base 246 from which a peripheral wall 248 extends. The base 246 has a hollow interior 250 that is concentric with the central axis 228.

Figure 10A:
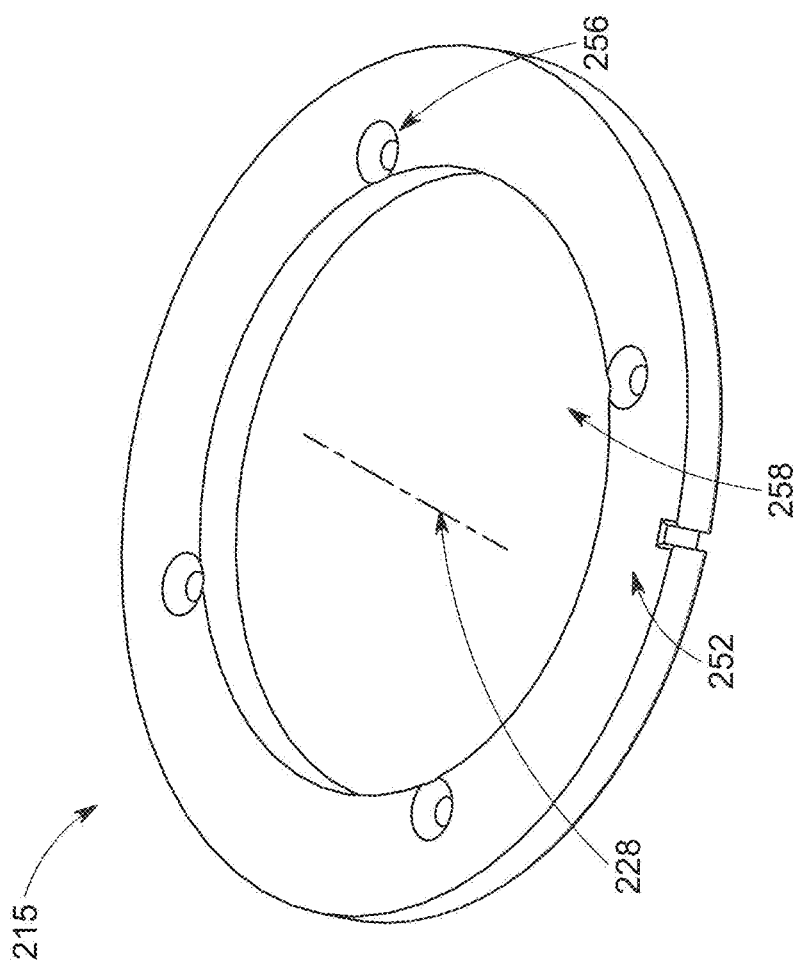
FIG. 10A is a top perspective view of a top rim-element for the stretching device illustrated in FIG. 4, according to one exemplary embodiment.
Figure 10B:
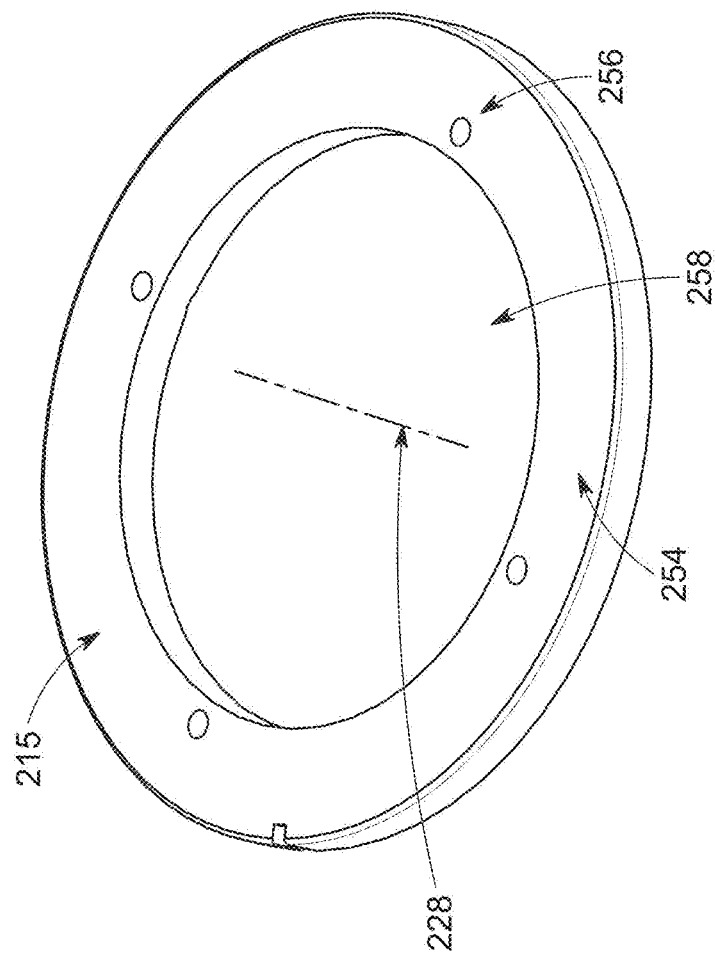
FIG. 10B is a bottom perspective view of the top rim-element illustrated in FIG. 10A.

Referring to FIGS. 10A and 10B, the top rim-element 215 is generally in the form of a circular ring with flat top and bottom surfaces 252, 254. The top rim-element 215 includes a plurality of mounting holes 256, and has a hollow interior 258 that is concentric with the central axis 228.

Figure 11A:
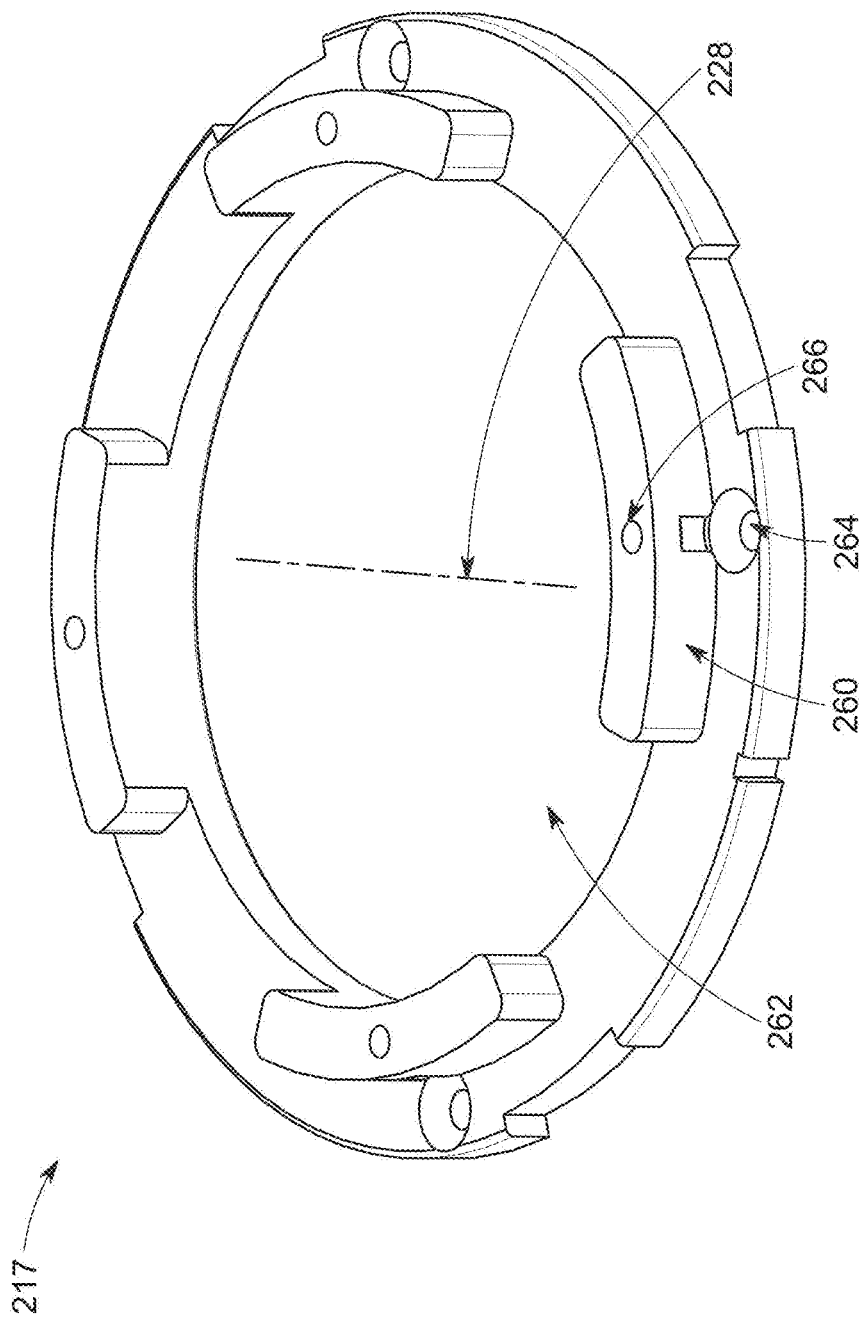
FIG. 11A is a top perspective view of a lifting rim-element for the stretching device illustrated in FIG. 4, according to one exemplary embodiment.
Figure 11B:
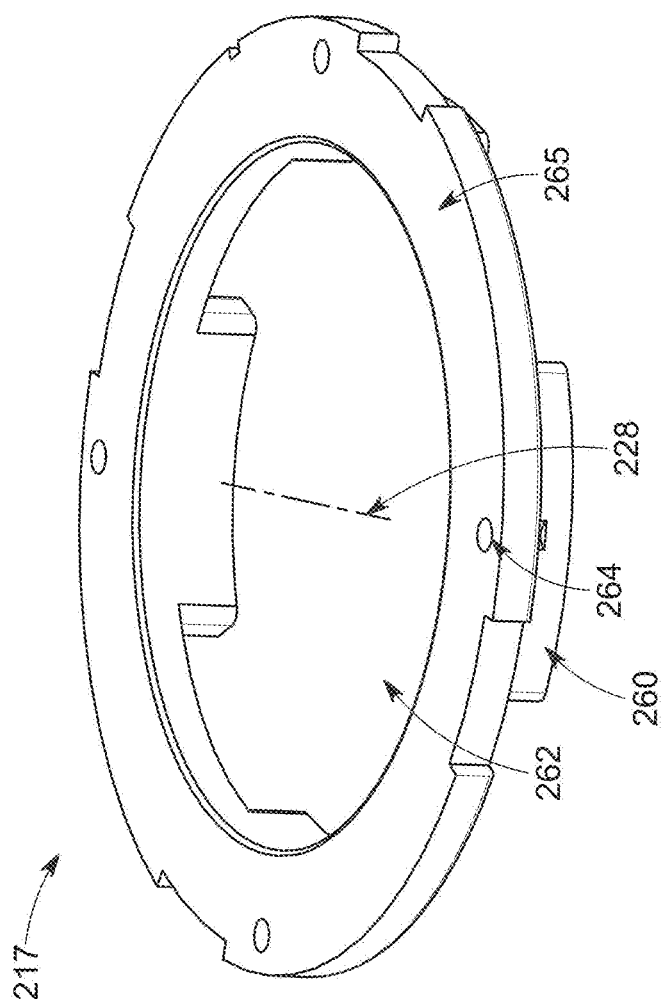
FIG. 11B is a bottom perspective view of the lifting rim-element, illustrated in FIG. 11A.

Referring to FIGS. 11A and 11B, the lifting rim-element 217 is generally in the form of a circular ring with a plurality of extending walls 260. The extending walls 260 are discontinuously formed along a hollow interior 262, which is concentric with the central axis 228. The lifting rim-element 217 includes a plurality of main mounting holes 264 (which are through-holes) and a plurality of secondary mounting holes 266.

Figure 12A:
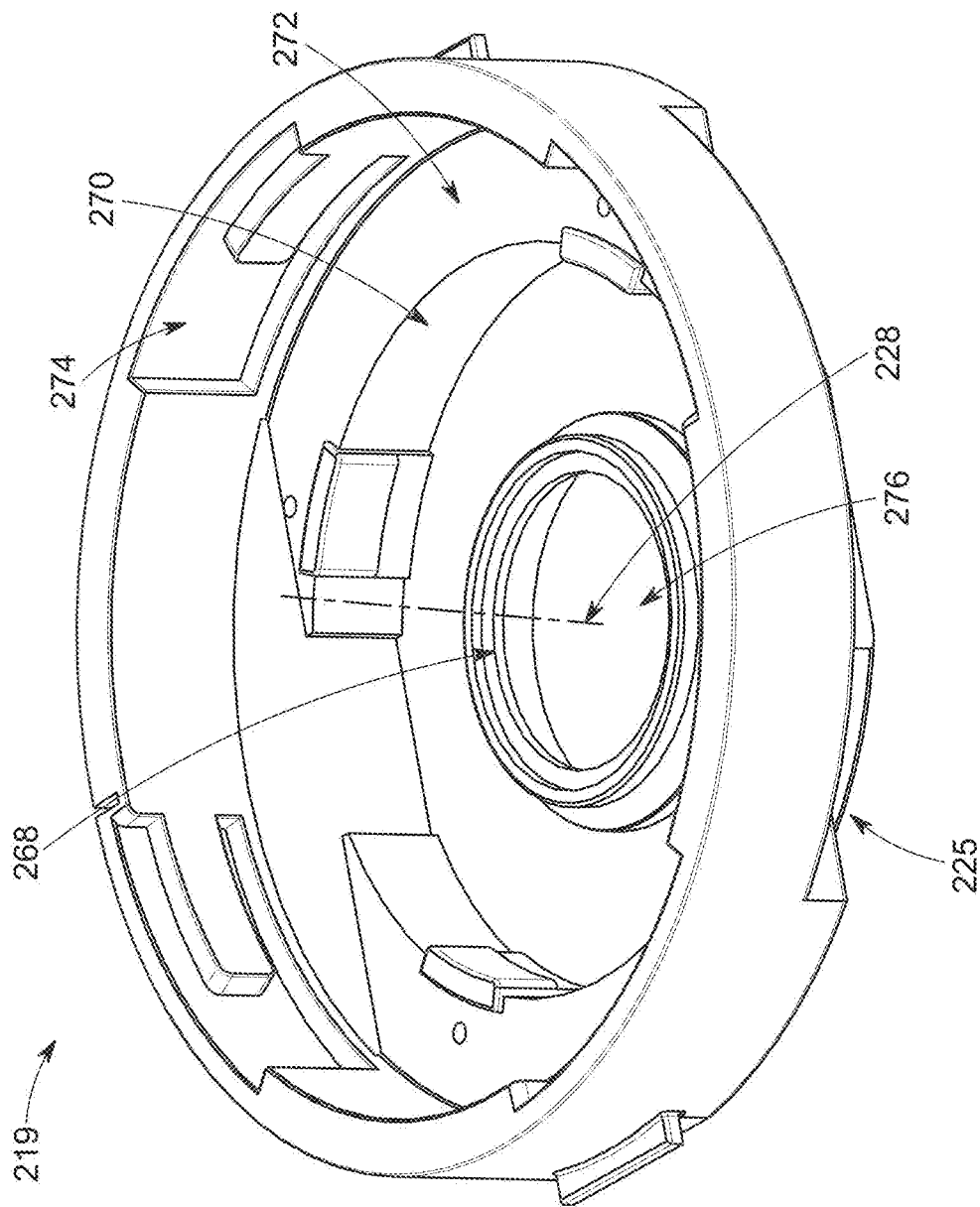
FIG. 12A is a top perspective view of a housing for the stretching device illustrated in FIG. 4, according to one exemplary embodiment.
Figure 12B:
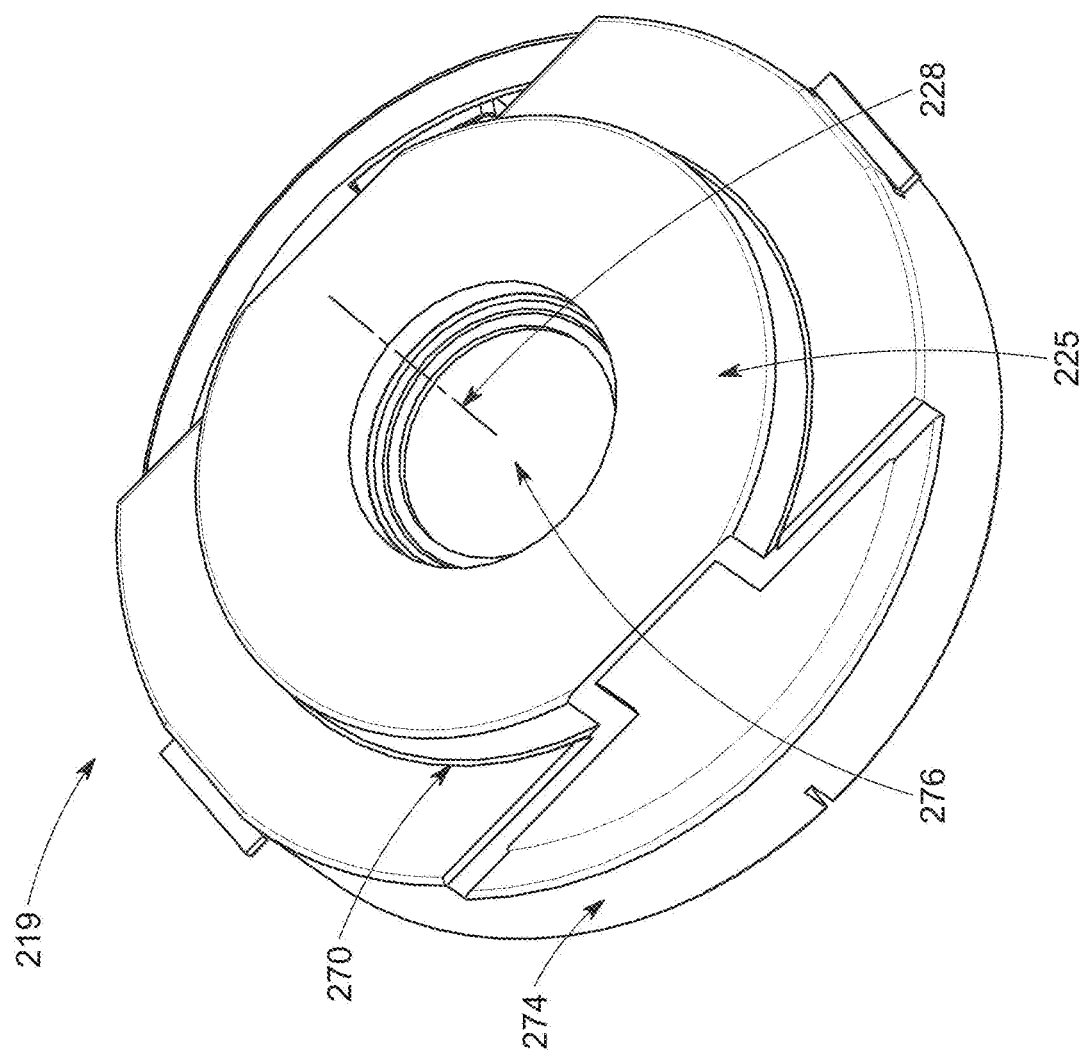
FIG. 12B is a bottom perspective view of the housing illustrated in FIG. 12A.

Referring to FIGS. 12A and 12B, the hosing 219 has a bottom surface 268 from which a first wall 270 extends perpendicularly. The housing 219 has a secondary surface 272 continuous and perpendicular with the first wall 270. The housing 219 has a second wall 274 that is continuous and perpendicular with the secondary surface 272. The housing includes a hollow interior 276 that is concentric with the central axis 228.

Figure 13A:
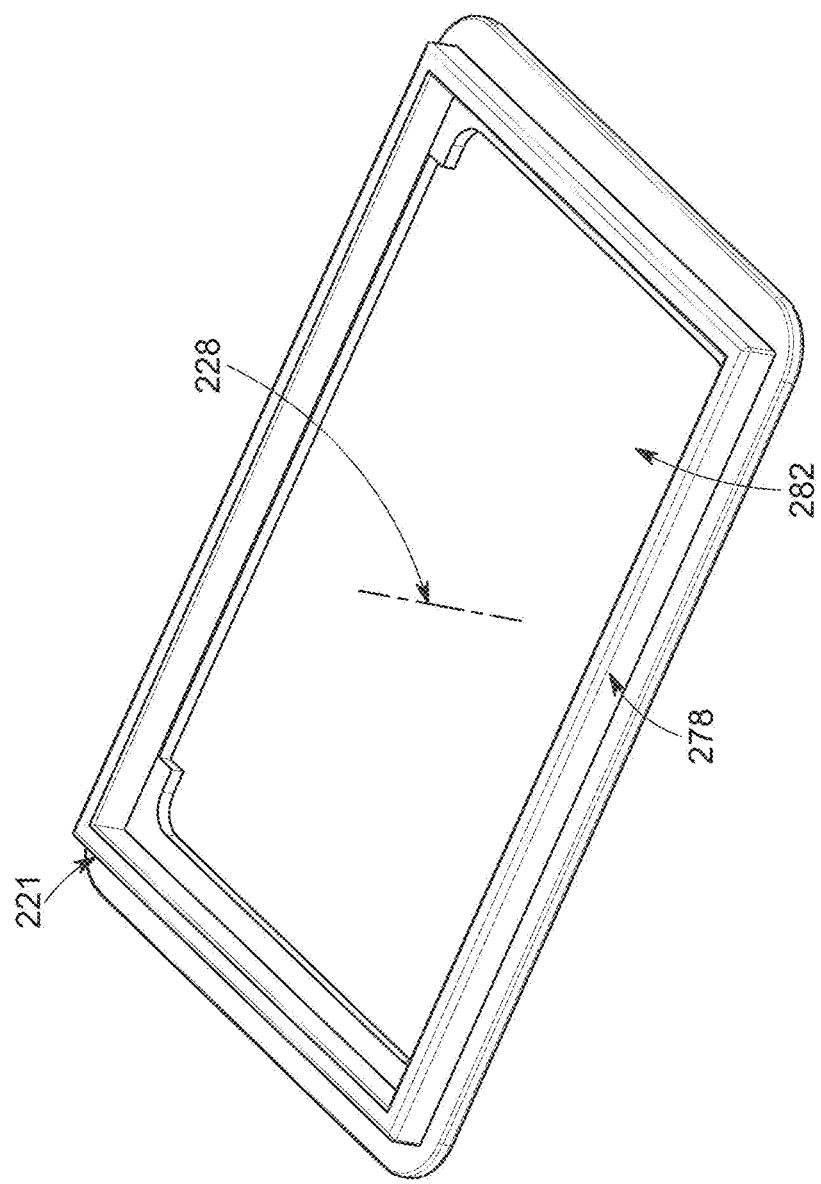
FIG. 13A is a top perspective view of a microscope insert for the stretching device illustrated in FIG. 4, according to one exemplary embodiment.
Figure 13B:
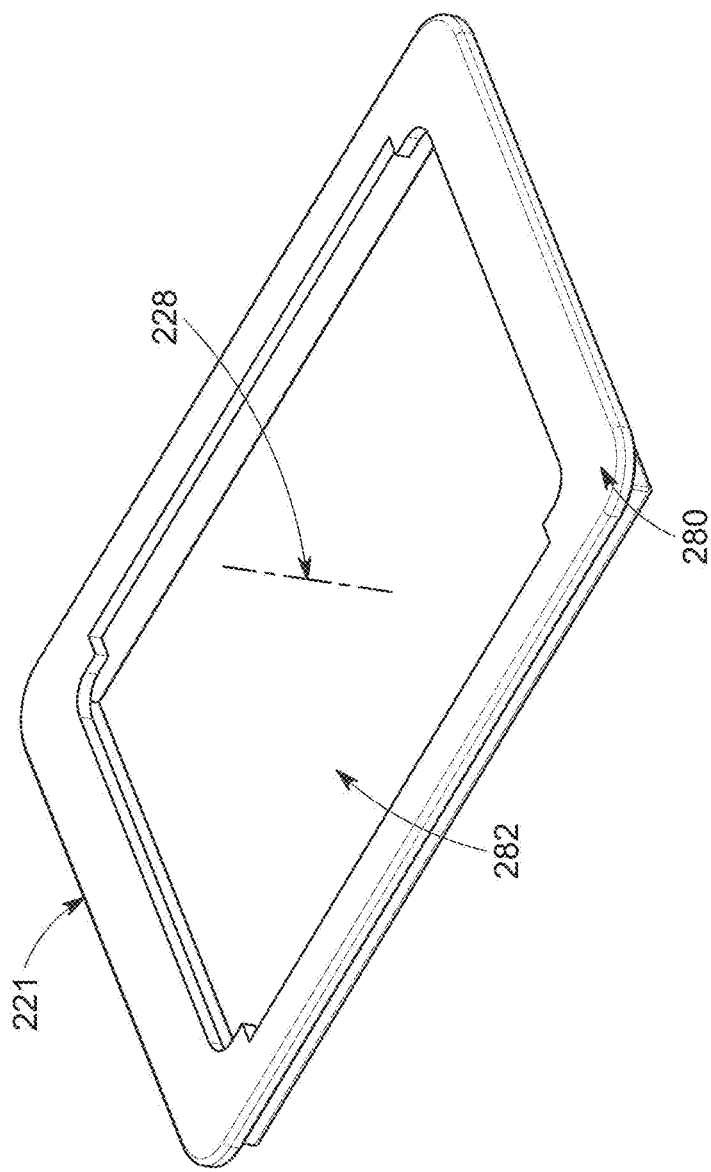
FIG. 13B is a bottom perspective view of the microscope insert illustrated in FIG. 13A.

Referring to FIGS. 13A and 13B, the microscope insert 221 has a generally rectangular shape with an internal peripheral wall 278 and a bottom flat surface 280. The microscope insert 221 has a hollow interior 282 that is centered with the central axis 228.

Figure 14A:
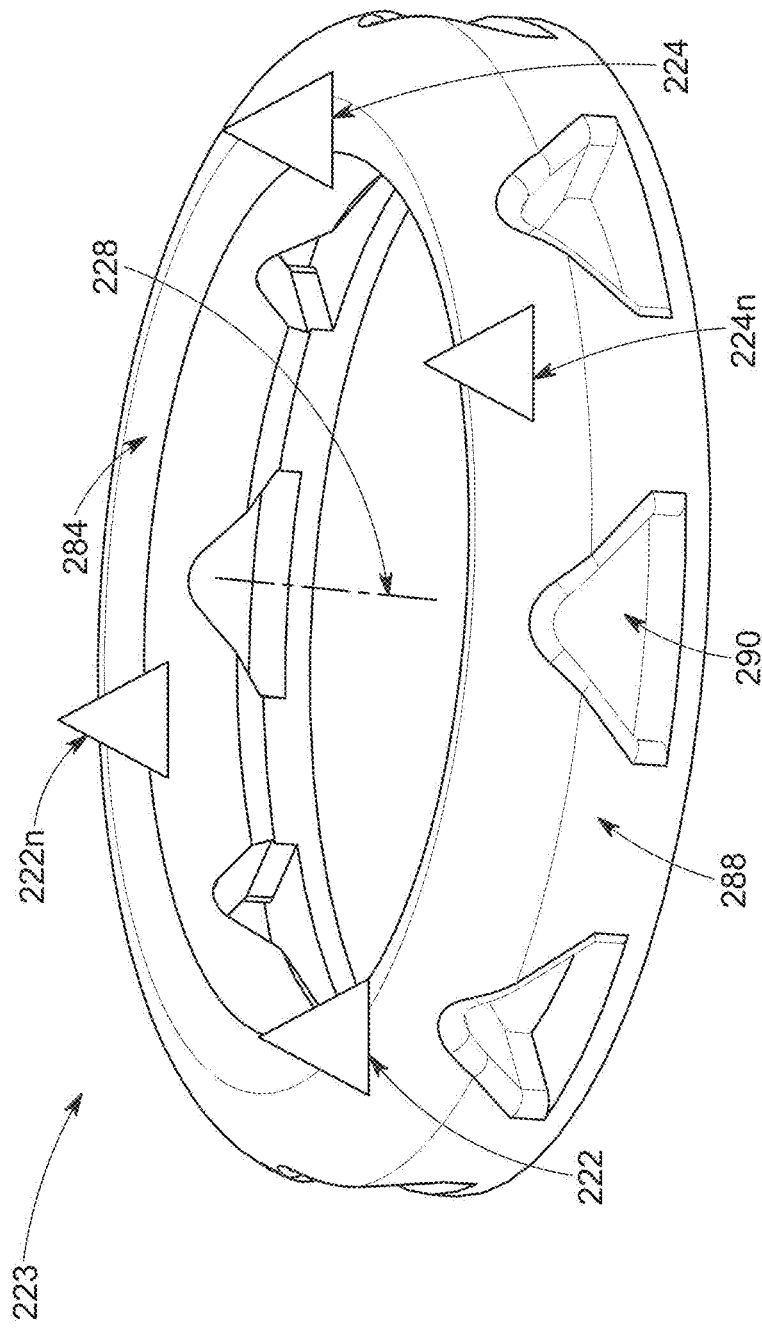
FIG. 14A is a top perspective view of an indenter-body for the stretching device illustrated in FIG. 4, according to one exemplary embodiment.
Figure 14B:
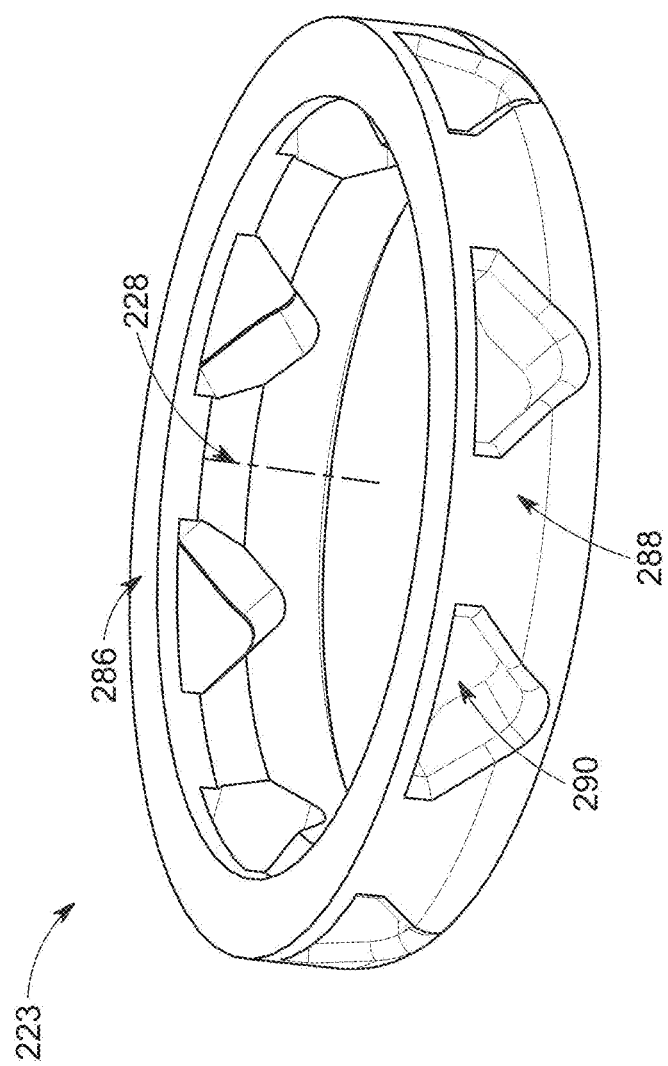
FIG. 14B is a bottom perspective view of the indenter-body illustrated in FIG. 14A.

Referring to FIGS. 14A and 14B, the indenter-body 223 has a generally circular shape with a top surface 284 and a bottom surface 286. The surfaces 284, 286 are separated by a connecting wall 288 in which a plurality of cavities 290 are formed. The indenter 223 has a hollow interior 292 that is concentric with the central axis 228. The top surface 284 is configured to make contact with the free-standing composite layer 106, and includes the plurality of inner points 222, 224, which include additional inner points 222n, 224n (shown in FIG. 14A).

Figure 15A:
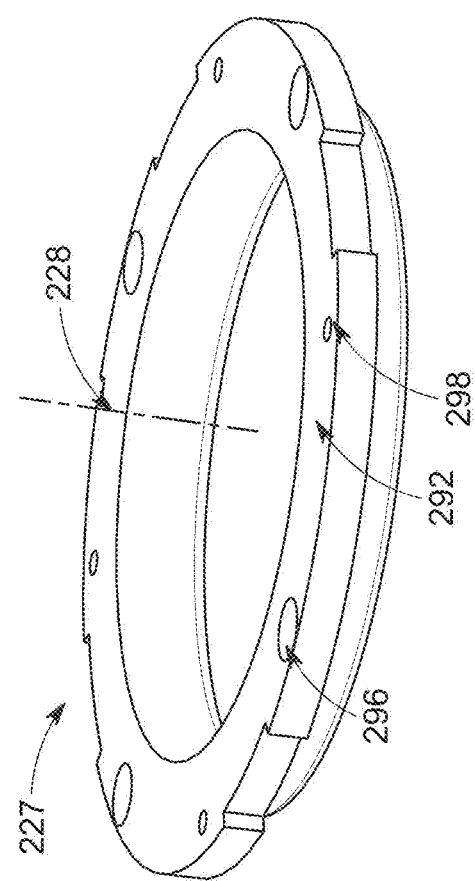
FIG. 15A is a top perspective view of an upper well-element for the stretching device illustrated in FIG. 4, according to one exemplary embodiment.
Figure 15B:
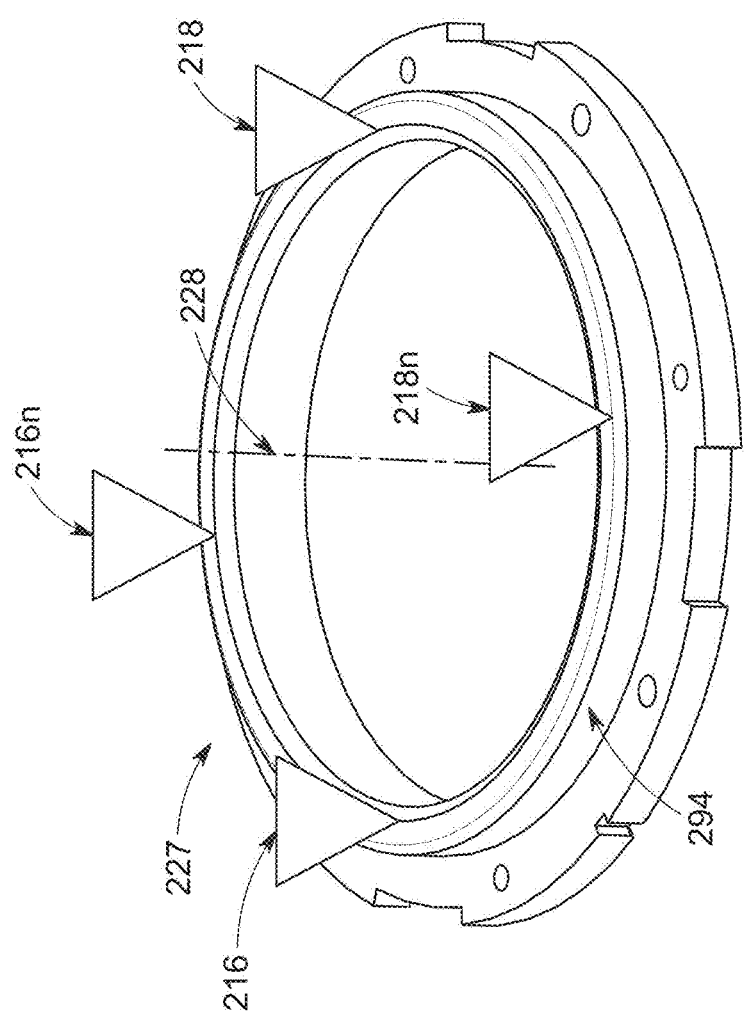
FIG. 15B is a bottom perspective view of the upper well-element illustrated in FIG. 15A.

Referring to FIGS. 15A and 15B, the upper well-element 227 has a generally circular shape with a top flat surface 292 and an internal peripheral wall 294. The upper well-element 227 has a hollow interior 282 that is concentric with the central axis 228. The upper well-element 227 includes a plurality of main mounting holes 296 and a plurality of secondary mounting holes 298. One or more of the mounting holes 296, 298 of the upper well-element 227 are through holes. The upper well-element 227 has a bottom surface at the internal peripheral wall 294 that is configured to make contact with the free-standing composite layer 106 (illustrated in FIG. 1). The upper well-element 227 includes the plurality of outer points 216, 218, which include additional outer points 216n, 218n (shown in FIG. 15B).

Figure 16A:
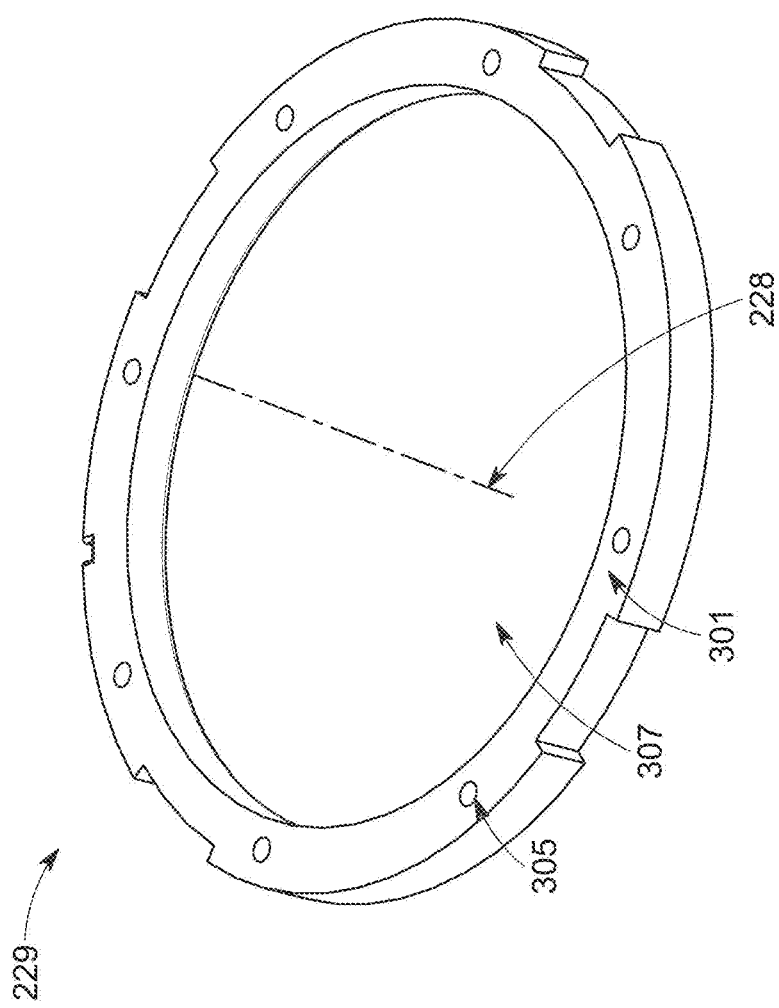
FIG. 16A is a top perspective view of a lower well-element for the stretching device illustrated in FIG. 4, according to one exemplary embodiment.
Figure 16B:
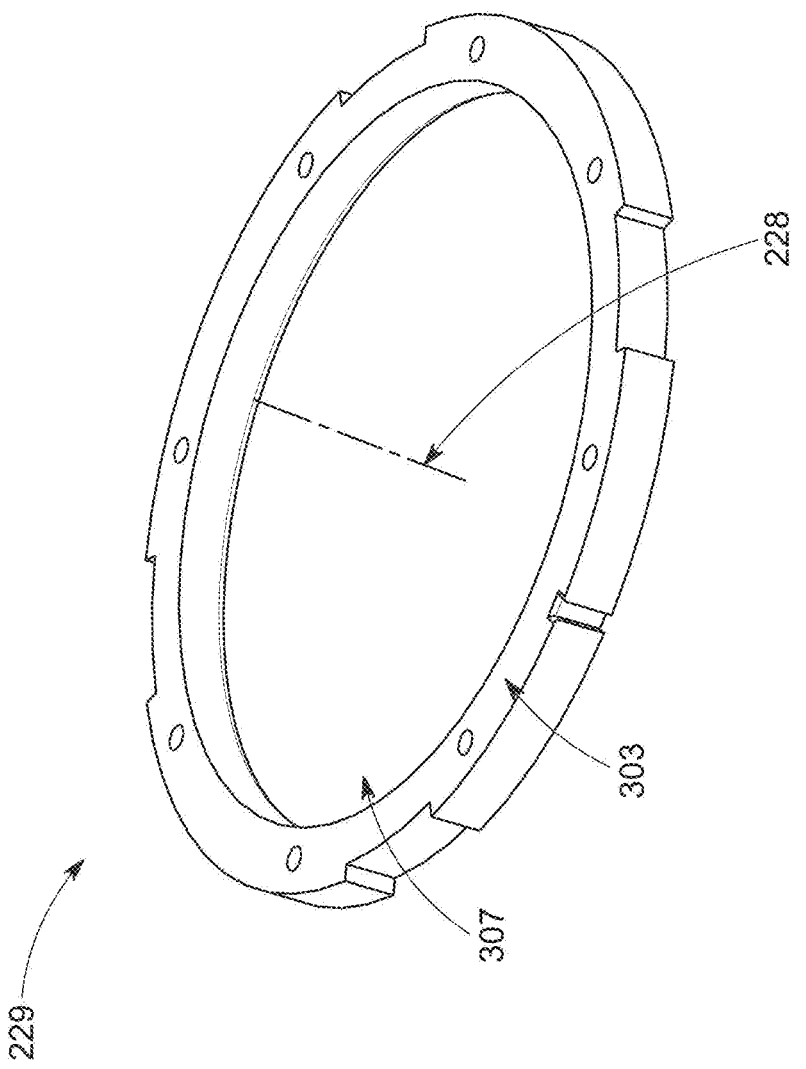
FIG. 16B is a bottom perspective view of the lower well-element illustrated in FIG. 16A.

Referring to FIGS. 16A and 16B, the lower well-element 229 is generally in the form of a circular ring with flat top and bottom surfaces 301, 303. The lower well-element 229 includes a plurality of mounting holes 305 and has a hollow interior 307 that is concentric with the central axis 228.

Although the disclosed embodiments have been illustrated and described based on an application of the system in single-well implementation, the system can be extended to multi-well implementation, e.g., 6-, 12- or 24-well format.

Methods of Classifying a Sample

Described herein are methods of classifying a sample based on the stiffness of the sample, for example, as having increased stiffness as compared to normal parameters of the sample, having decreased stiffness as compared to normal parameters of the sample, or having normal parameters. Accordingly, one aspect herein is a method of classifying a sample, the method comprising a) applying radial stretch to a substrate and determining a global radial strain of the substrate layer that is measured when the layer is stretched; b) adhering the sample to the substrate; and c) applying radial stretch the substrate having an adhered sample and determining a global radial strain of the substrate layer that is measured when the layer is stretched, wherein measuring is done via a formula of:

$$\varepsilon_{rr}{}^o = \Delta r_{memb}/r_{memb}{}^o \times 100$$

wherein $\Delta r_{memb}$ denotes the change of the radius, and $r_{memb}{}^o$ is the stress-free radius, and the local radial strain E rr that is measured when the substrate and substrate having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and wherein samples are classified as either having increased stiffness, decreased stiffness, or normal parameters.

As used herein, "normal parameters" refers to the stiffness of a sample in its natural state, i.e., healthy sample, unperturbed sample, not contacted by an agent. For example, if the sample is a diseased lung tissue, the normal parameters of the tissue would be the stiffness of the wild-type lung tissue, e.g., a native health lung tissue. As another example, if the sample is a kidney tissue contacted with an agent, the normal parameters of the tissue would be the stiffness of kidney tissue not contacted by the agent.

In one embodiment, a sample is classified as having increased stiffness if the stiffness is at least 10% greater than the normal parameters of the sample. In one embodiment, a sample is classified as having increased stiffness if the stiffness is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, or at least at least 5×, at least 10×, at least 15×, at least 20×, at least 25×, at least 30×, at least 35×, at least 40×, at least 45×, at least 50×, at least 55×, at least 60×, at least 65×, at least 70×, at least at least 80×, at least 85×, at least 90×, at least 95×, at least 100×, at least 200×, at least 300×, at least 400×, at least 500×, at least 1000×, at least 1500×, or more greater than the normal parameters of the sample. In one embodiment, a sample is classified as having increased stiffness if the stiffness is statistically greater than the normal parameters of the sample.

In one embodiment, a sample is classified as having decreased stiffness if the stiffness is at least 10% less than the normal parameters of the sample. In one embodiment, a sample is classified as having decreased stiffness if the stiffness is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more less than the normal parameters of the sample. In one embodiment, a sample is classified as having increased stiffness if the stiffness is statistically less than the normal parameters of the sample.

In one embodiment, measuring global radial strain is performed via any of the devices or systems described herein.

One advantage of any of the devices or systems described herein is that the sample can be viable prior to, during, and after measuring global radial strain. Accordingly, in one embodiment, the sample is viable during measuring. In one embodiment, the sample is viable prior to measuring. In one embodiment, the sample is viable after measuring. In one embodiment, the sample is viable prior to and after measuring. In one embodiment, the sample is viable prior to and during measuring. In one embodiment, the sample is viable during and after measuring. In one embodiment, the sample is viable prior to, during and after measuring.

Also provided herein is a method of classifying a sample, the method comprising a) applying radial stretch to a polydimethylsiloxane (PDMS) layer and determining a global radial strain of the substrate layer that is measured when the layer is stretched; b) adhering the sample to the PDMS layer; and c) applying radial stretch the PDMS layer having an adhered sample and determining a global radial strain of the substrate layer that is measured when the layer is stretched, wherein measuring is done via a formula of:

$$\varepsilon_{rr}{}^o = \Delta r_{memb}/r_{memb}{}^o \times 100$$

wherein $\Delta r_{memb}$ denotes the change of the radius, and $r_{memb}^{o}$ is the stress-free radius, and the local radial strain $\varepsilon_{rr}$ that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^{0} - \varepsilon_{rr}}{\varepsilon_{rr}^{0} h} = AE$$

wherein h is the thickness of the sample, A is a constant that is computed through a linear regression, and E is the stiffness of a sample, and wherein samples are classified as either having increased stiffness, decreased stiffness, or normal parameters.

In one embodiment, the PDMS layer is any of the PDMS layers described herein.

In one embodiment, wherein the sample is adhered to the PDMS layer.

In one embodiment, the PDMS layer further comprises the fiducial markers. Exemplary fiducial markers can include, but are not limited to, beads, ink marks, glass nanospheres, micro-posts or surface patterns. In one embodiment, the fiducial markers are fluorescent.

In one embodiment, the fiducial markers are used to measure the global radial strain and the local radial strain.

Also provided herein is a method of classifying a sample, the method comprising a) determining a global radial strain of a substrate layer that is measured when the layer is stretched without a sample using any of the systems or devices described herein; b) adhering the sample to the to a freestanding composite layer; and c) applying radial stretch the freestanding composite layer having an adhered sample and determining a global radial strain of the substrate layer that is measured when the layer is stretched, wherein measuring is done via a formula of:

$$\varepsilon_{rr}^{o} = \Delta r_{memb}/r_{memb}^{o} \times 100$$

wherein $\Delta r_{memb}$ denotes the change of the radius, and $r_{memb}^{o}$ is the stress-free radius, and the local radial strain $\varepsilon_{rr}$ that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^{0} - \varepsilon_{rr}}{\varepsilon_{rr}^{0} h} = AE$$

wherein h is the thickness of the sample, A is a constant that is computed through a linear regression, and E is the stiffness of a sample, and wherein samples are classified as either having increased stiffness, decreased stiffness, or normal parameters.

In one embodiment, the substrate can be any of the substrates described herein. Exemplary substrates include, but are not limited to, silicone, Polydimethylsiloxane (PDMS) or rubber.

In one embodiment of any aspect herein, the method further comprising the step of, prior to calculating, apply radial stretch to the sample. For example, radial stretch is applied to the sample using any of the devices, samples, or methods described herein.

Samples

In one embodiment, the sample is a biological sample. In one embodiment, the biological sample is a tissue or population of cells.

In one embodiment, the tissue is a nervous tissue (e.g., a tissue derived from the central nervous system or peripheral nervous system, spinal cord, or nerves), the muscle tissue (e.g., cardiac muscle, smooth muscle, skeletal muscle, quadriceps muscle, or diaphragm muscle), epithelial tissue (e.g., lining of GI tract organs, hollow organs, or epidermis), or connective tissue (e.g., fat or soft padding tissue, bone, or tendon tissue).

In one embodiment, the tissue is an endocrine tissue, a respiratory tissue, a digestive tissue, a reproductive tissue, a integumentary tissue, a muscular tissue, a nervous tissue, a cardiovascular tissue, a lymphatic tissue, a urinary tissue, or a skeletal tissue.

In one embodiment, the sample is a derived from an organ. For example, the sample is a tissue derived from the skull, the brain, the eye, the mouth, a tooth, a tongue, the nose, the throat, the thyroid gland, the windpipe, the larynx, an ovary, a testicle, a uterus, a ear, the vocal cord, a bone, the heart, the pancreas, the lungs, the stomach, the kidney, the liver, the large intestines, the small intestines, the colon, arteries, blood vessels, veins, or skin.

In one embodiment, the brain tissue is derived from the frontal lobe, the temporal lobe, the spinal cord, the parietal lobe, the occipital lobe, or cerebellum.

In one embodiment, the heart tissue is derived from the superior vena cava, the right atrium, the right ventricle, the inferior vena cava, pulmonary trunk, left atrium, pulmonary veins, or left atrium.

In one embodiment, the stomach tissue is derived from the esophagus, the cardia, the pyloric sphincter, the pyloric orifice, the duodenum, the pylorus, gastric folds, or fundus.

In one embodiment, the kidney tissue is derived from the ureter, the bladder or the urethra.

In one embodiment, the intestines tissue is derived from the liver, the duodenum, the ascending colon, the terminal ileum, the cecum, the stomach, the transverse colon, the descending colon, the small tissue, the sigmoid colon, or the rectum.

In one embodiment, the vein tissue is derived the from the internal jugular vein, the superior vena cava, cephalic vein, inferior vena cava, or femoral vein.

In one embodiment, the pituitary tissue is derived the from pineal gland, hypothalamus, or the pituitary gland.

In one embodiment, the sample can be a population of cells in confluence. For example, any cell in culture that is adhered to at least another cell in the population. The populations of cells can be wild type cells, genetically modified, or mutated (e.g., derived from, or modified to mimic a disease or disorder).

Biological samples can be obtained by a skilled person using standard methods know in the art. The sample can be circular, ellipse or irregular shaped thin layer samples. In one embodiment, the diameter of a sample ranges from 1 to 25 mm. For example, the sample can be 1 mm; 2 mm; 3 mm; 4 mm; 6 mm; 7 mm; 8 mm; 9 mm; 10 mm; 11 mm; 12 mm; 13 mm; 14 mm; 15 mm; 16 mm; 17 mm; 18 mm; 19 mm; 20 mm; 21 mm; 22 mm; 23 mm; 24 mm; or 25 mm in diameter. In one embodiment, the diameter of the sample is less than 1 mm or greater than 25 mm. In one embodiment, the diameter of a sample ranges from 1 to 2 mm, 1 to 3 mm, 1 to 4 mm, 1 to 5 mm, 1 to 6 mm, 1 to 7 mm, 1 to 8 mm, 1 to 9 mm, 1 to 10 mm, 1 to 11 mm, 1 to 12 mm, 1 to 13 mm, 1 to 14 mm, 1 to 15 mm, 1 to 16 mm, 1 to 17 mm, 1 to 18 mm, 1 to 19 mm, 1 to 20 mm, 1 to 21 mm, 1 to 22 mm, 1 to 23 mm, 1 to 24 mm, 2 to 25 mm, 3 to 25 mm, 4 to 25 mm, 5 to 6 to 25 mm, 7 to 25 mm, 8 to 25 mm, 9 to 25 mm, 10 to 25 mm, 11 to 25 mm, 12 to 25 mm, 13 to 14 to 25 mm, 15 to 25 mm, 16 to 25 mm, 17 to 25 mm, 18 to 25 mm, 19 to 25 mm, 20 to 25 mm, 21 to 22 to 25 mm, 23 to 25 mm, or 24 to 25 mm.

In one embodiment, the thickness of the sample ranges from 0.1 to 8 mm. For the sample can be 0.2 mm; 0.3 mm; 0.4 mm; 0.5 mm; 0.6 mm; 0.7 mm; 0.8 mm; 0.9 mm; 1 mm; 1.1 mm; 1.2 mm; 1.3 mm; 1.4 mm; 1.5 mm; 1.6 mm; 1.7 mm; 1.8 mm; 1.9 mm; 2 mm; 2.1 mm; 2.2 mm; 2.3 mm; 2.4 mm; 2.5 mm; 2.6 mm; 2.7 mm; 2.8 mm; 2.9 mm; 3 mm; 3.1 mm; 3.2 mm; 3.3 mm; 3.4 mm; 3.5 mm; 3.6 mm; 3.7 mm; 3.8 mm; 3.9 mm; 4 mm; 4.1 mm; 4.2 mm; 4.3 mm; 4.4 mm; 4.5 mm; 4.6 mm; 4.7 mm; 4.8 mm; 4.9 mm; 5 mm; 5.1 mm; 5.2 mm; 5.4 mm; 5.5 mm; 5.6 mm; 5.7 mm; 5.8 mm; 5.9 mm; 6 mm; 6.1 mm; 6.2 mm; 6.3 mm; 6.4 mm; 6.5 mm; 6.6 mm; 6.7 mm; 6.8 mm; 6.9 mm; 7 mm; 7.1 mm; 7.2 mm; 7.3 mm; 7.4 mm; 7.5 mm; 7.6 mm; 7.7 mm; 7.8 mm; 7.9 mm; or 8 mm in thickness. In one embodiment, the thickness of the sample is less than 0.1 mm or greater than 8 mm. In one embodiment, the thickness of the sample ranges from 1 to 0.2 mm, 1 to 0.3 mm, 1 to 0.4 mm, 1 to 0.5 mm, 1 to 0.6 mm, 1 to 0.7 mm, 1 to 0.8 mm, 1 to 0.9 mm, 1 to 1 mm, 1 to 1.1 mm, 1 to 1.2 mm, 1 to 1.3 mm, 1 to 1.4 mm, 1 to 1.5 mm, 1 to 1.6 mm, 1 to 1.7 mm, 1 to 1.8 mm, 1 to 1.9 mm, 1 to 2 mm, 1 to 2.1 mm, 1 to 2.2 mm, 1 to 2.3 mm, 1 to 2.4 mm, 1 to 2.5 mm, 1 to 2.6 mm, 1 to 2.7 mm, 1 to 2.8 mm, 1 to 2.9 mm, 1 to 3 mm, 1 to 3.1 mm, 1 to 3.2 mm, 1 to 3.3 mm, 1 to 3.4 mm, 1 to 3.5 mm, 1 to 3.6 mm, 1 to 3.7 mm, 1 to 3.8 mm, 1 to 3.9 mm, 1 to 4 mm, 1 to 4.1 mm, 1 to 4.2 mm, 1 to 4.3 mm, 1 to 4.4 mm, 1 to 4.5 mm, 1 to 4.6 mm, 1 to 4.7 mm, 1 to 4.8 mm, 1 to 4.9 mm, 1 to 5 mm, 1 to 5.1 mm, 1 to 5.2 mm, 1 to 5.3 mm, 1 to 5.4 mm, 1 to 5.5 mm, 1 to 5.6 mm, 1 to 5.7 mm, 1 to 5.8 mm, 1 to 5.9 mm, 1 to 6 mm, 1 to 6.1 mm, 1 to 6.2 mm, 1 to 6.3 mm, 1 to 6.4 mm, 1 to 6.5 mm, 1 to 6.6 mm, 1 to 6.7 mm, 1 to 6.8 mm, 1 to 6.9 mm, 1 to 7 mm, 1 to 7.1 mm, 1 to 7.2 mm, 1 to 7.3 mm, 1 to 7.4 mm, 1 to 7.5 mm, 1 to 7.6 mm, 1 to 7.7 mm, 1 to 7.8 mm, 1 to 7.9 mm, 0.2 to 8 mm, 0.3 to 8 mm, 0.4 to 8 mm, 0.5 to 8 mm, 0.6 to 8 mm, 0.7 to 8 mm, 0.8 to 8 mm, 0.9 to 8 mm, 1 to 8 mm, 1.1 to 8 mm, 1.2 to 8 mm, 1.3 to 8 mm, 1.4 to 8 mm, 1.5 to 8 mm, 1.6 to 8 mm, 1.7 to 8 mm, 1.8 to 8 mm, 1.9 to 8 mm, 2 to 8 mm, 2.1 to 8 mm, 2.2 to 8 mm, 2.3 to 8 mm, 2.4 to 8 mm, 2.5 to 8 mm, 2.6 to 8 mm, 2.7 to 8 mm, 2.8 to 8 mm, 2.9 to 8 mm, 3 to 8 mm, 3.1 to 8 mm, 3.2 to 8 mm, 3.3 to 8 mm, 3.4 to 8 mm, 3.5 to 8 mm, 3.6 to 8 mm, 3.7 to 8 mm, 3.8 to 8 mm, 3.9 to 8 mm, 4 to 8 mm, 4.1 to 8 mm, 4.2 to 8 mm, 4.3 to 8 mm, 4.4 to 8 mm, 4.5 to 8 mm, 4.6 to 8 mm, 4.7 to 8 mm, 4.8 to 8 mm, 4.9 to 8 mm, 5 to 8 mm, 5.1 to 8 mm, 5.2 to 8 mm, 5.3 to 8 mm, 5.4 to 8 mm, 5.5 to 8 mm, 5.6 to 8 mm, 5.7 to 8 mm, 5.8 to 8 mm, 5.9 to 8 mm, 6 to 8 mm, 6.1 to 8 mm, 6.2 to 8 mm, 6.3 to 8 mm, 6.4 to 8 mm, 6.5 to 8 mm, 6.6 to 8 mm, 6.7 to 8 mm, 6.8 to 8 mm, 6.9 to 8 mm, 7 to 8 mm, 7.1 to 8 mm, 7.2 to 8 mm, 7.3 to 8 mm, 7.4 to 8 mm, 7.5 to 8 mm, 7.6 to 8 mm, 7.7 to 8 mm, 7.8 to 8 mm, or 7.9 to 8 mm.

In one embodiment, the aspect ratio (i.e., thickness/diameter) is 1:3. The combination of sample thickness and diameter should be chosen to result in a proper aspect ratio as described here.

In one embodiment, the plane aspect ratio: $0.5 \sim < x/y \sim < 1$ (y is the longest sample dimension, x is the dimension orthogonal to y). When measured both at the top and bottom surface of a sample, two principal dimensions, x and y, should result in a proper in plane aspect ratio as described here.

In one embodiment, samples having a stiffness of 0.5~20 kPa are measured using the 'soft' composite layer of 3 kPa PDMS coated on a silicone membrane. In one embodiment, samples having a stiffness of 20-200 kPa are measured using the 'stiff' composite layer of 20 kPa PDMS coated on a silicone membrane. In one embodiment, samples having a stiffness of 200 kPa~2000 kPa are measured using a layer of silicone membrane only. In all three configurations (i.e., soft, stiff, silicone membrane only), an additional layer of sticky PDMS coating on top enables sample adhesion.

In one embodiment, the sample is a non-biological sample. For example, the non-biological sample is a composite material, a superconductor material, colloid material, a sponge, a gel, a fabric, and food.

Assessing Effect of Agent on Classification of Sample

Methods, devices, or systems described herein can be used to assess the effect of an agent on a sample. For example, methods, devices or systems described herein can be used to determine if an agent increases or decreases the stiffness of a sample, and thus, alters the classification of the sample. Alternatively, methods, devices or systems described herein can be used to determine if an agent does not alter the stiffness of a sample, and thus, does not change the classification of the sample.

Accordingly, providing herein is a method of assessing the effect of at least one agent on classification of a sample, a method of assessing the effect of at least one agent on classification of a sample, the method comprising a) applying radial stretch to a substrate and determining a global radial strain of the substrate layer that is measured when the layer is stretched; b) adhering the sample to the substrate; c) contacting the sample with the at least one agent; and d) applying radial stretch the substrate having an adhered sample and determining a global radial strain of the substrate layer that is measured when the layer is stretched, wherein measuring is done via a formula of:

$$\varepsilon_{rr}^o = \Delta r_{memb}/r_{memb}^o \times 100$$

wherein $\Delta r_{memb}$ denotes the change of the radius, and $r_{memb}^o$ is the stress-free radius, and the local radial strain $\varepsilon_{rr}$ that is measured when the substrate and substrate having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and wherein samples are classified as either having increased stiffness, decreased stiffness, or normal parameters.

Also provided herein is a method of assessing the effect of at least one agent on classification of a sample, the method comprising a) applying radial stretch to a polydimethylsiloxane (PDMS) layer and determining a global radial strain of the substrate layer that is measured when the layer is stretched; b) adhering the sample to the PDMS layer; c) contacting the sample with the at least one agent; and d) applying radial stretch the PDMS layer having an adhered sample and determining a global radial strain of the substrate layer that is measured when the layer is stretched, wherein measuring is done via a formula of:

$$\varepsilon_{rr}^{\circ}=\Delta r_{memb}/r_{memb}^{\circ}\times 100$$

wherein $\Delta r_{memb}$ denotes the change of the radius, and $r_{memb}^{\circ}$ is the stress-free radius, and the local radial strain $\varepsilon_{rr}$ that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and wherein samples are classified as either having increased stiffness, decreased stiffness, or normal parameters.

Also provided herein is a method of assessing the effect of at least one agent on classification of a sample, the method comprising a) determining a global radial strain of a substrate layer that is measured when the layer is stretched without a sample using any of the systems or devices described herein; b) adhering the sample to the to a freestanding composite layer; c) contacting the sample with the at least one agent; and d) applying radial stretch the freestanding composite layer having an adhered sample and determining a global radial strain of the substrate layer that is measured when the layer is stretched, wherein measuring is done via a formula of:

$$\varepsilon_{rr}^{\circ}=\Delta r_{memb}/r_{memb}^{\circ}\times 100$$

wherein $\Delta r_{memb}$ denotes the change of the radius, and $r_{memb}^{\circ}$ is the stress-free radius, and the local radial strain E rr that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and wherein samples are classified as either having increased stiffness, decreased stiffness, or normal parameters.

In one embodiment, the change in the global radial strain of a substrate that is measured without a sample and the local radial strain that is measured with a sample adhered to a substrate is a readout of the effect of the at least one agent on the stiffness of the sample.

Also provided herein is a method of assessing the effect of at least one agent on the classification of a sample comprising: calculating a first stiffness of the sample; contacting the sample with at least one agent; calculating a second stiffness of the sample, wherein samples are classified as either having increased stiffness, decreased stiffness, or normal parameters.

Also provided herein is a method of assessing the effect of at least one agent on the classification of a sample comprising adhering a sample to a substrate; applying radial stretch to the substrate; calculating a first stiffness of the sample, contacting the sample with at least one agent; applying radial stretch to the substrate; and calculating a second stiffness of the sample, wherein samples are classified as either having increased stiffness, decreased stiffness, or normal parameters.

Also provided herein is a method of assessing the effect of at least one agent on the classification of a sample comprising applying a sample to any of the systems of devices described herein; calculating a first stiffness of the sample; contacting the sample with at least one agent; and calculating a second stiffness of the sample, wherein samples are classified as either having increased stiffness, decreased stiffness, or normal parameters.

In one embodiment, the method further comprising the step of comparing the first stiffness and second stiffness. For example, if the first stiffness is greater than the stiffness stretch, it can be determined that the at least one agent decreased the stiffness of the sample. Alternatively, if the first stiffness is less than the second stiffness, it can be determined that the at least one agent increased the stiffness of the sample. If the first stiffness is equal to the second stiffness, it can be determined that the at least one agent does not alter the stiffness of the sample.

In one embodiment, the contacting is for a time sufficient for the at least one agent to alter the sample. For example, the contacting can be for less than 1 minute, or at least 1 minute. In one embodiment, contact is for at least 1 min; 2 min; 3 min; 4 min; 5 min; 6 min; 7 min; 8 min; 9 min; 10 min; 11 min; 12 min; 13 min; 14 min; 15 min; 16 min; 17 min; 18 min; 19 min; 20 min; 21 min; 22 min; 23 min; 24 min; 25 min; 26 min; 27 min; 28 min; 29 min; 30 min; 31 min; 32 min; 33 min; 34 min; 35 min; 36 min; 37 min; 38 min; 39 min; 40 min; 41 min; 42 min; 43 min; 44 min; 45 min; 46 min; 47 min; 48 min; 49 min; 50 min; 51 min; 52 min; 53 min; 54 min; 55 min; 56 min; 57 min; 58 min; 59 min; or at least 1 hour; 2 hours; 3 hours; 4 hours; 5 hours; 6 hours; 7 hours; 8 hours; 9 hours; 10 hours; 11 hours; 12 hours; 13 hours; 14 hours; 15 hours; 16 hours; 17 hours; 18 hours; 19 hours; 20 hours; 21 hours; 22 hours; 23 hours; or at least 1 day; 2 days; 3 days; 4 days; 5 days; 6 days; 7 days; 8 days; 9 days; 10 days; 11 days; 12 days; 13 days; 14 days; 15 days; 16 days; 17 days; 18 days; 19 days; 20 days; 21 days; 22 days; 23 days; 24 days; 25 days; 26 days; 27 days; 28 days; 29 days; 30 days; or more.

In one embodiment, the at least one agent is applied at least once. For example, the at least one agent is applied at least twice. When an agent is applied at least twice, the agent is applied at the same concentration during each contact. When an agent is applied at least twice, the agent is applied at different concentrations during each contact.

In one embodiment, when the at least one agent is at least two agents, a stiffness can be measured multiple times. For example, a first stiffness can be measured after contact with a first agent, and a second stiffness can be measured after contact with a second agent.

In one embodiment, the method further comprises the step of comparing the global radial stretch of the sample contacted with at least one agent to the global radial stretch of the sample prior to contact with the at least one agent.

In one embodiment, the change in the global radial strain of a substrate that is measured without a sample and the local radial strain that is measured with a sample adhered to a substrate is a readout of the effect of the at least one agent on the stiffness of the sample.

In one embodiment, the at least one agent is at least two agents, e.g., at least 2, 3, 4, 5, 6, 7, 8, 9, or more agents contact the sample. In one embodiment, the at least one agent is at least two agents, and the at least two agents contact the sample at the same time, i.e., a sample is contacted with at least two agents at substantially the same time.

In one embodiment, the at least one agent is at least two agents, and the at least two agents contact the sample at the different times, i.e., a sample is contacted with at least a first agent at a first time point and with at least a second agent at a second time point.

In one embodiment, the at least one agent is a library of agents, e.g., a library of small molecules, Fabs, enzymes, etc.

In one embodiment, the at least one agent is identified as effecting a sample if the sample exhibits a decrease in stiffness following contact with the at least one agent. In one embodiment, the at least one agent decreases the stiffness of the sample by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more following contact of the sample compared to an appropriate control. As used herein, an "appropriate control" refers to the stiffness of the sample prior to contacting with the agent, or the stiffness of an otherwise identical sample that is not in contact with the agent. A skilled person can measure stiffness of a sample using any of the systems, devices, or methods described herein. In one embodiment, the at least one agent is identified as effecting a sample if the sample exhibits a statistically significant decrease in stiffness following contact with the at least one agent.

In one embodiment, the at least one agent is identified as effecting a sample if the sample exhibits an increase in stiffness following contact with the at least one agent. In one embodiment, the at least one agent increases the stiffness of the sample by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, or at least at least 5×, at least 10×, at least 15×, at least 20×, at least at least 30×, at least 35×, at least 40×, at least 45×, at least 50×, at least 55×, at least 60×, at least 65×, at least 70×, at least 75×, at least 80×, at least 85×, at least 90×, at least 95×, at least 100×, at least 200×, at least 300×, at least 400×, at least 500×, at least 1000×, at least 1500×, or more following contact of the sample compared to an appropriate control. As used herein, an "appropriate control" refers to the stiffness of the sample prior to contacting with the agent, or the stiffness of an otherwise identical sample that is not in contact with the agent. A skilled person can measure stiffness of a sample using any of the systems, devices, or methods described herein. In one embodiment, the at least one agent is identified as effecting a sample if the sample exhibits a statistically significant increase in stiffness following contact with the at least one agent.

In one embodiment, the at least one agent is identified as having no effect on a sample if the sample exhibits a no change in stiffness following contact with the at least one agent as compared to an appropriate control. As used herein, an "appropriate control" refers to the stiffness of the sample prior to contacting with the agent, or the stiffness of an otherwise identical sample that is not in contact with the agent. A skilled person can measure stiffness of a sample using any of the systems, devices, or methods described herein.

In one embodiment, the methods, devices or systems are used herein to assess the effect of an agent for a disease or disorder is selected from COPD, pulmonary fibrosis, asthma, pneumonia, and viral infections, including COVID-19, cancer, cardiovascular disease, or orthopedic diseases.

Agents

In various aspects described herein, an agent is applied to a sample to be classified using devices, systems, or methods described herein. For example, an agent is applied to a sample that is subsequently measured to assess stiffness of the sample.

In one embodiment, the agent includes, but are not limited to, a small molecule, an antibody or antibody fragment, a peptide, such as an enzyme, an antisense oligonucleotide, a genome editing system, or an RNAi.

An agent can inhibit and activate e.g., the transcription, or the translation of any gene in the cell or tissue. An agent can inhibit the activity or alter the activity (e.g., such that the activity no longer occurs, or occurs at a reduced rate) of any gene in the cell. An agent can alter the structure or composition of the tissue by chemically eliminating components, such as an enzyme digesting the tissue.

In one embodiment, an agent decreases the stiffness of the sample following contact of the sample. In one embodiment, an agent decreases the stiffness of the sample at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more following contact of the sample compared to an appropriate control. As used herein, an "appropriate control" refers to the stiffness of the sample prior to contacting with the agent, or the stiffness of an otherwise identical sample that is not in contact with the agent. A skilled person can measure stiffness of a sample using any of the systems, devices, or methods described herein.

In one embodiment, an agent increases the stiffness of the sample following contact of the sample. In one embodiment, an agent increases the stiffness of the sample at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, or at least at least 5×, at least 10×, at least 15×, at least 20×, at least 25×, at least 30×, at least 35×, at least 40×, at least 45×, at least 50×, at least 55×, at least 60×, at least 65×, at least 70×, at least 75×, at least 80×, at least 85×, at least 90×, at least 95×, at least 100×, at least 200×, at least 300×, at least 400×, at least 500×, at least 1000×, at least 1500×, or more following contact of the sample compared to an appropriate control. As used herein, an "appropriate control" refers to the stiffness of the sample prior to contacting with the agent, or the stiffness of an otherwise identical sample that is not in contact with the agent. A skilled person can measure stiffness of a sample using any of the systems, devices, or methods described herein.

In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be identified from a library of diverse compounds.

In various embodiments, the agent is a small molecule. As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In some embodiments, the agent is a polypeptide. As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues provided herein are preferred to be in the "L" isomeric form. However, residues in the "D" isomeric form may be substituted for any L-amino acid residue provided the desired properties of the polypeptide are retained.

In one embodiment, the agent is an antibody or antigen-binding fragment thereof. As used herein, the term "antibody" refers to a polypeptide that includes at least one immunoglobulin variable domain or immunoglobulin variable domain sequence and which specifically binds a given antigen. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions.

The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g., de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, nanobodies, humanized antibodies, chimeric antibodies, and the like.

In one embodiment of any of the aspects, the agent that is a humanized, monoclonal antibody or antigen-binding fragment thereof, or an antibody reagent. As used herein, "humanized" refers to antibodies from non-human species (e.g., mouse, rat, sheep, etc.) whose protein sequence has been modified such that it increases the similarities to antibody variants produce naturally in humans. In one embodiment of any of the aspects, the humanized antibody is a humanized monoclonal antibody. In another embodiment of any of the aspects, the humanized antibody is a humanized polyclonal antibody. In another embodiment of any of the aspects, the humanized antibody is for therapeutic use.

In one embodiment, antibody is a depleting antibody.

An antibody can be tethered or linked to other agents, moieties, toxins, or substances; these tethered or linked agents, moieties, toxins, or substances can be delivered to the cell or population thereof, e.g., via binding of the antibody.

In one embodiment of any of the aspects, the agent is an antisense oligonucleotide. As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under cellular conditions to a gene. Thus, oligonucleotides are chosen that are sufficiently complementary to the target, i.e., that hybridize sufficiently well and with sufficient specificity in the context of the cellular environment, to give the desired effect. For example, an antisense oligonucleotide that inhibits a gene of interest may comprise at least 5, at least 10, at least 15, at least 20, at least 25, at least 30, or more bases complementary to a portion of the coding sequence of the gene.

In one embodiment, the agent is a genome editing system including, but not limited to, zinc finger nucleases, TALENS, meganucleases, and CRISPR/Cas systems. In another embodiment of any of the aspects, the genomic editing system used to incorporate the nucleic acid encoding one or more guide RNAs into the cell's genome is not a CRISPR/Cas system; this can prevent undesirable cell death in cells that retain a small amount of Cas enzyme/protein. It is also contemplated herein that either the Cas enzyme or the sgRNAs are each expressed under the control of a different inducible promoter, thereby allowing temporal expression of each to prevent such interference.

When a nucleic acid encoding one or more sgRNAs and a nucleic acid encoding an RNA-guided endonuclease each need to be administered in vivo, the use of an adenovirus associated vector (AAV) is specifically contemplated. Other vectors for simultaneously delivering nucleic acids to both components of the genome editing/fragmentation system (e.g., sgRNAs, RNA-guided endonuclease) include lentiviral vectors, such as Epstein Barr, Human immunodeficiency virus (HIV), and hepatitis B virus (HBV). Each of the components of the RNA-guided genome editing system (e.g., sgRNA and endonuclease) can be delivered in a separate vector as known in the art or as described herein.

In one embodiment, the agent promotes RNA inhibition. Inhibitors of the expression of a given gene can be an inhibitory nucleic acid. In some embodiments of any of the aspects, the inhibitory nucleic acid is an inhibitory RNA (iRNA or RNAi). The RNAi can be single stranded or double stranded.

The term "RNAi" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA (i.e., although siRNAs are believed to have a specific method of in vivo processing resulting in the cleavage of mRNA, such sequences can be incorporated into the vectors in the context of the flanking sequences described herein).

The iRNA can be siRNA, shRNA, endogenous microRNA (miRNA), or artificial miRNA. In one embodiment of any of the aspects, an iRNA as described herein effects inhibition of the expression and/or activity of a target a gene. In some embodiments of any of the aspects, the agent is siRNA that inhibits a gene. In some embodiments of any of the aspects, the agent is shRNA that inhibits gene.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions The RNA of an iRNA can be chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference.

In one embodiment of any of the aspects, the agent is miRNA. microRNAs are small non-coding RNAs with an average length of 22 nucleotides. These molecules act by binding to complementary sequences within mRNA molecules, usually in the 3' untranslated (3'UTR) region, thereby promoting target mRNA degradation or inhibited mRNA translation. The interaction between microRNA and mRNAs is mediated by what is known as the "seed sequence", a 6-8-nucleotide region of the microRNA that directs sequence-specific binding to the mRNA through imperfect Watson-Crick base pairing. More than 900 microRNAs are known to be expressed in mammals. Many of these can be grouped into families on the basis of their seed sequence, thereby identifying a "cluster" of similar microRNAs. A miRNA can be expressed in a cell, e.g., as naked DNA. A miRNA can be encoded by a nucleic acid that is expressed in the cell, e.g., as naked DNA or can be encoded by a nucleic acid that is contained within a vector.

The agent may be contained in and thus further include a vector. Many such vectors useful for transferring exogenous genes into target mammalian cells are available. The vectors may be episomal, e.g., plasmids, virus-derived vectors such cytomegalovirus, adenovirus, etc., or may be integrated into the target cell genome, through homologous recombination or random integration, e.g., retrovirus-derived vectors such as MMLV, HIV-1, ALV, etc. In some embodiments, combinations of retroviruses and an appropriate packaging cell line may also find use, where the capsid proteins will be functional for infecting the target cells. Usually, the cells and virus will be incubated for at least about 24 hours in the culture medium. The cells are then allowed to grow in the culture medium for short intervals in some applications, e.g., 24-73 hours, or for at least two weeks, and may be allowed to grow for five weeks or more, before analysis. Commonly used retroviral vectors are "defective", i.e., unable to produce viral proteins required for productive infection. Replication of the vector requires growth in the packaging cell line.

The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector.

One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free cells. Another non-integrative viral vector is adenoviral vector and the adeno-associated viral (AAV) vector.

Another non-integrative viral vector is RNA Sendai viral vector, which can produce protein without entering the nucleus of an infected cell. The F-deficient Sendai virus vector remains in the cytoplasm of infected cells for a few passages, but is diluted out quickly and completely lost after several passages (e.g., 10 passages).

Another example of a non-integrative vector is a minicircle vector. Minicircle vectors are circularized vectors in which the plasmid backbone has been released leaving only the eukaryotic promoter and cDNA(s) that are to be expressed.

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

Method for Identifying Disease or Disorder

Disease and disorder states associated with a change in tissue stiffness can be identified using any of the methods, devices or systems described herein. For example, provided herein is a method of identifying a subject as having a disease or disorder associated with increased stiffness of a tissue comprising: obtaining a sample from a subject; calculating a stiffness of the sample; comparing the stiffness of the sample to a stiffness of an appropriate control sample; and identifying the subject as having a disease or disorder associated with increased stiffness of a tissue if the stiffness of the sample is greater than the stiffness of the appropriate control sample. When comparing stiffness of samples, e.g., one sample from a healthy subject and one sample from a diseased subject, the diseased group is classified as having increased or decreased stiffness compared to the healthy group when there is statistically significant change in stiffness between groups.

Also provided is a method of identifying a subject as having a disease or disorder associated with increased stiffness of a tissue comprising: receiving the results of an assay that calculated a stiffness of the sample obtained from a subject; comparing the stiffness the sample obtained to a stiffness of an appropriate control sample; and identifying the subject as having a disease or disorder associated with increased stiffness of a tissue if the stiffness of the sample obtained from the subject is greater than the stiffness of the appropriate control sample.

Also provided is a method of identifying a subject as having a disease or disorder associated with decreased stiffness of a tissue comprising: obtaining a sample from a subject; calculating a stiffness of the sample; comparing the stiffness the sample to a stiffness of an appropriate control sample; and identifying the subject as having a disease or disorder associated with decreased stiffness of a tissue if the stiffness of the sample is less than the stiffness of the appropriate control sample.

Also provided is a method of identifying a subject as having a disease or disorder associated with decreased stiffness of a tissue comprising: receiving the results of an assay that calculated a stiffness of the sample obtained from a subject; comparing the stiffness the sample obtained from the subject to a stiffness of an appropriate control sample; and identifying the subject as having a disease or disorder associate with decreased stiffness of a tissue if the stiffness of the sample obtained from the subject is less than the stiffness of the appropriate control sample.

Assays that calculate the global radial stretch of the sample include any of the methods described herein, or includes using any of the devices or systems described herein.

In one embodiment, the disease or disorder associated with increased stiffness of a tissue is fibrosis of a tissue. In one embodiment, the disease or disorder associated with increased stiffness of a tissue is cancer of a tissue. Exemplary disease or disorders associated with increased stiffness of a tissue include, but is not limited to, lung cancer, pulmonary hypertension, pulmonary fibrosis, idiopathic Pulmonary Fibrosis, liver cancer, liver fibrosis, kidney fibrosis, kidney cancer, Glomerulosclerosis and tubulointerstitial fibrosis, benign bladder pathology, bladder dysfunction, arteriosclerosis, cardiovascular disease (CVD), aging, Scleroderma.

In one embodiment, the disease or disorder associated with decreased stiffness of a tissue is selected from the group consisting of emphysema, a subtype of Chronic Obstructive Pulmonary Disease (COPD)4

In one embodiment, the disease or disorder is selected from COPD, pulmonary fibrosis, asthma, pneumonia, and viral infections, including COVID-19, cancer, cardiovascular disease, or orthopedic diseases.

Network Modeling

Also provided herein is a method of converting images obtained from a patient's lung sample into a patient-specific network model of linear springs. In one embodiment, the network configuration represents the structure of the tissue in a personalized spring network form. In one embodiment, the area distribution of the network is matched to the desired best-fit distribution of the images using a developed method called 'Probability Density Function Matching' (PDF Matching).

Also provided herein is a method of calculating an effective stiffness value for the septal walls of a patient's lung sample through the network modeling. Once the network is created and the physiological units of the springs are defined, the networks are mechanically stretched in silico to determine their mechanical properties.

In one embodiment, the total strain energy E_net of the network is given by, $$E_{net} = \sum_{i=1}^{n} \frac{1}{2} k_i \Delta x_i^2$$

where n is the number of springs in the network, $k\_i\neg$ is the spring constant of spring i, and $\Delta x\_i$ is the extension of spring i.

In one embodiment, the second derivative of this equation divided by the sample volume is an estimate of the stiffness (Young's modulus) of the whole network. Using the measured modulus by the stiffness measuring system as described herein for a given network configuration, the effective septal wall modulus is back calculated.

Although the disclosed embodiments have been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

While various embodiments of the present disclosure have been described above, it should be understood that they have been presented by way of example only, and not limitation. Numerous changes to the disclosed embodiments can be made in accordance with the disclosure herein, without departing from the spirit or scope of the disclosure. Thus, the breadth and scope of the present disclosure should not be limited by any of the above described embodiments. Rather, the scope of the disclosure should be defined in accordance with the following claims and their equivalents.

The invention described herein can be described in any of the following numbered paragraphs:

1. A system for determining a stretch condition of a biological tissue, the system comprising:
   a free-standing composite layer configured to receive a tissue sample of the biological tissue, the free-standing composite having a first surface, a second surface that is opposing to the first surface, and two opposing ends, the free-standing composite layer including
   a flexible membrane extending between the two opposing ends,
   a plurality of fiduciary markers interspersed with the flexible membrane, and
   an adhesive area extending at least a portion of the first surface, the adhesive area configured to receive with a no-slip interface the tissue sample; and
   a stretching device including
   an indenter having a plurality of inner points configured to contact the second surface of the free-standing composite layer, and
   a rim aligned with the indenter along a central axis, the rim having a plurality of outer points configured to contact the first surface near the two opposing ends of the free-standing composite layer, the plurality of outer points being farther from the central axis than the plurality of inner points;
   wherein at least one of the indenters and the rim is movable to cause an uniform equibiaxial mechanical stretch of the free-standing composite layer and the tissue sample.

2. The system of paragraph 1, wherein the plurality of fiduciary markers are interspersed on the flexible membrane.

3. The system of any of the preceding paragraphs, wherein the plurality of fiduciary markers are interspersed within the flexible membrane.

4. The system of any of the preceding paragraphs, wherein the flexible membrane is a first layer of the free-standing composite layer, the free-standing composite layer further including a second layer overlaying in a non-slip interface with the first layer, the plurality of fiduciary markers being embedded in the second layer.

5. The system of any of the preceding paragraphs, wherein the flexible membrane is a first layer of the free-standing composite layer, the free-standing composite layer further including a second layer overlaying in a non-slip interface with the first layer, the adhesive area being part of the second layer.

6. The system of any of the preceding paragraphs, wherein the flexible membrane is a first layer of the free-standing composite layer, the free-standing composite layer further including:
a second layer overlaying in a non-slip interface with the first layer, the plurality of fiduciary markers being embedded in the second layer; and
a third layer overlaying in a non-slip interface with the second layer, the third layer including the adhesive area.

7. The system of any of the preceding paragraphs, wherein at least one of the plurality of fiduciary markers is a fluorescent bead.

8. The system of any of the preceding paragraphs, wherein the flexible membrane includes one or more of a silicon material and a polydimethylsiloxane (PDMS) material.

9. The system of any of the preceding paragraphs, wherein the indenter has a hollow interior between the plurality of inner points.

10. The system of any of the preceding paragraphs, further comprising an inverted microscope configured for imaging the plurality of fiduciary markers, the inverted microscope providing a displaced image of the plurality of fiduciary markers in response to the uniform equibiaxial mechanical stretch.

11. The system of any of the preceding paragraphs, wherein the displaced image is a displacement map of the plurality of fiduciary markers.

12. The system of any of the preceding paragraphs, wherein the rim is configured to travel vertically towards the indenter.

13. The system of any of the preceding paragraphs, wherein the stretching device includes a well within which the rim and indenter are both mounted.

14. The system of any of the preceding paragraphs, wherein the rim is positioned above the indenter.

15. The system of any of the preceding paragraphs, wherein each of the well, the rim, and the indenter have a circular shape.

16. The system of any of the preceding paragraphs, wherein the rim and the indenter are aligned within the rim along a central axis.

17. The system of any of the preceding paragraphs, wherein each of the well, the rim, and the indenter have a hollow interior, the hollow interior being positioned over at least a portion of the plurality of fiduciary markers, the hollow interior providing an imaging path for capturing a displaced image of the plurality of fiduciary markers in response to the uniform equibiaxial mechanical stretch.

18. The system of any of the preceding paragraphs, further comprising a controller configured to determine a global radial strain of a substrate layer that is measured when the layer is stretched without a sample via a formula of:

$$\varepsilon_{rr} = \Delta r_{memb}/r_{memb}^o \times 100$$

wherein $\Delta r_{memb}$ denotes the change of the radius, and $r_{memb}^o$ is the stress-free radius, and the local radial strain $\varepsilon_{rr}$ that is measured when the substrate and substrate having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and wherein samples are classified as either having increased stiffness, decreased stiffness, or normal parameters.

19. The system of any of the preceding paragraphs, wherein the biological sample is a tissue or population of cells.

20. The system of any of the preceding paragraphs, wherein the sample is viable during measuring of the stiffness.

21. The system of any of the preceding paragraphs, wherein the sample is viable during measuring and after measuring of the global radian strain.

22. A system for determining a stretch condition of a biological tissue, the system comprising:
a free-standing composite layer configured to receive a tissue sample of the biological tissue, the free-standing composite layer having a first surface, a second surface that is opposing to the first surface, and two opposing ends, the free-standing composite layer including a first layer in the form of a flexible membrane that forms a base of the free-standing composite layer,
a second layer with a tunable stiffness overlaying in a no-slip interface with the first layer, the second layer including a plurality of fiduciary markers, and
a third layer overlaying in a no-slip interface with the second layer, the third layer having an adhesive surface opposing the no-slip interface with the second layer, the adhesive surface being configured to receive with a no-slip interface the tissue sample; and
a stretching device including
an indenter having a plurality of inner points configured to contact the second surface of the free-standing composite layer, and
a rim aligned with the indenter along a central axis, the rim having a plurality of outer points configured to contact the first surface near the two opposing ends of the free-standing composite layer, the plurality of outer points being farther from the central axis than the plurality of inner points;
wherein at least one of the indenter and the rim is movable to cause an uniform equibiaxial mechanical stretch of the free-standing composite layer and the tissue sample.

23. The system of any of the preceding paragraphs, wherein the first layer consists of silicon material.

24. The system of any of the preceding paragraphs, wherein the second layer and the third layer each consists of a polydimethylsiloxane (PDMS) material.

25. The system of any of the preceding paragraphs, wherein the stretching device includes a hollow interior through which an imaging path is formed for capturing a displaced image of the plurality of fiduciary markers.

22. A system for determining a stretch condition of a biological tissue, the system comprising:
   a free-standing composite layer configured to receive a tissue sample of the biological tissue, the free-standing composite layer having a first surface, a second surface that is opposing to the first surface, and two opposing ends, the free-standing composite layer including
   a first layer in the form of a flexible membrane that forms a base of the free-standing composite layer,
   a second layer with a tunable stiffness overlaying in a no-slip interface with the first layer, the second layer including a plurality of fiduciary markers, and
   a third layer overlaying in a no-slip interface with the second layer, the third layer having an adhesive surface opposing the no-slip interface with the second layer, the adhesive surface being configured to receive with a no-slip interface the tissue sample; and
   a stretching device including
   an indenter having a plurality of inner points configured to contact the second surface of the free-standing composite layer, and
   a rim aligned with the indenter along a central axis, the rim having a plurality of outer points configured to contact the first surface near the two opposing ends of the free-standing composite layer, the plurality of outer points being farther from the central axis than the plurality of inner points;
   wherein at least one of the indenter and the rim is movable to cause an uniform equibiaxial mechanical stretch of the free-standing composite layer and the tissue sample.

23. The system of any of the preceding paragraphs, wherein the first layer consists of silicon material.

24. The system of any of the preceding paragraphs, wherein the second layer and the third layer each consists of a polydimethylsiloxane (PDMS) material.

25. The system of any of the preceding paragraphs, wherein the stretching device includes a hollow interior through which an imaging path is formed for capturing a displaced image of the plurality of fiduciary markers.

26. A method of classifying a sample, the method comprising
a) applying radial stretch to a substrate and determining a global radial strain of the substrate layer that is measured when the layer is stretched;
b) adhering the sample to the substrate; and
c) applying radial stretch the substrate having an adhered sample and determining a global radial strain of the substrate layer that is measured when the layer is stretched,
wherein measuring is done via a formula of:

$\varepsilon_{rr}^o = \Delta r_{memb}/r_{memb}^o \times 100$ wherein $\Delta r_{memb}$ denotes the change of the radius, and $r_{memb}^o$ is the stress-free radius, and the local radial strain $\varepsilon_{rr}$ that is measured when the substrate and substrate having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and
wherein samples are classified as either having increased stiffness, decreased stiffness, or normal parameters.

27. The method of any of the preceding paragraphs, wherein the sample is a biological sample.

28. The method of any of the preceding paragraphs, wherein the sample is a non-biological sample.

29. The method of any of the preceding paragraphs, wherein the biological sample is a tissue or population of cells.

30. The method of any of the preceding paragraphs, wherein the tissue is obtained from lung, eye, kidney, bladder, skin, liver, or heart.

31. The method of any of the preceding paragraphs, wherein the measuring is performed via a system of any of claims 1-25.

32. The method of any of the preceding paragraphs, wherein the sample is viable during measuring.

33. The method of any of the preceding paragraphs, wherein the sample is viable during and after measuring.

34. A method of classifying a sample, the method comprising
a) applying radial stretch to a polydimethylsiloxane (PDMS) layer and determining a global radial strain of the substrate layer that is measured when the layer is stretched;
b) adhering the sample to the PDMS layer; and
c) applying radial stretch the PDMS layer having an adhered sample and determining a global radial strain of the substrate layer that is measured when the layer is stretched,
wherein measuring is done via a formula of:

$\varepsilon_{rr}^o = \Delta r_{memb}/r_{memb}^o \times 100$ wherein $\Delta r_{memb}$ denotes the change of the radius, and $r_{memb}^o$ is the stress-free radius, and the local radial strain $\varepsilon_{rr}$ that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and
wherein samples are classified as either having increased stiffness, decreased stiffness, or normal parameters.

35. The method of any of the preceding paragraphs, wherein the PDMS layer comprises a sticky substrate and a PDMS layer with a tunable stiffness.

36. The method of any of the preceding paragraphs, wherein the sticky substrate adheres the sample to the PDMS layer.

37. The method of any of the preceding paragraphs, wherein the PDMS layer further comprises the fiducial markers.

38. The method of any of the preceding paragraphs, wherein the fiducial markers are fluorescent.

39. The method of any of the preceding paragraphs, wherein the fiducial markers are used to measure global radial strain and local radial strain.

40. The method of any of the preceding paragraphs, wherein the fiducial markers are beads, ink marks, glass nanospheres, quantum dots, micro-posts or surface patterns.

41. A method of classifying a sample, the method comprising
a) determining a global radial strain of a substrate layer that is measured when the layer is stretched without a sample using the system of any of claims 1-25;
b) adhering the sample to the to a freestanding composite layer; and
c) applying radial stretch the freestanding composite layer having an adhered sample and determining a global radial strain of the substrate layer that is measured when the layer is stretched,
wherein measuring is done via a formula of:

$\varepsilon_{rr}^o = \Delta r_{memb}/r_{memb}^o \times 100$ wherein $\Delta r_{memb}$ denotes the change of the radius, and $r_{memb}^o$ is the stress-free radius, and the local radial strain E rr that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and
wherein samples are classified as either having increased stiffness, decreased stiffness, or normal parameters.

42. A method of assessing the effect of at least one agent on classification of a sample, the method comprising
a) applying radial stretch to a substrate and determining a global radial strain of the substrate layer that is measured when the layer is stretched;
b) adhering the sample to the substrate;
c) contacting the sample with the at least one agent; and
d) applying radial stretch the substrate having an adhered sample and determining a global radial strain of the substrate layer that is measured when the layer is stretched,
wherein measuring is done via a formula of:

$\varepsilon_{rr}^o = \Delta r_{memb}/r_{memb}^o \times 100$ wherein $\Delta r_{memb}$ denotes the change of the radius, and $r_{memb}^o$ is the stress-free radius, and the local radial strain $\varepsilon_{rr}$ that is measured when the substrate and substrate having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and
wherein samples are classified as either having increased stiffness, decreased stiffness, or normal parameters.

43. A method of assessing the effect of at least one agent on classification of a sample, the method comprising
a) applying radial stretch to a polydimethylsiloxane (PDMS) layer and determining a global radial strain of the substrate layer that is measured when the layer is stretched;
b) adhering the sample to the PDMS layer;
c) contacting the sample with the at least one agent; and
d) applying radial stretch the PDMS layer having an adhered sample and determining a global radial strain of the substrate layer that is measured when the layer is stretched,
wherein measuring is done via a formula of:

$\varepsilon_{rr}^o = \Delta r_{memb}/r_{memb}^o \times 100$ wherein $\Delta r_{memb}$ denotes the change of the radius, and $r_{memb}^o$ is the stress-free radius, and the local radial strain $\varepsilon_{rr}$ that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and
wherein samples are classified as either having increased stiffness, decreased stiffness, or normal parameters.

44. A method of assessing the effect of at least one agent on classification of a sample, the method comprising
a) determining a global radial strain of a substrate layer that is measured when the layer is stretched without a sample using the system of any of claims 1-25;
b) adhering the sample to the to a freestanding composite layer;
c) contacting the sample with the at least one agent; and
d) applying radial stretch the freestanding composite layer having an adhered sample and determining a global radial strain of the substrate layer that is measured when the layer is stretched,
wherein measuring is done via a formula of:

$\varepsilon_{rr}^o = \Delta r_{memb}/r_{memb}^o \times 100$ wherein $\Delta r_{memb}$ denotes the change of the radius, and $r_{memb}^o$ is the stress-free radius, and the local radial strain $\varepsilon_{rr}$ that is measured when the PDMS layer and PDMS layer having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and wherein samples are classified as either having increased stiffness, decreased stiffness, or normal parameters.

45. The method of any of the preceding paragraphs, wherein the contacting is for a time sufficient for the at least one agent to alter the sample.
46. The method of any of the preceding paragraphs, further comprising the step of calculating a global radial stretch of the sample prior to contacting with the at least one agent.
47. The method of any of the preceding paragraphs, further comprising the step of comparing the global radial stretch of the sample contacted with at least one agent to the global radial stretch of the sample prior to contact with the at least one agent.
48. The method of any of the preceding paragraphs, wherein the change in global radial strain of a substrate that is measured without the sample adhered and the local radial strain that is measured with an adhered sample is a readout of the effect of the at least one agent on the stiffness of the sample.
49. The method of any of the preceding paragraphs, wherein the at least one agent is at least two agents, and the at least two agents contact the sample at the same time.
50. The method of any of the preceding paragraphs, wherein the at least one agent is at least two agents, and the at least two agents contact the sample at the different times.
51. The method of any of the preceding paragraphs, wherein the at least one agent is a library of agents.
52. A method of assessing the effect of at least one agent on the classification of a sample, the method comprising:
    calculating a first stiffness of the sample;
    contacting the sample with at least one agent;
    calculating a second stiffness of the sample, wherein samples are classified as either having increased stiffness, decreased stiffness, or normal parameters.
53. A method of assessing the effect of at least one agent on the classification of a sample, the method comprising
    adhering a sample to a substrate;
    applying radial stretch to the substrate;
    calculating a first stiffness of the sample,
    contacting the sample with at least one agent;
    applying radial stretch to the substrate; and
    calculating a second stiffness of the sample, wherein samples are classified as either having increased stiffness, decreased stiffness, or normal parameters.
54. A method of assessing the effect of at least one agent on the classification of a sample, the method comprising
    applying a sample to system of any of claim 1-25;
    calculating a first stiffness of the sample
    contacting the sample with at least one agent; and
    calculating a second stiffness of the sample, wherein samples are classified as either having increased stiffness, decreased stiffness, or normal parameters.
55. The method of any of the preceding paragraphs, further comprising the step of comparing the first stiffness and second stiffness.
56. The method of any of the preceding paragraphs, wherein the change in the first and second stiffness is a readout of the effect of the at least one agent on the stiffness of the sample.
57. A method of identifying a subject as having a disease or disorder associated with increased stiffness of a tissue, the method comprising:
    obtaining a sample from a subject;
    calculating a stiffness of the sample;
    comparing the stiffness the sample to a stiffness of an appropriate control sample; and
    identifying the subject as having a disease or disorder with increased stiffness of a tissue if the stiffness of the sample is greater than the stiffness of the appropriate control sample.
58. A method of identifying a subject as having a disease or disorder associated with increased stiffness of a tissue, the method comprising:
    receiving the results of an assay that calculated a stiffness of the sample obtained from a subject;
    comparing the stiffness the sample obtained from a patient to a stiffness of an appropriate control sample; and
    identifying the subject as having a disease or disorder with increased stiffness of a tissue if the stiffness of the sample obtained from a subject is greater than the stiffness of the appropriate control sample.
59. A method of identifying a subject as having a disease or disorder associated with decreased stiffness of a tissue, the method comprising:
    obtaining a sample from a subject;
    calculating a stiffness of the sample;
    comparing the stiffness the sample to a stiffness of an appropriate control sample; and
    identifying the subject as having a disease or disorder with decreased stiffness of a tissue if the stiffness of the sample is less than the stiffness of the appropriate control sample.
60. A method of identifying a subject as having a disease or disorder associated with decreased stiffness of a tissue, the method comprising:
    receiving the results of an assay that calculated a stiffness of the sample obtained from a subject;
    comparing the stiffness the sample obtained from a patient to a stiffness of an appropriate control sample; and
    identifying the subject as having a disease or disorder with decreased stiffness of a tissue if the stiffness of the sample obtained from a subject is less than the stiffness of the appropriate control sample.
61. The method of any of the preceding paragraphs, wherein the disease or disorder associated with increased stiffness of a tissue is selected from the group consisting of: pulmonary fibrosis, pulmonary hypertension, lung cancer, lung tissue following bacterial or viral infection, liver fibrosis, liver cancer, glomerulosclerosis and tubulointerstitial fibrosis in kidney, dysfunctional bladders, arteriosclerosis in heart, Scleroderma in skin.
62. The method of any of the preceding paragraphs, wherein the disease or disorder associated with decreased stiffness of a tissue is selected from the group consisting of: COPD, and in particular, emphysema, and any other non-lung disease that is affected by enzymatic damage.

EXAMPLES

Example 1

Introduction

Chronic obstructive pulmonary disease (COPD) is a public health emergency with rapidly increasing prevalence, morbidity, and mortality, and now ranked amongst the leading causes of death worldwide. A major subtype of COPD is emphysema that is characterized by aberrant mechanotransduction, remodeling of the extracellular matrix (ECM) of the lung parenchyma, reduced organ-level tissue stiffness, and hindered gas exchange. The precise mechanisms linking microscale alveolar remodeling to macroscale tissue stiffness, however, remain speculative due primarily to difficulties in obtaining reliable data. Such difficulties stem from the heterogeneity of the lung structure including numerous air sacs, thin septal walls, conducting airways, and vessels, complex shape of the lung boundaries, and cyclic mechanical interactions between the chest wall and the lung during breathing, which together limit the accessibility of the cells and ECM in the deep regions of the lung to imaging.

The pathogenesis of idiopathic pulmonary fibrosis (IPF) is still not fully understood despite decades of intense research. The lungs of patients with IPF invariably show characteristic features such as stiff lung tissue and peripheral honeycombing that can be seen on computed tomography imaging. These altered tissue properties play critical roles in how lung cells behave and hence carry information about the factors that drive the inexorable progression of IPF. Furthermore, it appears more and more likely that increased stiffness is not only a physiological endpoint, but it feeds back to driving disease progression by a process called mechanotransduction, the conversion of mechanical signals and stimuli to chemical information. Indeed, the local stiffness of the extracellular matrix of the lung is known to influence fibroblast activation and subsequent deposition and cross-linking of collagen, which increase tissue stiffness in a positive feedback loop. Thus, studying the cellular and molecular mechanisms of pulmonary fibrosis requires understanding how cells turn a healthy tissue with normal stiffness to a fibrotic tissue with high stiffness as a result of the local interactions between cells responsible for depositing collagen and the cellular consequences of the stiff tissue. This, in turn, also requires monitoring local tissue stiffness.

Physiologic maintenance of tissues is a basic process by which cells assess local mechanical and biochemical properties of the extracellular matrix and attempt to repair damage. During this ongoing process, cells secrete various enzymes which locally digest and eliminate components of the matrix. Subsequently, cells also produce and deposit matrix molecules such as collagens and proteoglycans to patch any damage. The response of cells to an injury is similar but often aided by inflammatory cells and their cytokines. In the laboratory, it is customary to test the effectiveness of maintenance as well as to generate damage as a model of disease with externally applied enzymes. Using digestive enzymes such as collagenases or elastases results in cleaving certain extracellular matrix components which in turn reduces the stiffness. This method can then be applied to test the sensitivity and specificity of stiffness measuring systems.

Much of our current knowledge on lung stiffness and its biological consequences have been inferred from global measurements in intact respiratory systems, or direct measurements in excised whole lungs or tissue strips with alveoli preserved. A notable exception is the microscopic stiffness measurement obtained via atomic force microscopy (AFM) applied to lung strips attached to a stretchable membrane chip. However, this technique is limited to tiny regions of ultrathin lung sections (~20 μm) that does not adequately preserve the native shape of single alveoli. Another approach is to fit a nonlinear model to the stress-strain curve of lung tissue strips during uniaxial deformation (12). This analytical approach, however, neglects the heterogeneous 3D structure and deformation of the lung parenchyma.

Described herein is a multiscale approach to measure lung tissue stiffness. Using this approach found that the IPF human PCLS is approximately twice as stiff whereas the emphysematous human PCLS is ~50% softer than the healthy PCLS. The computational modeling revealed that the softening in emphysematous PCLS is associated with septal wall weakening and structural breakdown. Thus, unveiled herein, for the first time, a mechanistic link between macroscopic lung softening, structural deterioration, and loss of function due to reduced stiffness at the level of single septal walls in human emphysema. The inventors interpret these results with protein expression profiling which brings into focus possible molecular targets for future therapeutic interventions. Finally, the inventors validated the sensitivity and specificity of stiffness measuring systems by measuring an approximately 50% decrease of stiffness of healthy mouse PCLS that was induced by applying a digestive agent, collagenase.

Results

Concept of Stiffness Measurement

Figure 17A:
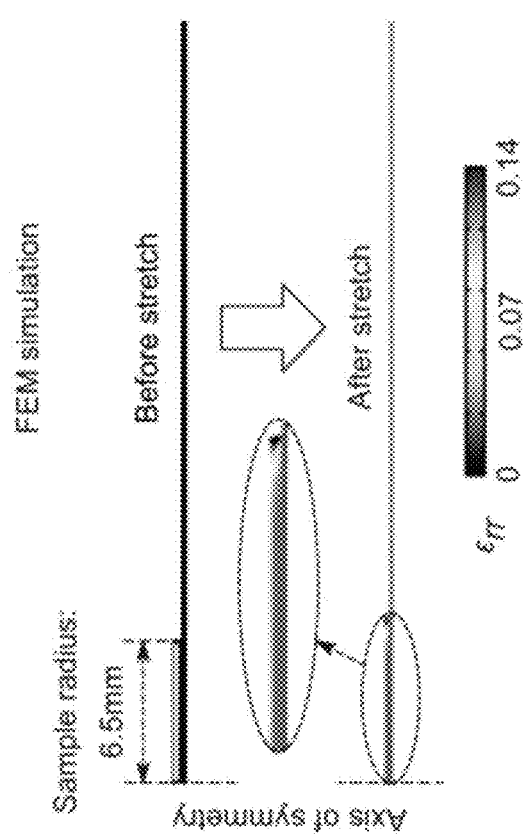
FIGS. 17A-17E shows simulation and measurement of stiffness.
Figure 17B:
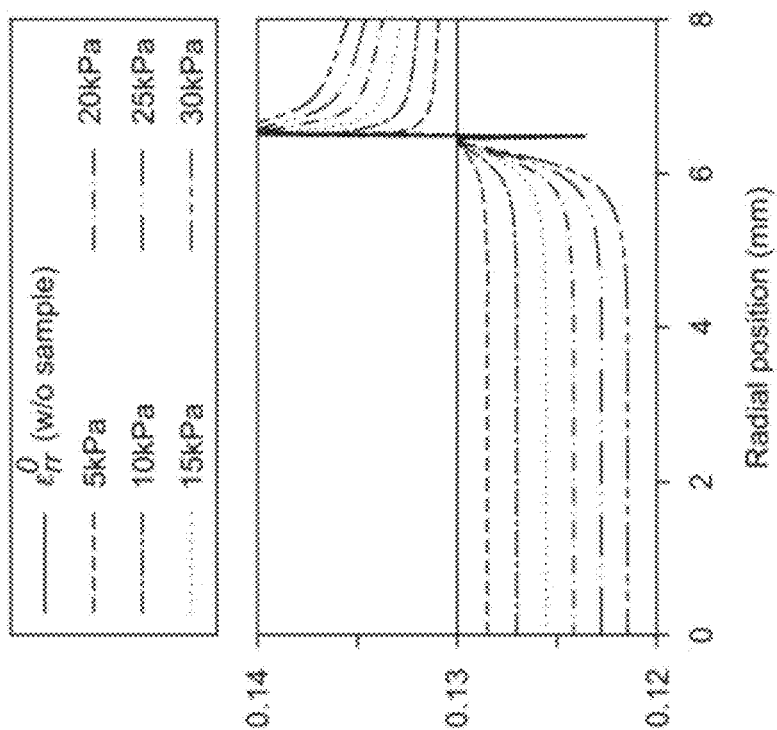
Figure 17C:
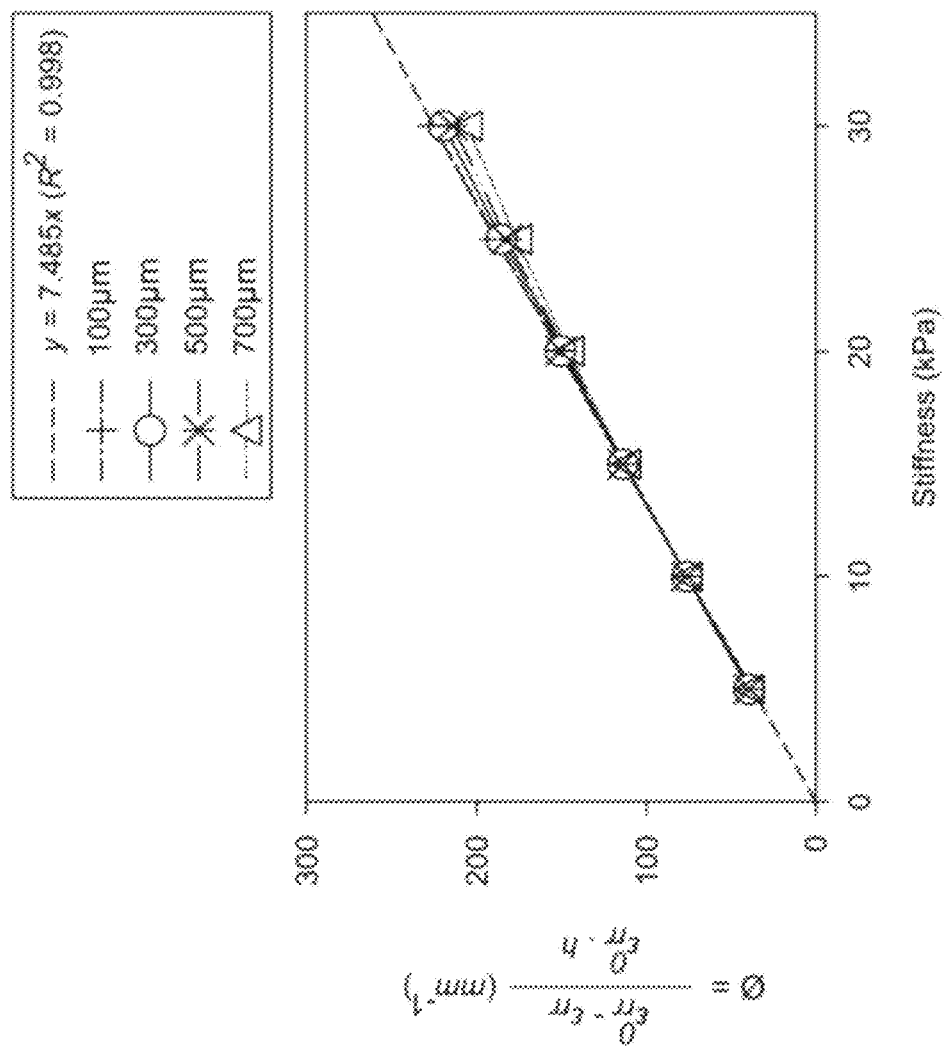
Figure 21B:
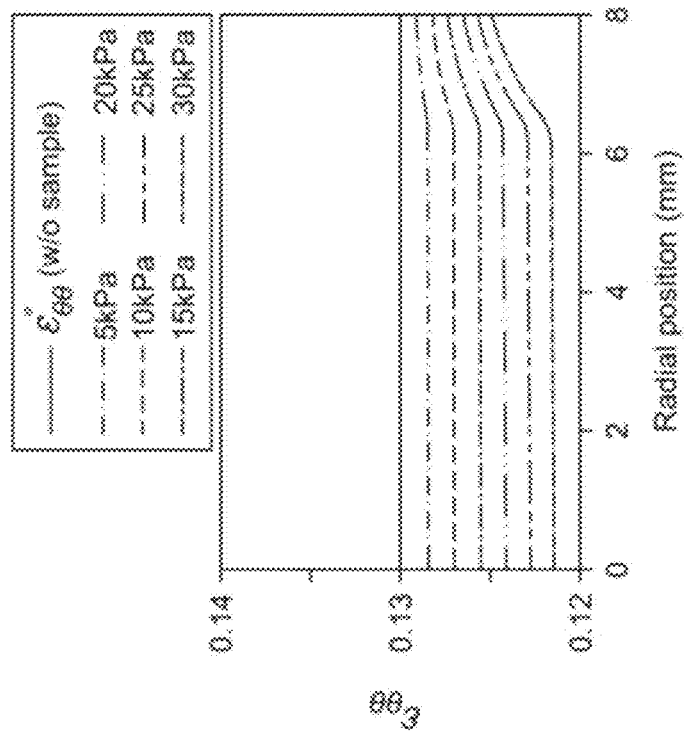
FIGS. 21A and 21B show FE modeling confirming that the imposed stretch is equi-biaxial.
Figure 21A:
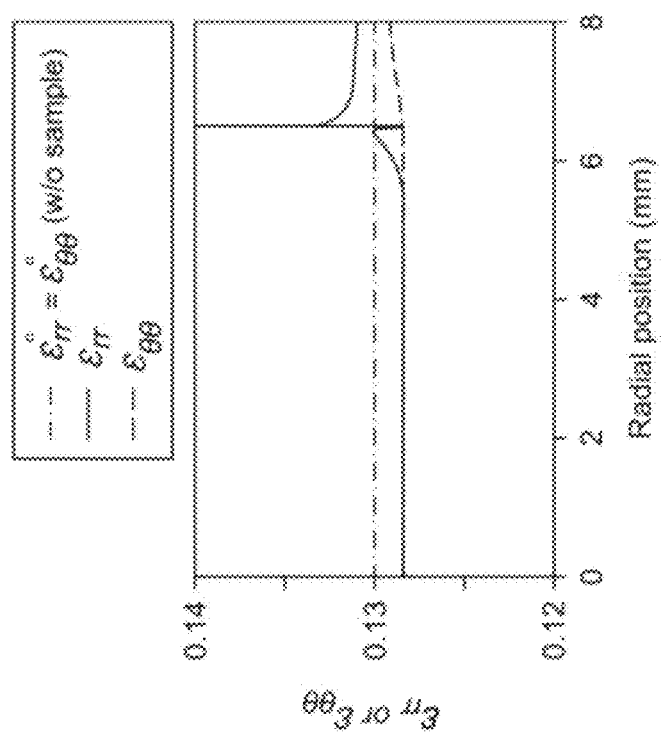
Figure 22B:
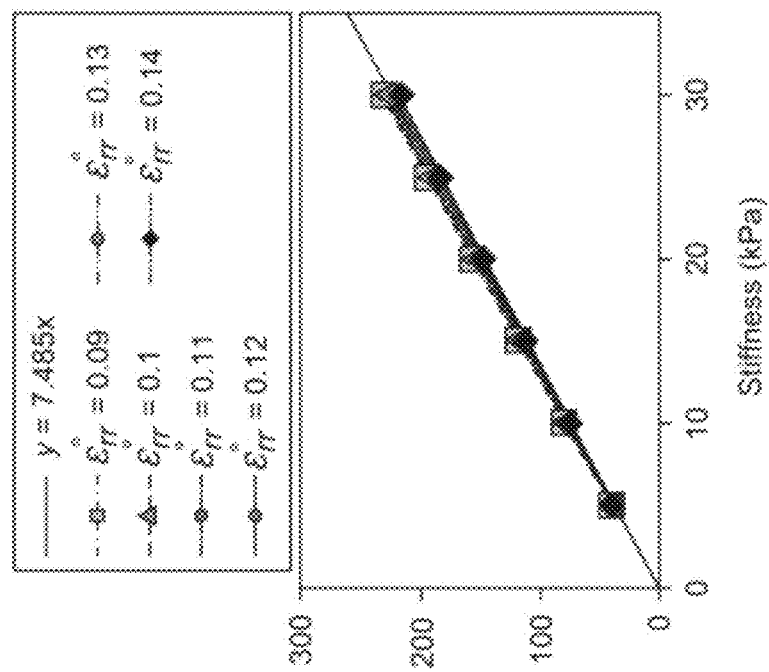
FIGS. 22A and 22B show radial strains measured in the FE model.
Figure 22A:
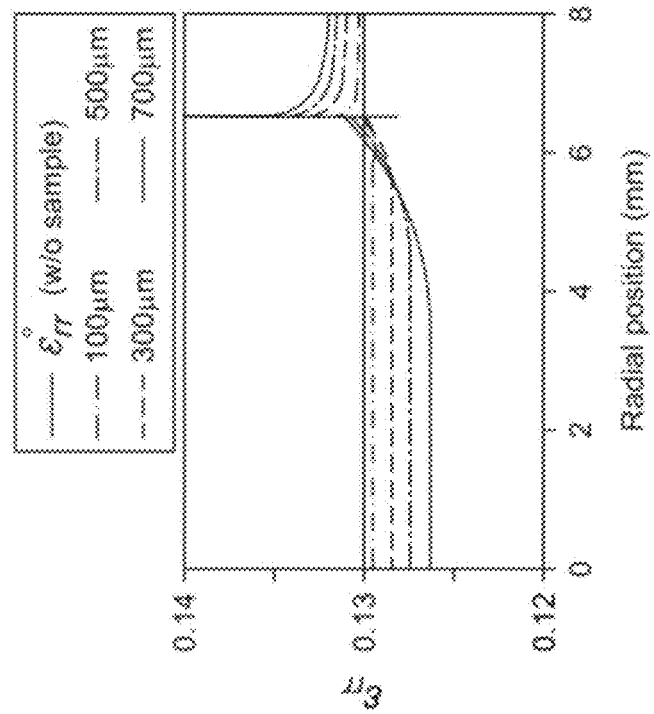

To establish the foundations for stiffness measurement, the inventors first developed an axisymmetric finite element (FE) model in which a thin elastic sample with a range of stiffness and thickness values is attached to and radially stretched by a membrane (FIG. 17A). The inventors assumed that both the membrane and the sample follow linearly elastic behavior with a no-slip condition at their interface (Materials and Methods). When the membrane was radially stretched, the global radial strain of the membrane was given by:

$$\varepsilon_{rr}^{o} = \Delta r_{memb}/r_{memb}^{o} \times 100 \tag{1}$$

where $\Delta r_{memb}$ denotes the change of the radius, and $r_{memb}^{o}$ is the stress-free radius. Following a stretch of the membrane without a sample to $\varepsilon_{rr}^{o}=13\%$, the local radial strain $\varepsilon_{rr}$ computed as the gradient of radial displacement at the top surface of the membrane was equal to the global strain $\varepsilon_{rr}^{o}$ over all radial positions, which is expected for the case of a uniform equibiaxial mechanical stretch applied to a homogeneous membrane (black line in FIG. 17B). However, when a sample was attached to the membrane, imposing the same global strain resulted in a non-homogeneous strain field at the interface between the sample and the membrane (FIGS. 17B, 21A and 21B). Specifically, the local strain was smaller than $\varepsilon_{rr}^{o}$ in the region under the sample (<6.5 mm), but larger than $\varepsilon_{rr}^{o}$ outside the sample region (>6.5 mm). Moreover, $\varepsilon_{rr}$ within the sample region was nearly constant up to ~3 mm of radial position regardless of sample stiffness or thickness (FIGS. 17B and 21A). The difference between $\varepsilon_{rr}^{o}$ and $\varepsilon_{rr}$ systematically increased with both the stiffness and thickness of the sample. When the inventors normalized the relative change in radial strain by the thickness h of the sample:

$$\phi = \frac{\varepsilon_{rr}^{0} - \varepsilon_{rr}}{\varepsilon_{rr}^{0} h} \tag{2}$$

the inventors found a single linear relationship between the $\phi$ and sample stiffness for all values of h (FIG. 17C). A linear regression over all cases provided thus a robust relationship between $\phi$ and stiffnesses (dashed black line in FIG. 17C; $r^2=0.999$):

$$\phi = AE \tag{3}$$

wherein A is a constant from the linear regression and E is the global stiffness of a sample. Furthermore, this relationship did not depend on the magnitude of the global strain $\varepsilon_{rr}^o$ applied to the membrane-sample system (FIG. 22B). This linear relationship established the basis for estimating the stiffness of an arbitrary sample by measuring strains near the center of a sample (radial position <3 mm) while the membrane-sample system is stretched equibiaxially.

A Novel Device to Deliver Equibiaxial Stretch

Figure 17D:
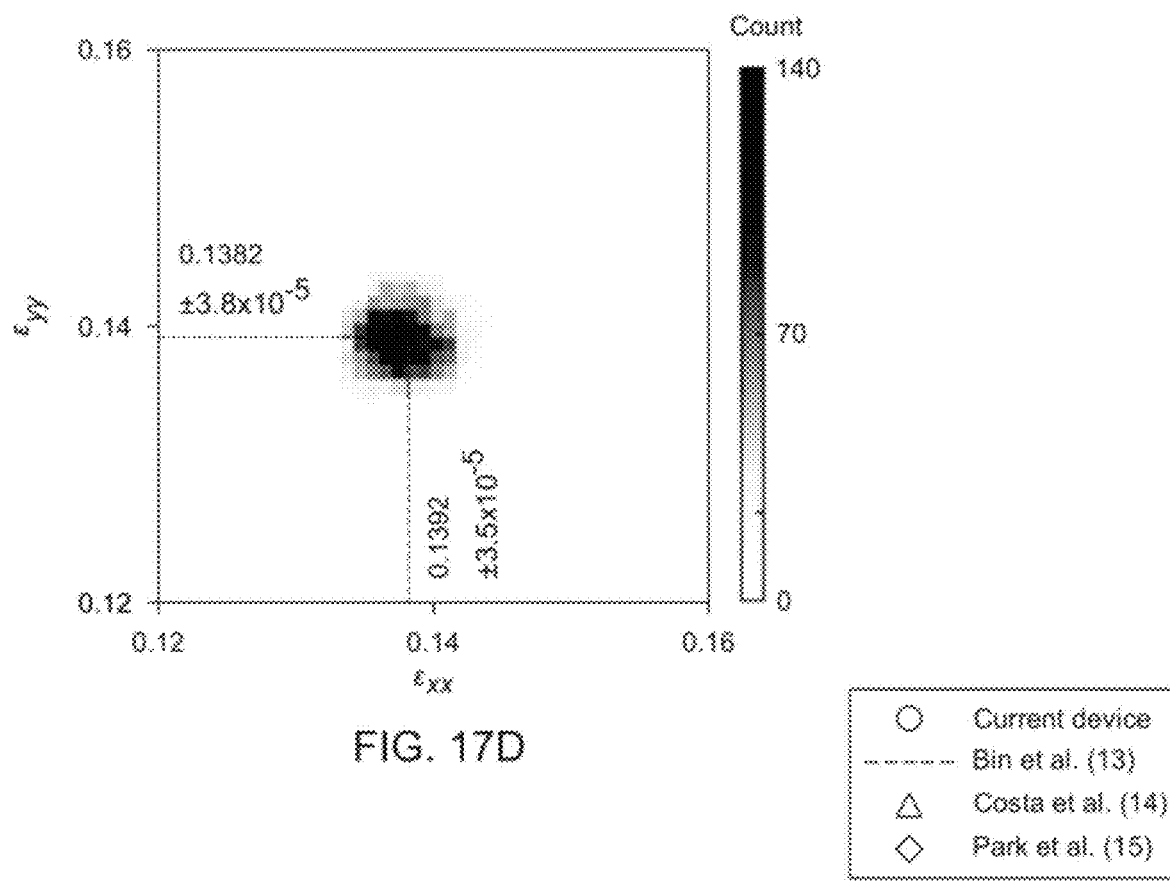

The inventors implemented the concept of stiffness measurements by building a prototype device, which applies equibiaxial mechanical stretch to a membrane holding a sheet-like sample while simultaneously mapping the spatial distribution of displacements and strains underneath the sample (FIGS. 1 and 17D). This is enabled by a custom-designed elastic composite substrate consisting of a stiff silicon membrane coated with a layer of soft polydimethylsiloxane (PDMS) gel (NuSil® Silicone Technologies, Carpinteria, CA) with fluorescent beads embedded at the top surface (FIG. 2). Using an inverted microscope, the device allows imaging the fluorescent beads at the interface between the bottom of the sample and the membrane composite during stretch from below (FIG. 1). In this manner, the composite acts as a displacement sensor.

FIG. 3A-3C depicts a representative 0.9×0.9 mm² displacement map acquired near the center of the membrane while being biaxially stretched. Circular patterns in the displacement map and overlaid vectors (white) indicated that the displacements are radially symmetric. For additional clarity, the inventors compiled FIG. 17D that depicts a histogram of normal strain components, $\varepsilon_{xx}$ and $\varepsilon_{yy}$, computed from every pixel in the displacement map in FIG. 3A-3C. The mean and the standard error (SE) of $\varepsilon_{xx}$ and $\varepsilon_{yy}$ are $0.1383 \pm 3.8 \cdot 10^{-5}$ and $0.1392 \pm 3.9 \cdot 10^{-5}$, respectively. The narrow distributions (FIG. 17D) and nearly identical mean values of normal strain components ($\varepsilon_{xx}/\varepsilon_{yy}=0.9928$) confirmed that the device delivers an equibiaxial mechanical stretch.

Validation of Stiffness Measurement

Figure 17E:
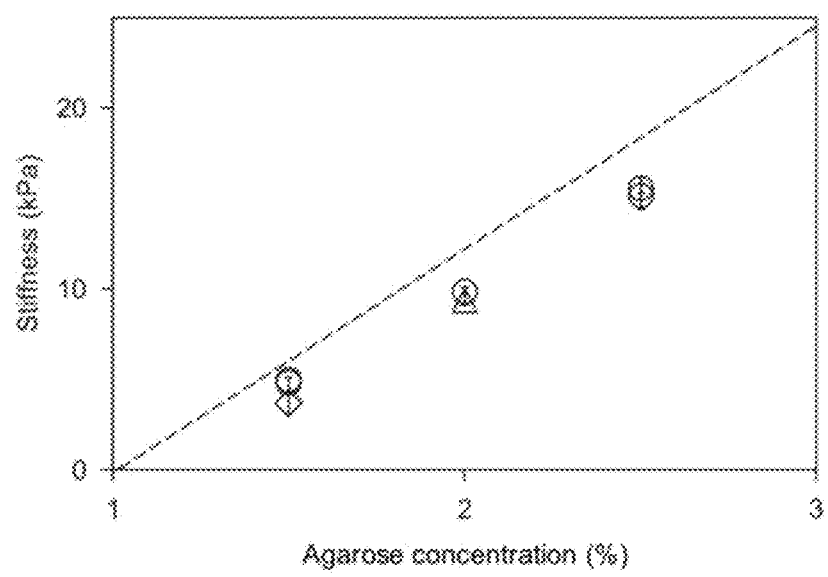

To validate the theoretically predicted relationship between φ and sample stiffnesses, the inventors utilized agarose samples with three different concentrations, 1.5%, 2.0% and 2.5%. Each agarose sample was approximately 6.5 mm in radius and 250~750 μm thick when measured using confocal microscopy. Two agarose samples were considered per concentration. Sample stiffness was determined by imposing a global stretch of approximately 13.9% applied to the membrane (FIG. 23). Agarose stiffness progressively increased with increasing concentration (FIG. 17E). The Young's modulus was 4.93±0.1 kPa (mean±SD), 9.84±0.01 kPa and 15.34±0.17 kPa for agarose concentration of 1.5%, 2.0%, and 2.5%, respectively (FIG. 17E). These moduli values agreed well with the experimental relationships between agarose concentration and stiffness previously obtained in unconfined compression tests (13) (dashed line in FIG. 17E), and were close to or slightly higher than those previously measured using AFM (green and purple markers; 3.7±0.6 kPa for 1.5% (14) and 9.3±0.23 kPa for 2.0% (15)).

Figures 24C, 25:
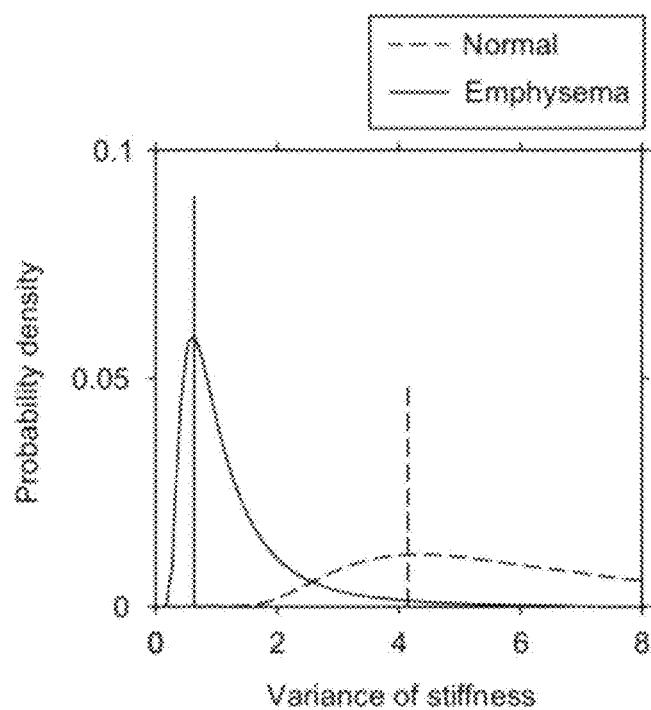
Figure 27C:
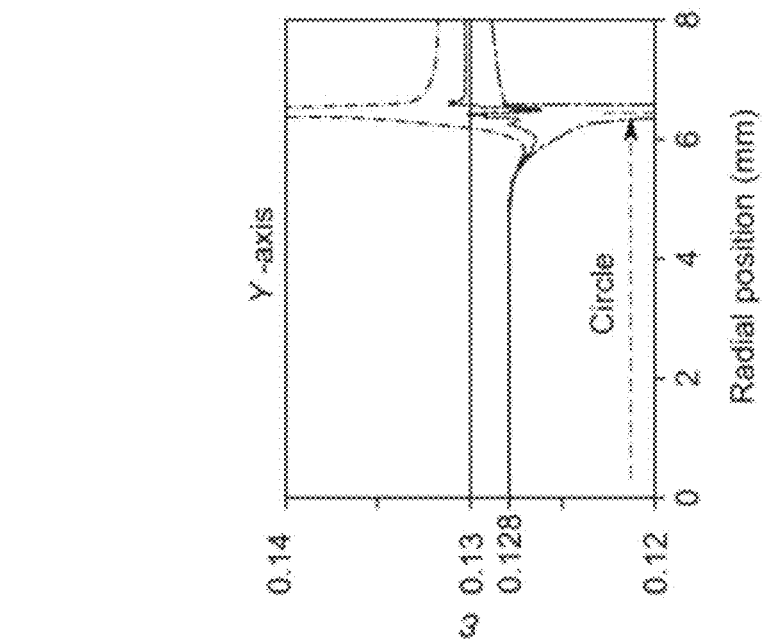
FIGS. 27A-27I show FE modeling in 3D. The 3D FE modeling confirms that the measured average strain $(\varepsilon_{xx}+\varepsilon_{yy})/2$ is not sensitive to sample shape or sample alignment relative to a membrane.
Figure 27B:
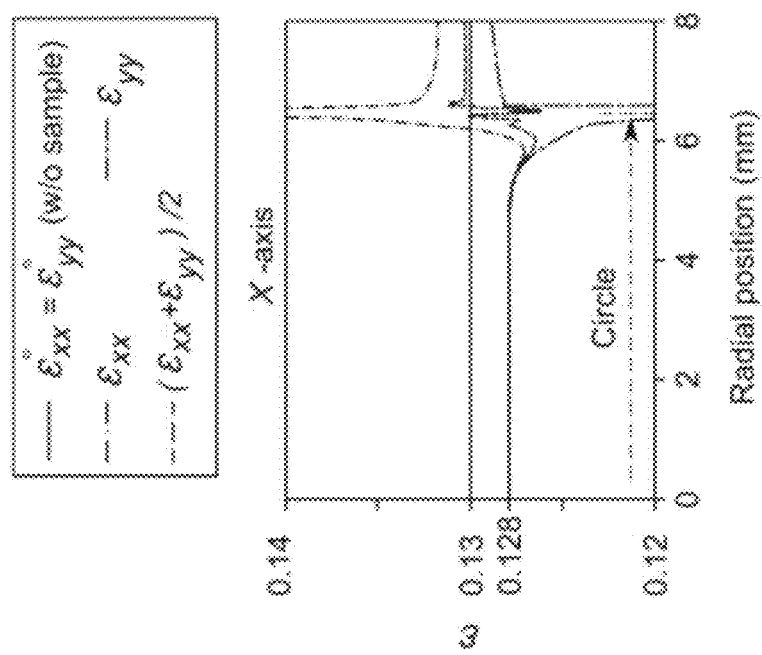
Figure 27A:
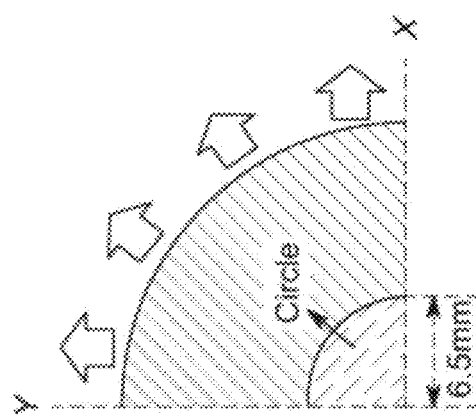
Figure 27E:
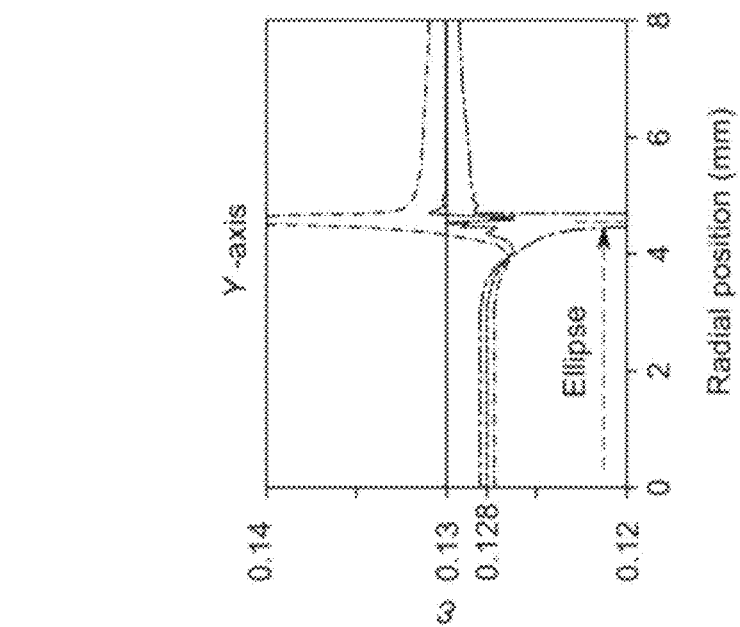
Figure 27F:
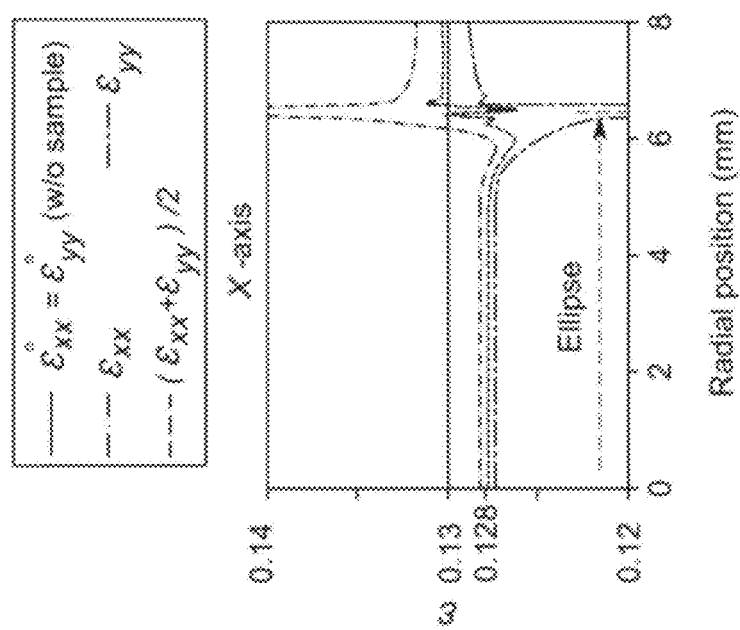
Figure 27D:
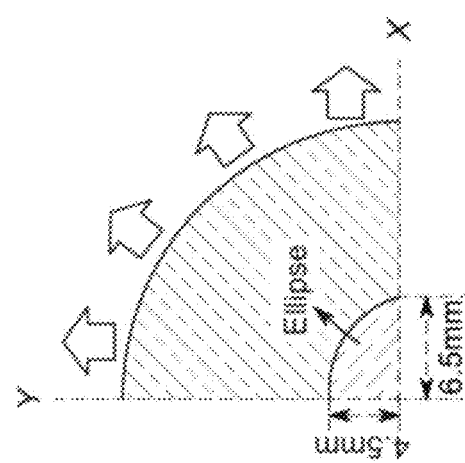
Figure 27G:
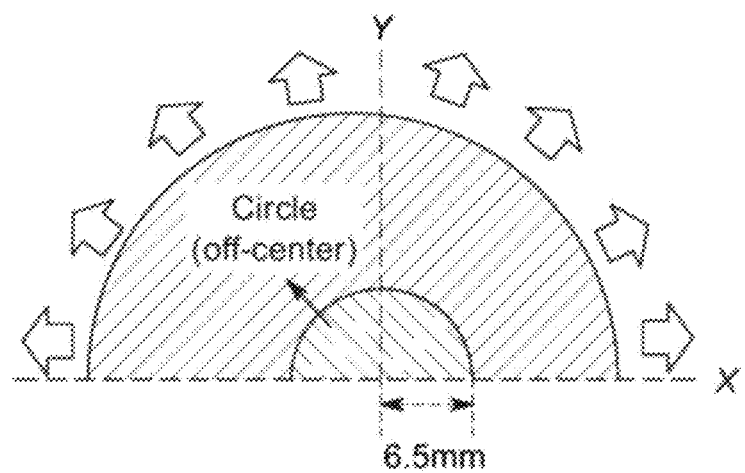
Figure 27H:
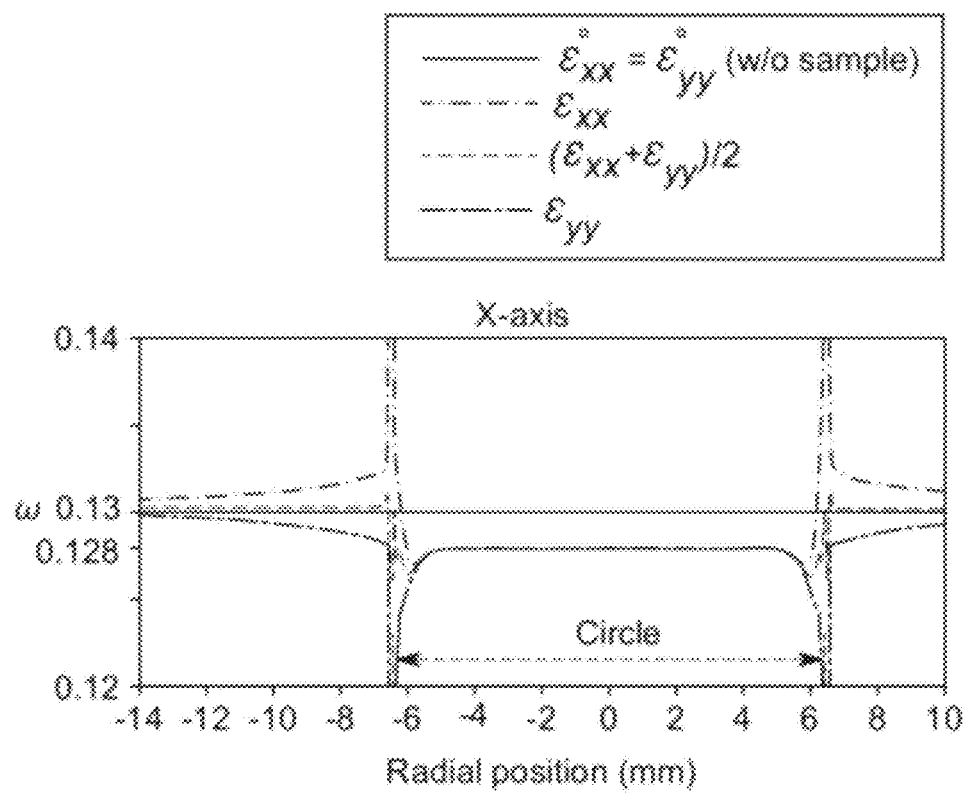

To further validate the applicability of our device to heterogeneous samples, the inventors fabricated porous and non-porous PDMS samples and measured their stiffnesses. In addition to stiffness, these measurements also provided a map of the spatial distribution of strains which is related to the structural heterogeneity of the sample. A representative map of the average strain ($\varepsilon_{xx}+\varepsilon_{yy}$)/2 of a porous PDMS sample depicted local strain 'hotspots' that correspond to pores trapped within the sample (arrows in FIG. 24A) that are clearly visible in the phase-contrast image (arrows in FIG. 24B). The Young's modulus was 2.66±0.13 kPa (mean±SD) and 3.28±0.11 kPa for the porous and non-porous PDMS, respectively (FIG. 24C). These values agreed well with measurements independently obtained using a uniaxial stretch device (2.63±0.04 kPa and 3.05±0.03 kPa for the porous and non-porous PDMS, respectively). Porous PDMS samples were softer than non-porous samples in both measurements (14% for the current device and 18% for the uniaxial stretcher device).

Stiffness of Mouse PCLS

Figure 18D:
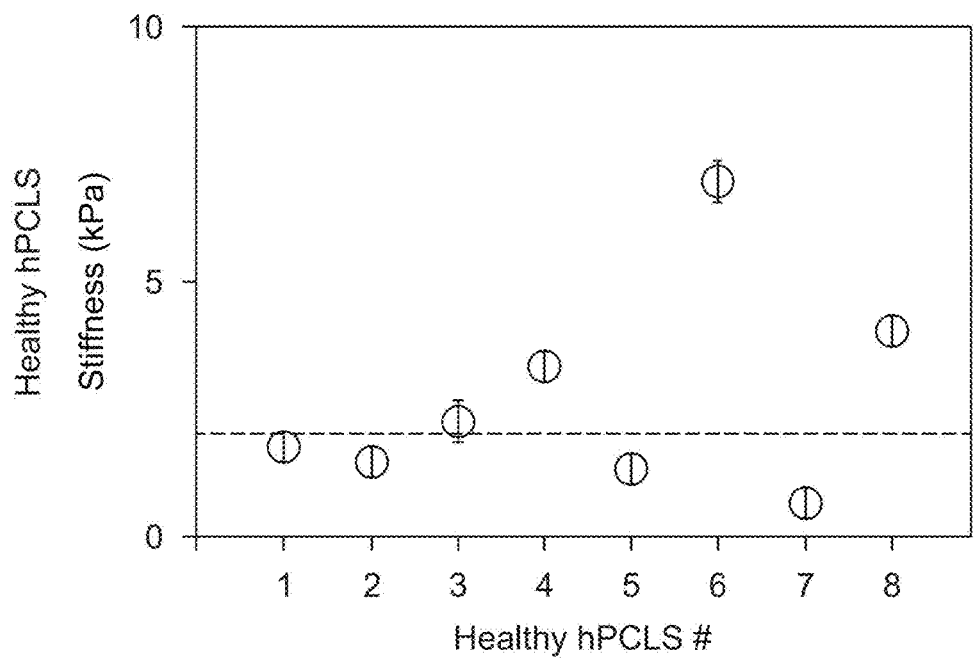
Figure 18E:
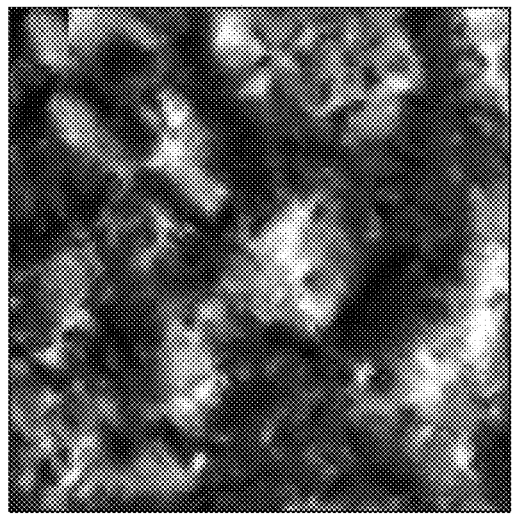
Figure 18F:
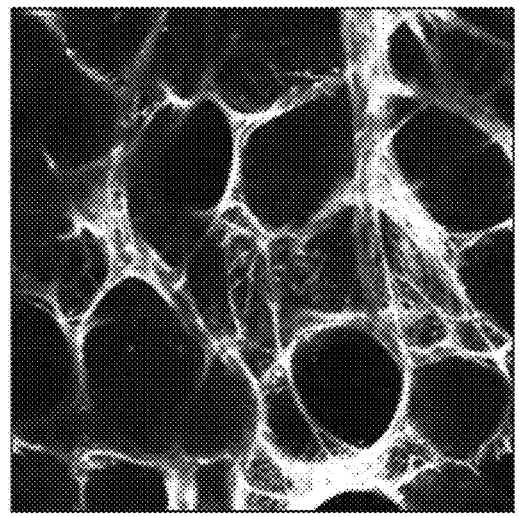
Figure 18G:
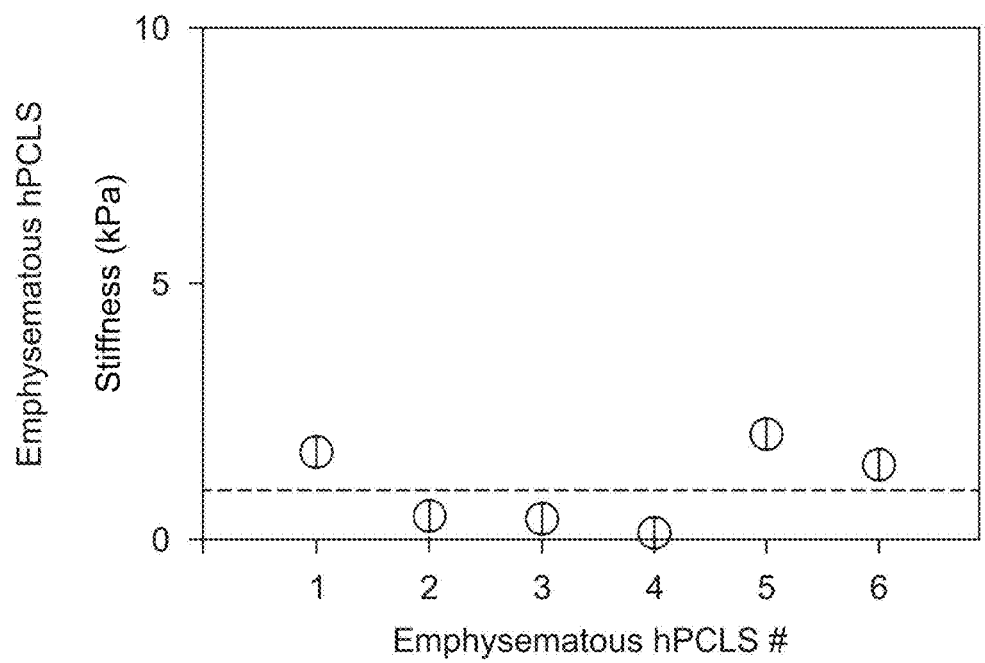
Figure 18H:
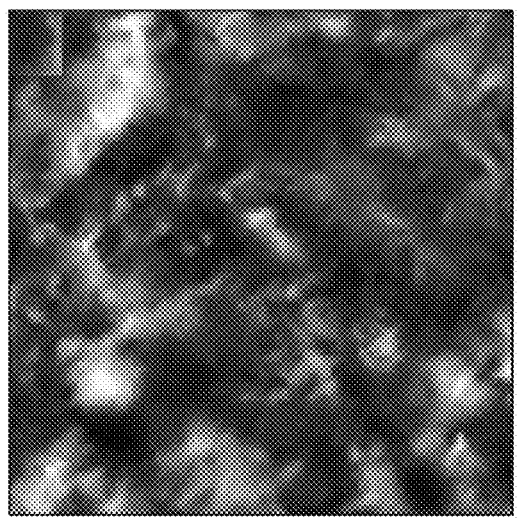
Figure 18I:
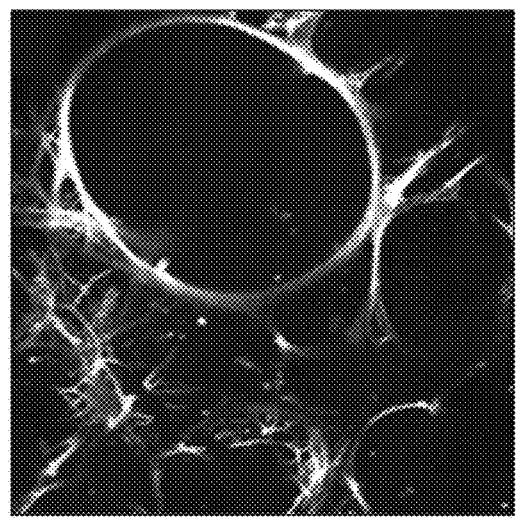

The ability to measure the stiffness of biological tissues was tested in 8 mPCLS samples acquired from C57BL/6J wild type mice (16). Their stiffness values ranged from 3 to 6 kPa (median=3.91 kPa) (FIG. 18A). A representative map of the average strain ($\varepsilon_{xx}+\varepsilon_{yy}$)/2 depicted strain heterogeneities with size scales extending below 100 μm in a mPCLS sample (dark spots in FIG. 18B). Although the median stiffness of mPCLSs was close to that of the agarose samples (median=4.93 kPa), the presence of dark spots in the strain map indicated that the strains are more heterogeneous in the mPCLS than in the agarose samples (FIG. 23). Indeed, the F-test revealed a 10 times greater variability of strains for the mPCLSs (P<0.00001). These results indicated that the strain heterogeneity seen in the mPCLSs is related to the structure of the lung parenchyma. A representative image of autofluorescence from an mPCLS sample in FIG. 18C depicted 50~100 μm sized alveolar structures that is consistent with measurements reported previously (17-19). To quantify the spatial correlations in strain and structure, the inventors computed the spatial autocorrelation function C(r) as a function of the distance (r) between two points both from the strain maps and autofluorescence images (20). In each case (FIGS. 18K and 18L), C(r) decays over a hundred micrometers. The characteristic length ρ at which C(ρ)=0.5 is 22±10 μm in strain maps and 13±1 μm in autofluorescence images, respectively, confirming the close association between strain and structural heterogeneity.

Comparison of Stiffnesses of Human Healthy and Emphysematous PCLS

Figure 18J:
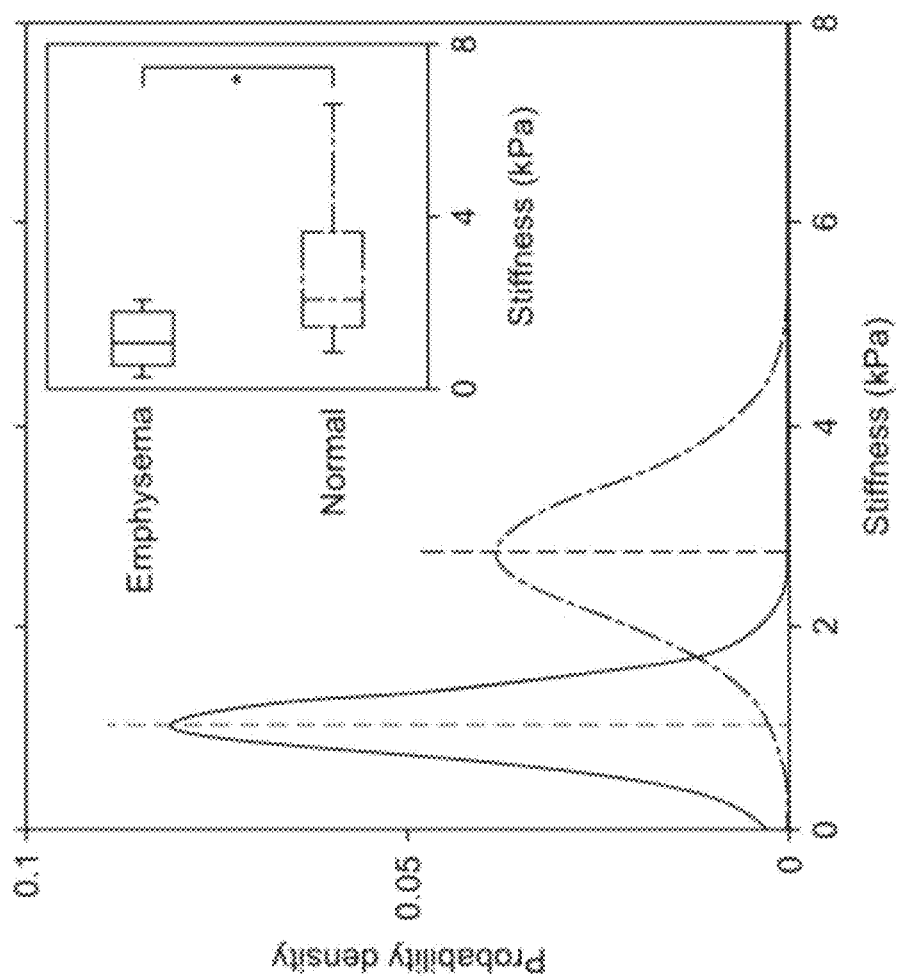
Figure 18L:
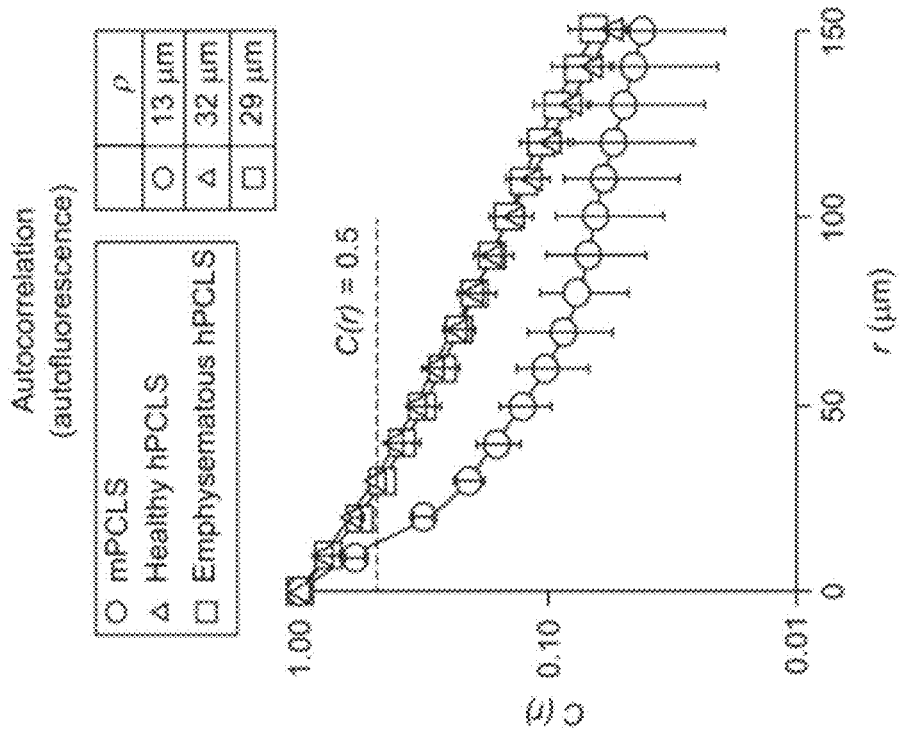
Figure 18K:
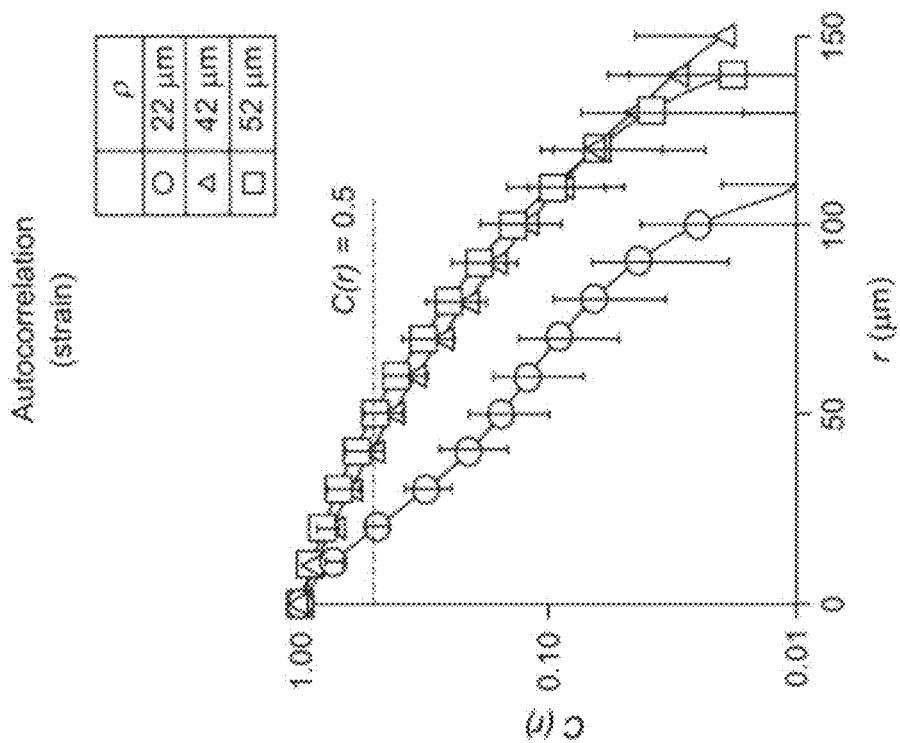

To test whether the approach can detect disease-related stiffness changes, the inventors compared 8 human PCLS (hPCLS) samples acquired from a healthy donor with 6 hPCLSs obtained from a donor with severe chronic obstructive pulmonary disease (COPD). The stiffness of healthy hPCLSs ranged from 1 to 7 kPa (median=2.28 kPa) (FIG. 18D), while the emphysematous hPCLS ranged from to 2 kPa (median=0.96 kPa) (FIG. 18G), which were statistically different from those of the healthy hPCLS (ANOVA, p=0.012). Individually, the stiffness of emphysematous hPCLS was approximately half of that of the healthy hPCLS (one-tailed t-test, p=0.026) (Inset in FIG. 18J). To further compare the stiffness of healthy and emphysematous hPCLSs, the inventors performed a Bayesian analysis of the mean stiffness (FIG. 18J) and its variance (FIG. 25). The posterior distributions in FIG. 18J showed little overlap between them with a one-sided Bayesian factor of 2.54.

Autofluorescence images showed that the emphysematous sample (FIG. 18I) exhibited visually larger air spaces than the control sample (FIG. 18F) with air space sizes of ~200 μm, as previously reported (21). Unexpectedly, however, C(r) of autofluorescence was not different between healthy and emphysematous hPCLSs (FIG. 18L; ρ=32±6 μm and 29±11 μm for healthy and emphysematous hPCLS, respectively; two tailed t-test, p=0.6). Moreover, C(r) of strain decayed similarly for both healthy and emphysematous hPCLS (FIG. 18K; p of strains: 42±8 µm for healthy hPCLS and 52±15 µm for emphysematous hPCLS; two tailed t-test, p=0.19).

Comparison of Stiffnesses of Human Healthy and IPF PCLS

To further test whether the approach can detect disease-related stiffness changes, the inventors compared 5 human PCLS (hPCLS) samples acquired from a healthy donor with 4 hPCLSs obtained from a donor with idiopathic pulmonary fibrosis (IPF). The stiffness of healthy hPCLSs ranged from 0.5 to 2.8 kPa (median=2.2 kPa), while that of the IPF hPCLS ranged from 2.6 to 6.9 kPa (median=4.44 kPa) (FIG. 39A), and the difference between the means was statistically significant (one-tailed t-test, p<0.01). To further compare the stiffness of healthy and IPF hPCLSs, the inventors performed a Bayesian analysis of the mean stiffness and its variance. The posterior distributions showed little overlap between them with a one-sided Bayesian factor of 6.72 (FIG. 39B).

Network Modeling to Estimate Local Alveolar Stiffness

Figure 19A:
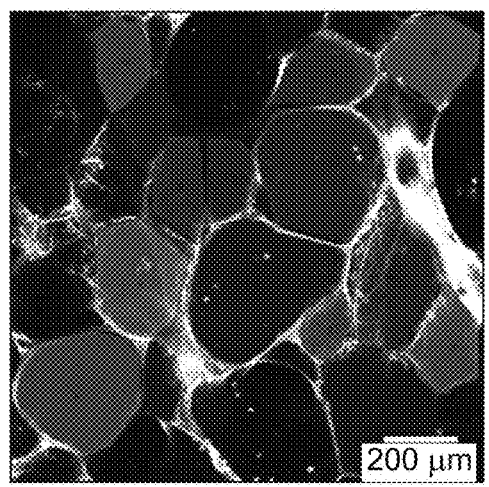
FIGS. 19A-19E show network Modeling and Stiffness Estimation of hPCLS.
Figure 19B:
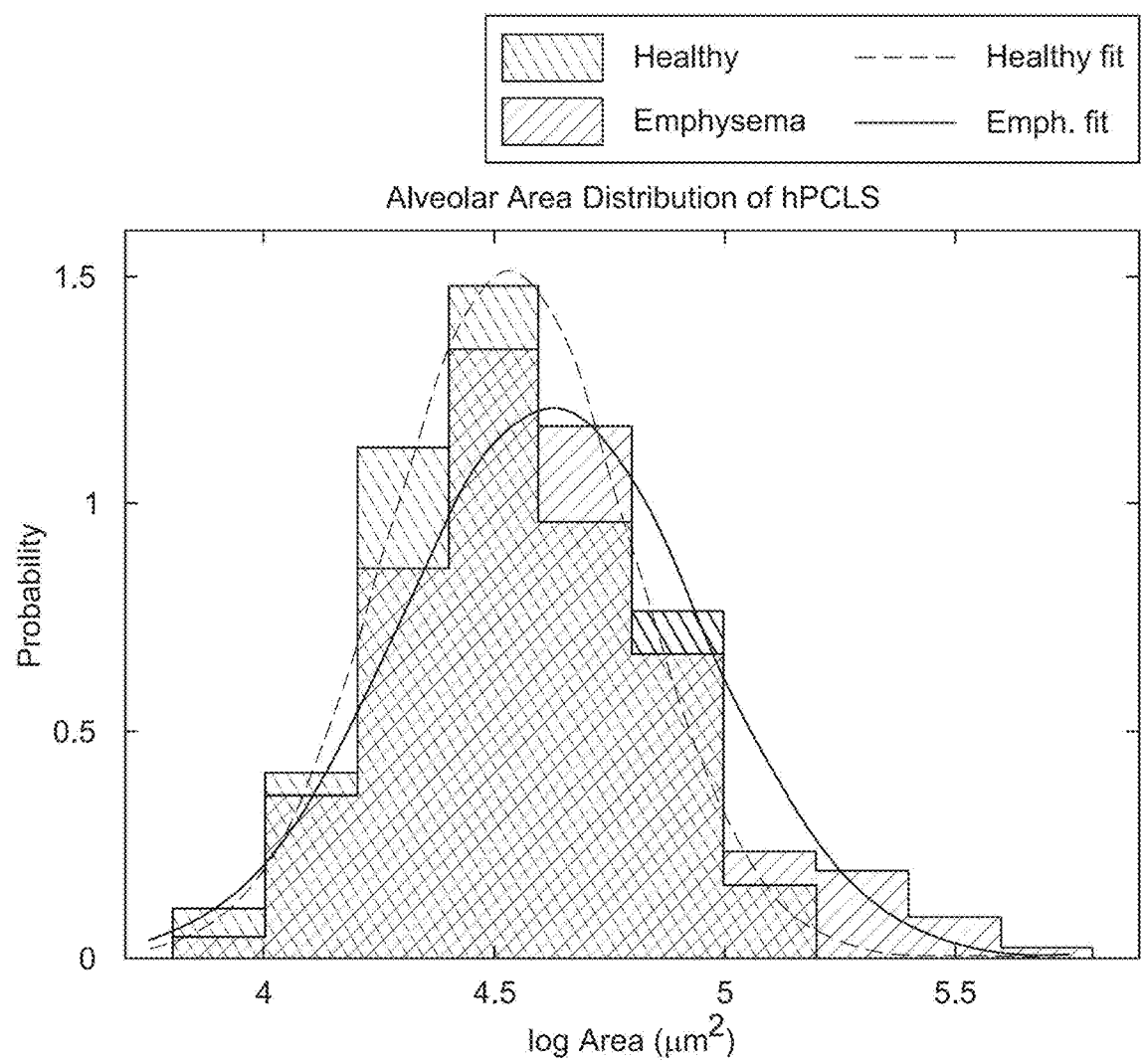
Figure 19C:
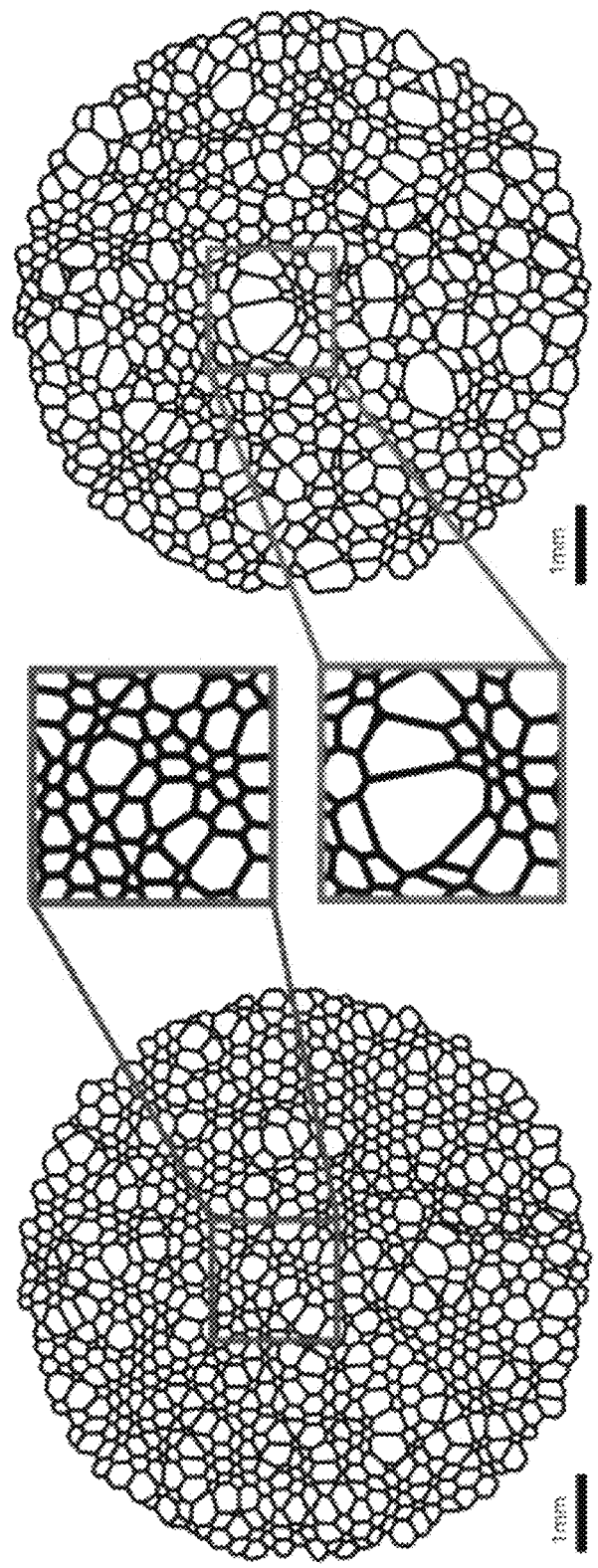
Figure 19E:
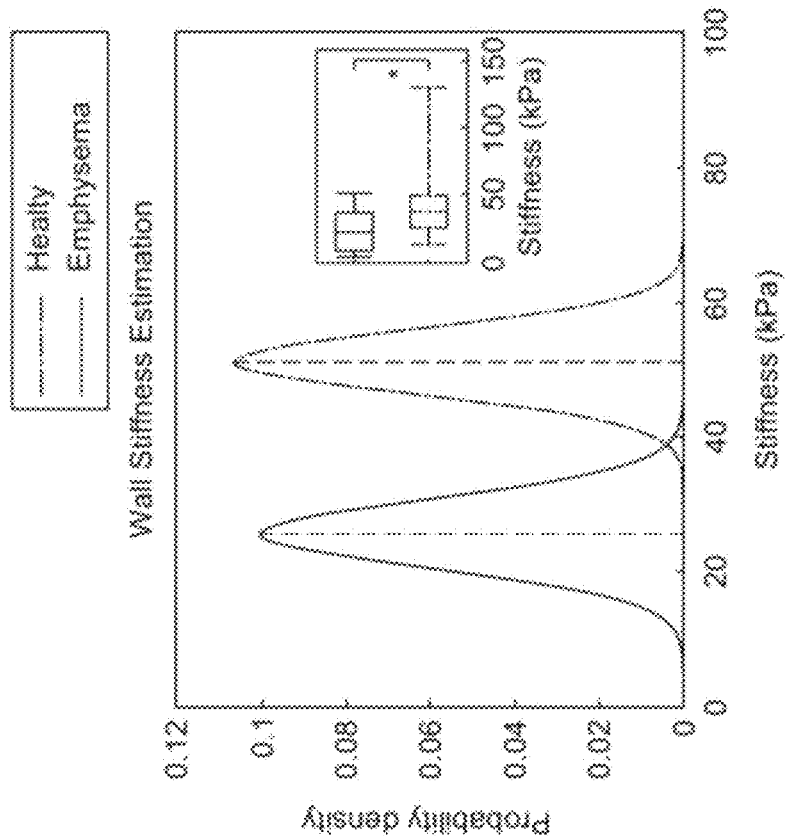
Figure 19D:
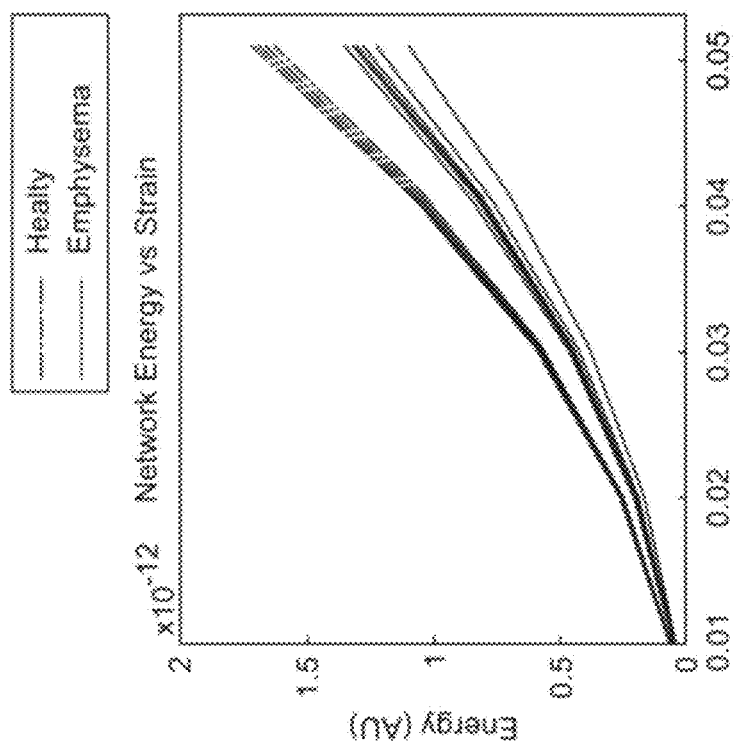

The macroscopic stiffness of the PCLS depends on the constitutive properties of alveolar walls as well as the sizes of the alveoli. To estimate the average stiffness at a lower scale, namely, that of the alveolar septal walls, the size distribution of airspaces needs to be considered. Hence, the inventors first analyzed the structure on both unfixed fluorescent (FIGS. 18F and 18I) and fixed histologic sections (FIGS. 32A-32D). A total of 183 and 209 alveoli were captured from the autofluorescent images (FIG. 19A) of healthy and emphysematous tissue, respectively. The area distributions of the healthy alveoli and the emphysematous alveoli (FIG. 19B) were found to be significantly different (one-tailed Kolmogorov-Smirnov test, p<0.05). Specifically, the emphysematous tissue alone displayed the likelihood of containing very large alveoli (far right of distribution curve). The equivalent alveolar diameters in the emphysematous tissue (249±109 µm) were also significantly larger (p<0.05) than in the healthy tissue (218±67 lam). The wall thicknesses, with fixation shrinkage included, were 5.83 µm for the healthy tissue and 5.17 µm for the emphysematous tissue, which were significantly different (p<0.05). Next, a set of network models with an area distribution identical to that of the healthy tissue were created, from which emphysematous networks were obtained by cutting springs (FIG. 19C). It was found that the average number of springs that had to be cut from the healthy network to obtain the emphysematous network was 6.9%±1.9%. Overall, ten network pairs were created and tested. The elastic energy of the network pairs was computed as a function of strain on the entire network (FIG. 19D) which allowed us to estimate the Young's modulus of each network. The mean septal wall stiffness for the healthy tissue was 51.2 kPa, and for the emphysematous tissue 25.7 kPa. Although this difference did not reach statistically significance (p=0.08, Bayesian factor: 1.65) due to the large variability of individual values, a Bayesian analysis yielded posterior stiffness distributions with little overlap between the healthy and emphysematous cases (FIG. 19E).

Enzyme Expressions and Tissue Deterioration in Emphysema

Figure 20A:
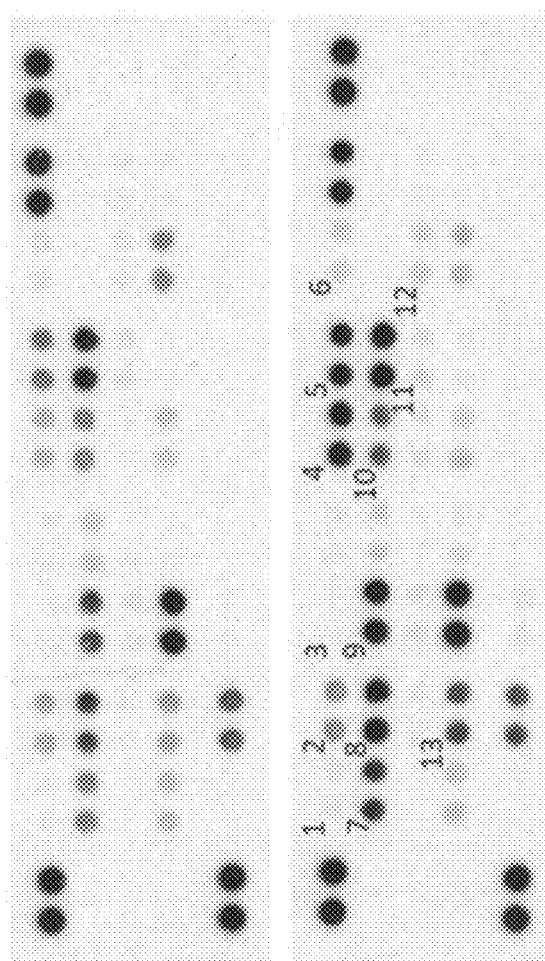
FIGS. 20A-20C show enzyme expressions in hPCLS.
Figure 20B:
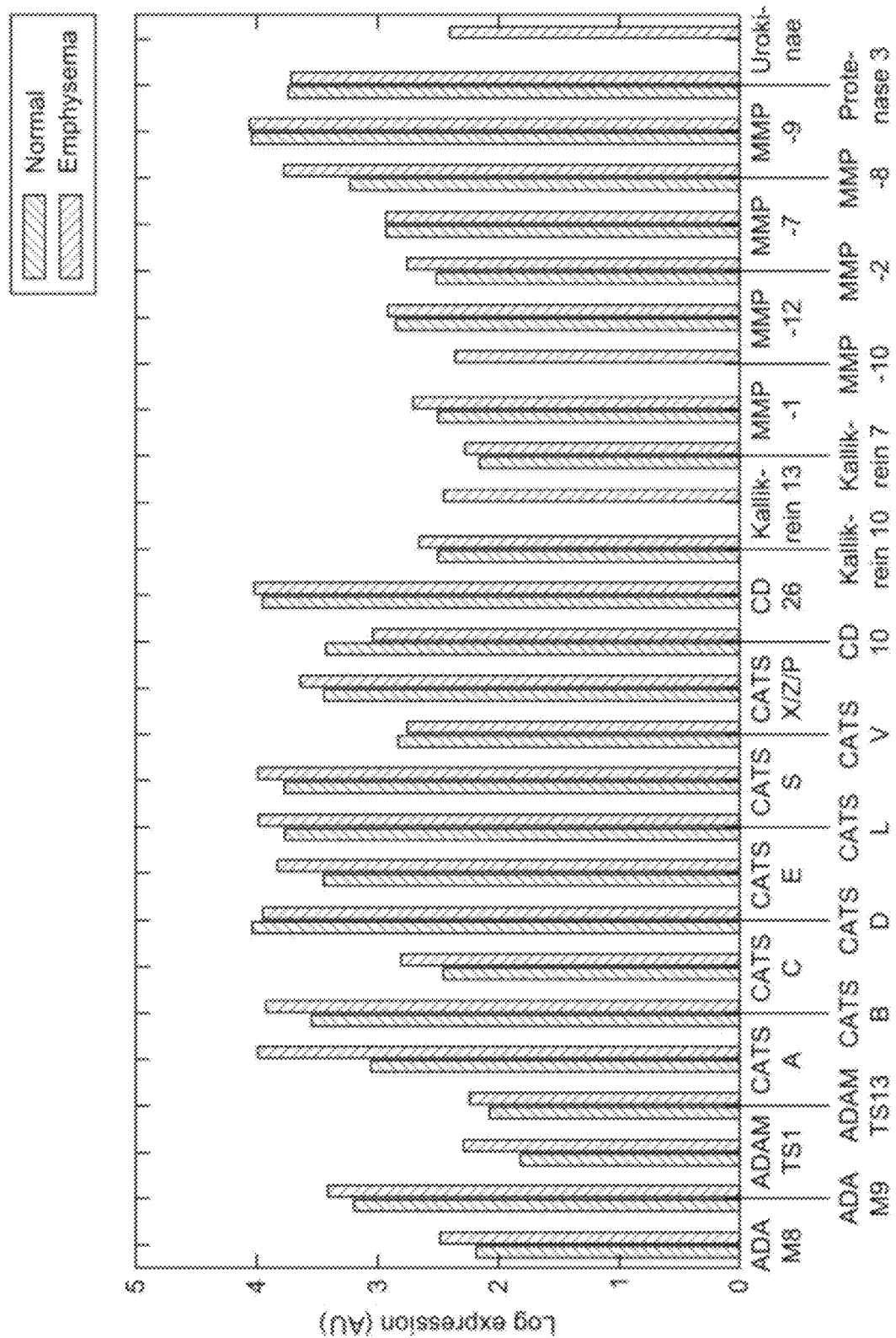
Figure 20C:
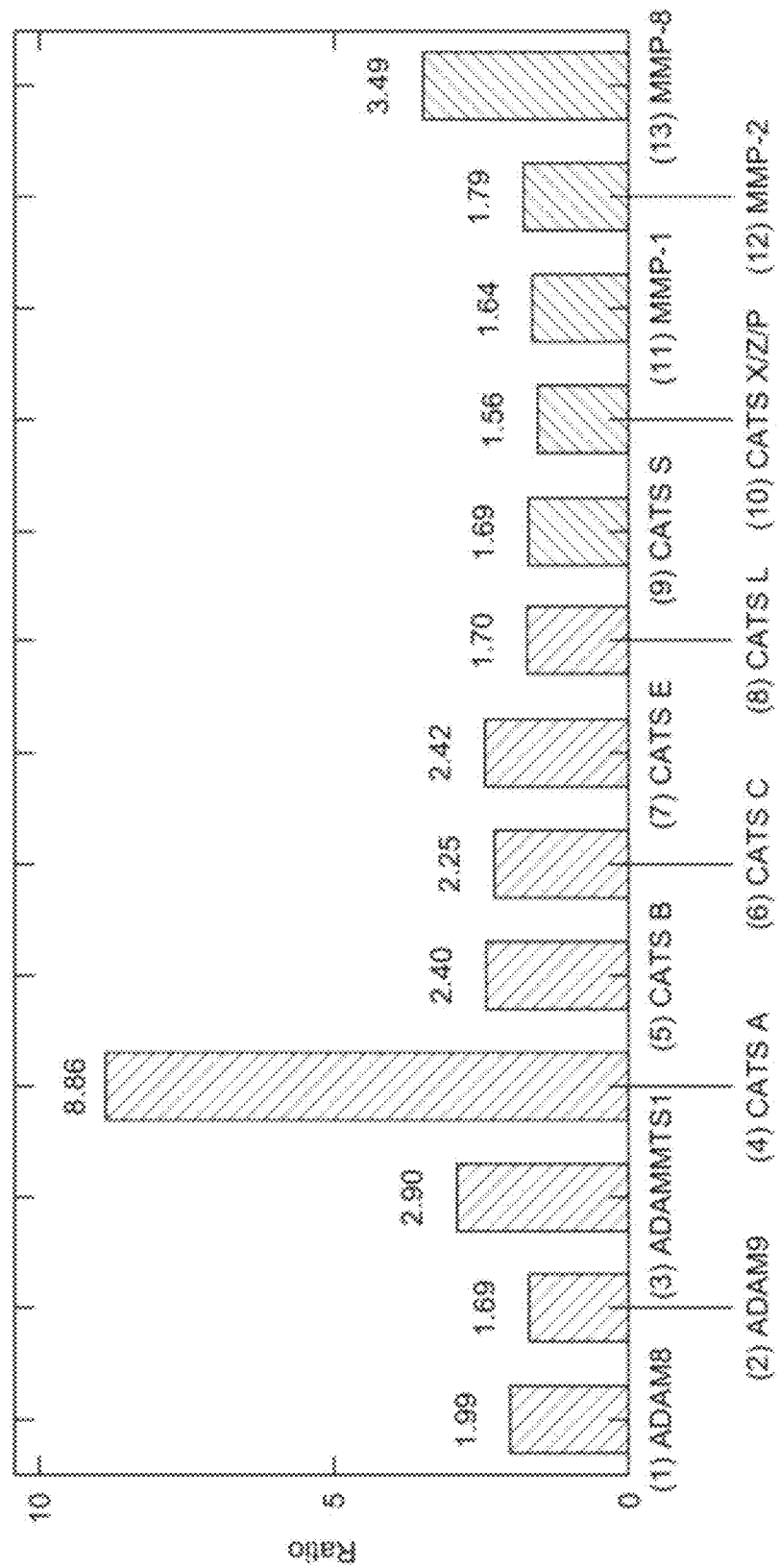
Figure 34:
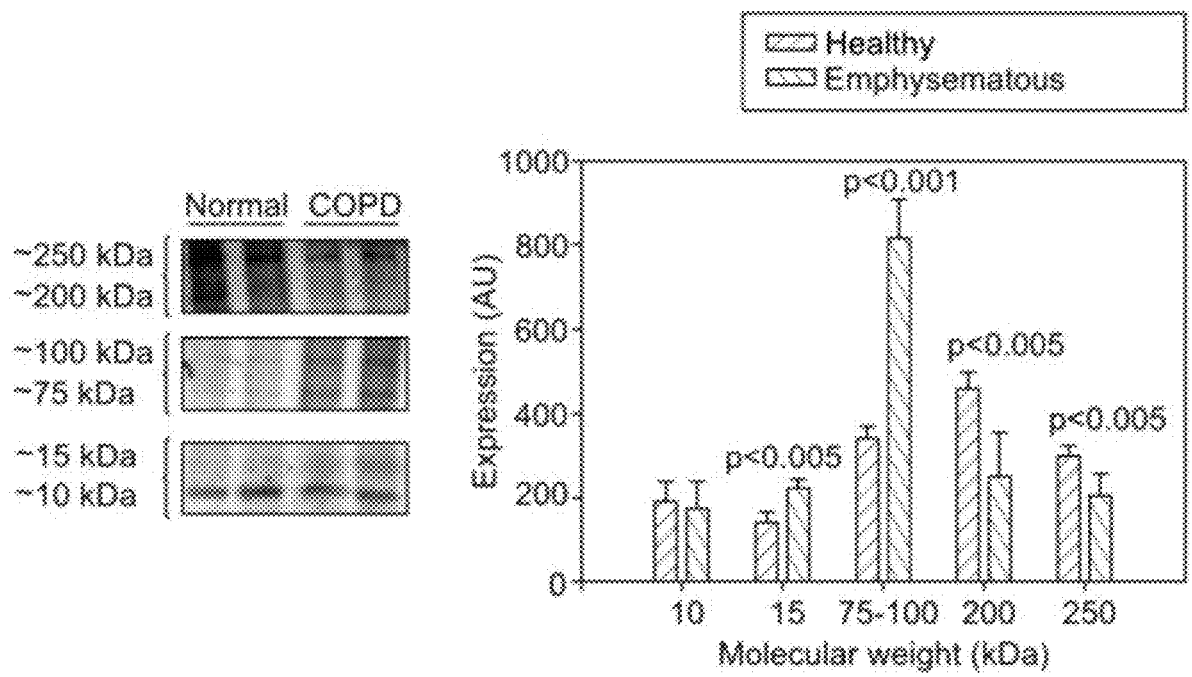
FIG. 34 shows silver staining of hPCLS. Molecular weight distributions of two representative bands of silver-stained gels from homogenized normal and emphysematous hPCLSs (left) and the corresponding statistical analysis (right; n=4 each).
Figure 35A:
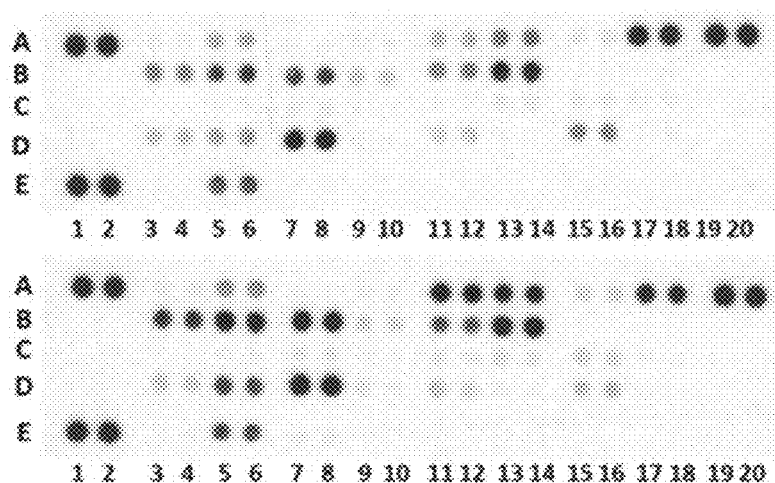

To better understand what drives stiffness decline in emphysema, the inventors first carried out protein profiling of the molecular weight distribution in the healthy and emphysematous hPCLSs by silver staining (FIG. 34). Except for the lowest molecular weight range (~10 kDa), substantial differences were found between the healthy and emphysematous tissues with higher levels of protein species in the 200-250 kDa range and lower levels between 75 and 100 kDa in normal lung. It is noteworthy that soluble collagen is expressed at ~75 kDa. These differences were then further analyzed using a proteome profiler array for 35 human proteases, which screens for a wide spectrum of enzymes. The raw arrays for both the healthy and emphysematous subjects and the corresponding protein amounts are shown in FIGS. 20A and 20B, respectively. The description of the full array is given in FIG. 35A. Many of the enzymes were significantly different between the healthy and emphysematous tissues. The full identification of the dots is given in FIG. 35B. Notably, 3 enzymes, Kallikrein 13, MMP-10 and Urokinase, were only found in the emphysematous hPCLS. Next, the inventors identified 13 enzymes (not including the above 3 enzymes) with amounts at least 1.5 times higher in the emphysematous than the healthy hPCLS (FIG. 20C). These enzyme expressions were associated with more inflammatory cells and identifiable sites of rupture in the emphysematous hPCLS.

To test whether the approach can detect stiffness changes induced by an agent, the inventors tested 2 mouse PCLS (mPCLS) samples acquired from a healthy subject before and after digestion that was induced by bacterial collagenase. After the digestion, the stiffness of healthy mPCLSs was reduced from 5.2 kPa (median) to 2.5 kPa (FIG. 40), which was approximately half of that of the healthy mPCLS (one-tailed t-test, p=0.03).

Discussion

The inventors have introduced a novel approach to measure the stiffness of soft biological tissues and demonstrated that stiffness can be precisely estimated by applying equibiaxial mechanical stretch and tracking bead displacement at the membrane-sample interface. A key advantage of the approach is that it does not need a force sensor. This approach can be used to measure the stiffness of any soft material that can be adhered to the top surface of the membrane-gel system. Indeed, the inventors utilized agarose of different stiffnesses to validate the approach (FIG. 17E). As primary tissue sample, the inventors utilized the PCLS preparation which contains hundreds of alveoli and permits direct visualization of cellular and ECM changes in the native lung tissue (16, 22-24). The PCLS has several practical advantages such as storage via cryopreservation (16, 25), measurement of traction forces (26), widespread applicability to nearly every species including human, and suitability for high-resolution imaging as well as pharmacological and mechanical manipulations including responses to mechanical stretch (27-30), and neural stimulation (31, 32). Comparing the stiffness of hPCLS from healthy and emphysematous subjects showed that tissue degradation leads to loss of function (FIG. 18J).

Figure 37B:
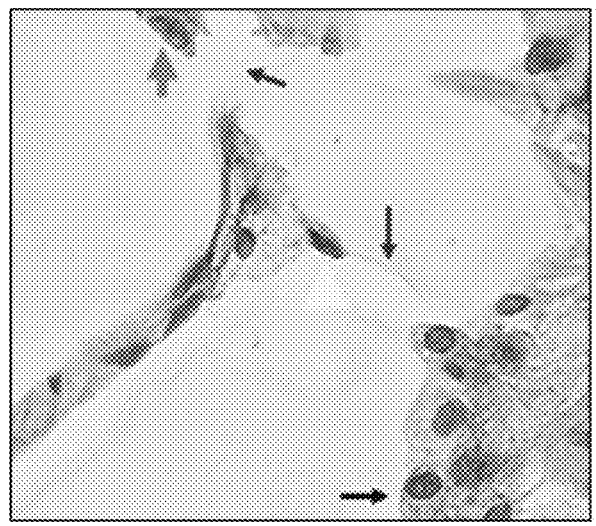
FIGS. 37A and 37B show cell distribution and rupture sites.
Figure 37A:
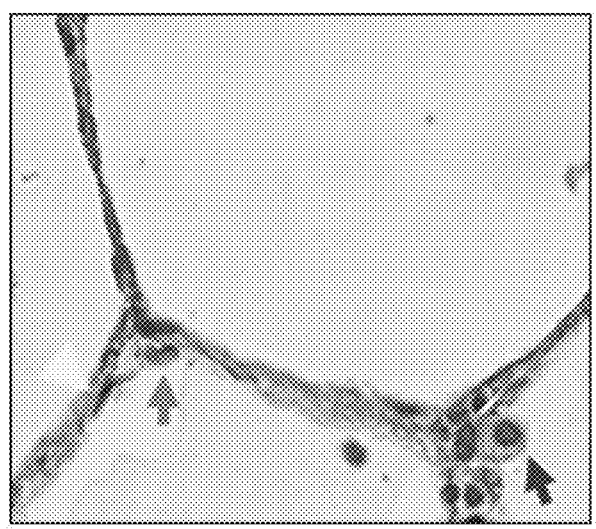
Figure 38C:
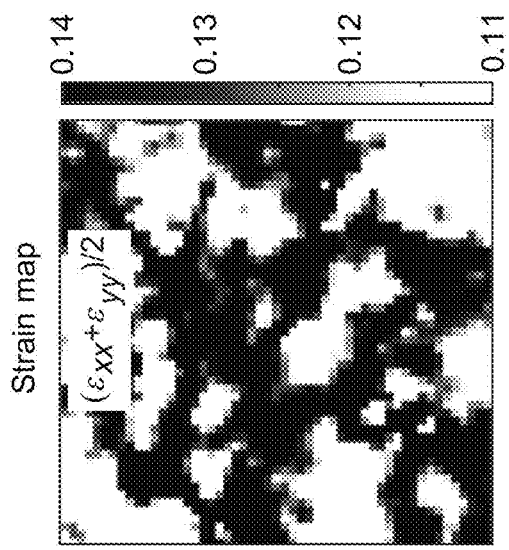
FIGS. 38A-38E show imaging of a mPCLS through phase contrast and fluorescence channels confirms the adhesion of the mPCLS to the membrane composite.
Figure 38E:
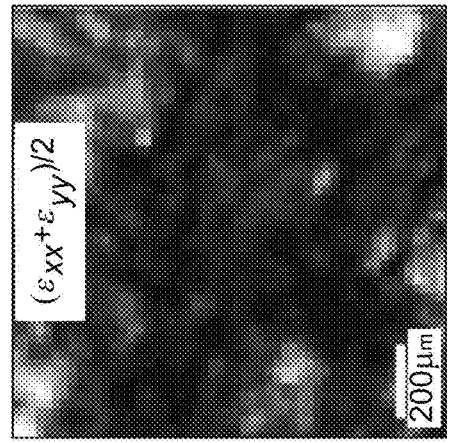
Figure 38B:
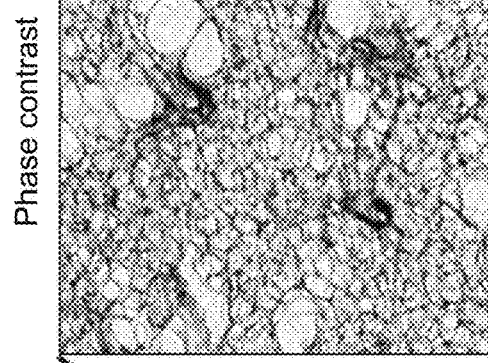
Figure 38D:
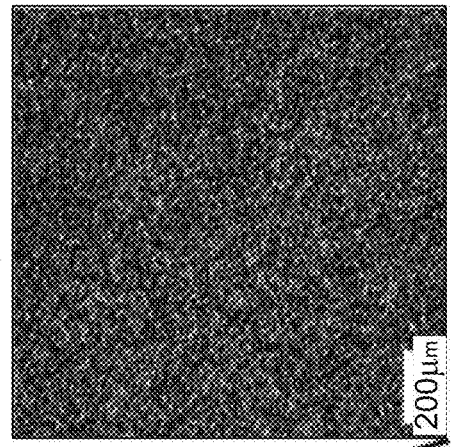
Figure 38A:
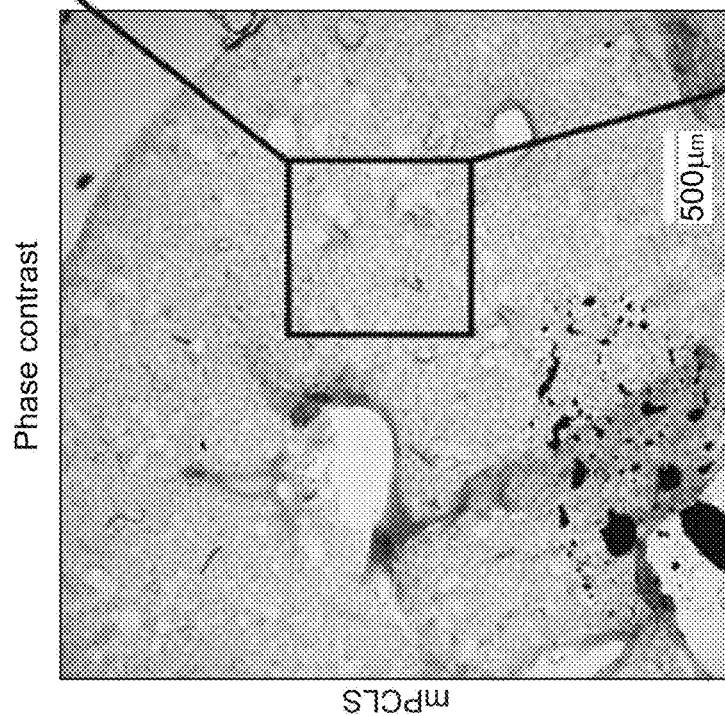

The changes in macroscopic stiffness (FIG. 18J) together with the fluorescent (FIGS. 18F and 18I) and histologic images (FIG. 32A) provide a basis for assessing the loss of tissue function at the microscale. A network analysis of tissue structure and mechanics together with a microscale image analysis allowed us, for the first time, to quantify in the emphysematous hPCLS the partitioning of the loss of function at the macroscale between two sources: 1) structural alterations related to septal wall rupture (FIGS. 37A and 37B), and 2) reduced septal wall stiffness due to cellular remodeling. The results indicated that in addition to airspace enlargement, weakened septal walls substantially contribute to the decrease of macroscopic tissue level stiffness (FIG. 19E). However, these processes are not completely independent. Alveolar wall rupture—which can occur due to the mechanical forces of normal breathing in emphysema (33)—requires that inflammation-related (34) and enzyme-induced (3) remodeling of the septal wall lowers the failure stress of the collagen, elastin and the entire alveolar wall (35). Indeed, the inventors observed that rupture was associated with local sites where inflammatory cells were also found (FIGS. 37A and 37B).

The molecular level remodeling of the ECM of the septal wall is associated with an upregulation of a wide spectrum of enzymes (FIG. 20B), a manifestation of biological complexity. Most of the enzymes that exhibited an expression at least 50% higher in emphysema such as ADAM8 (36), ADAMS (37), the cathepsins including B (38), E (39), L (40) and S (41) as well as all the MMPs (42-44) have been implicated in emphysema. While there seems to be no single biochemical signaling pathway that may account for their specific regulation, these enzymes participate in downstream processes, and many have the ability to cleave ECM molecules. This would indicate that enzyme activities eventually converge toward weakening of the walls with the inescapable end-result of mechanical force-induced rupture. These processes lead to deterioration of the normal structure and function of the lung parenchyma that is reflected in airspace enlargement and multiscale reduction in stiffness.

In conclusion, the inventors have introduced a multiscale approach to measure lung tissue stiffness from the scale of many alveoli governing gas exchange to the scale of single septal walls where pathobiology drives disease progression. Using this approach, the inventors have, for the first time, revealed a mechanistic link between macroscopic lung softening, microscopic structural deterioration, and loss of function in the human emphysematous lung parenchyma.

Example 2

Materials and Methods
  Numerical Computation
  The computational foundation of the concept to measure stiffness was established by generating a two-dimensional axisymmetric finite element (FE) model using the COMSOL Multiphysics® (Version 4.3, COMSOL Inc.) software package. The inventors first modeled the geometry of the device in which a composite membrane-sample system was indented by a hollow indenter (FIG. 26A). The inventors then modeled a simplified geometry in which a composite membrane-sample system was radially stretched (FIG. 26B) and confirmed that the strain profiles from FE models with and without a hollow indenter were nearly identical far beyond the sample region (FIG. 26C). Furthermore, $\varepsilon_{rr}=\varepsilon_{\theta\theta}$ and both strains were nearly constant within the sample region up to ~3 mm of radial position (FIG. 17B). Thus, a composite of a Nusil® layer and a silicone membrane was modeled as a single layer with an apparent composite modulus that was measured using the uniaxial stretcher device (see below), a thickness that was measured after assembly in the rim (Young's modulus=526 kPa, thickness=140 µm) and Poisson's ratio (ν) of 0.45. The sample was modeled as a layer with a diameter of 9 mm, Poisson's ratio (ν) of 0.45, and various thicknesses (100 to 600 µm) and Young's moduli (5 to 35 kPa). No slip between the sample and the composite membrane was allowed (see 'Adhesion of A Sample to the Membrane Composite'). For each simulation with a certain thickness and modulus of the sample, radial strain at the center of the interface between the sample and the composite membrane was computed as an output for the sample. To test the effect of sample shape and alignment on strain measurements, the inventors also performed 3D FE modeling (FIGS. 27A-27I). 3D FE models with three cases 1) a circular sample aligned at the center of a membrane, 2) an elliptical sample aligned at the center of a membrane and 3) a circular sample aligned at 2 mm off from the center of the membrane, confirmed that the measured average strain $(\varepsilon_{xx}+\varepsilon_{yy})/2$ was not sensitive to sample shape or sample alignment relative to a membrane. All simulations were performed using a linear solver, MUMPS (Multifrontal Massively Parallel sparse direct Solver, COMSOL Multiphysics®) with the non-linear geometry option applied.

Preparation of a Composite Membrane
  The composite membrane (FIG. 2) consists of: 1) a silicone membrane (Specialty Manufacturing, Inc., Saginaw, MI) at the bottom, 2) 0.5 µm yellow-green beads (F8813, Invitrogen), 3) a soft PDMS elastomeric gel layer (45) (NuSil-8100; Silicone Technologies, Carpinteria, CA) (Youngs Modulus=3 kPa, thickness=100 µm) in the middle, and 4) a PDMS layer bearing 1 µm diameter custom-synthesized red fluorescent beads (45, 46) (Young's Modulus=3 kPa, thickness=1 µm) at the top.

Figure 28:
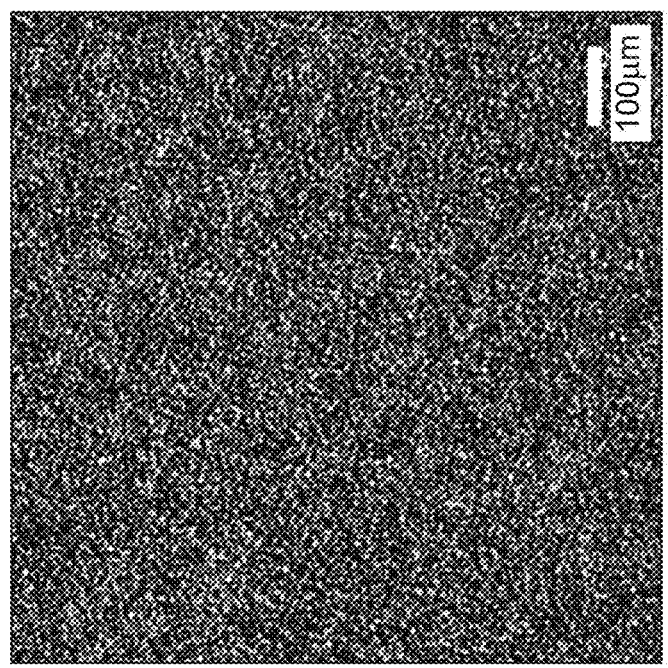
FIG. 28 shows example image of fluorescent beads embedded on the surface of the gel-membrane composite.
Figure 27I:
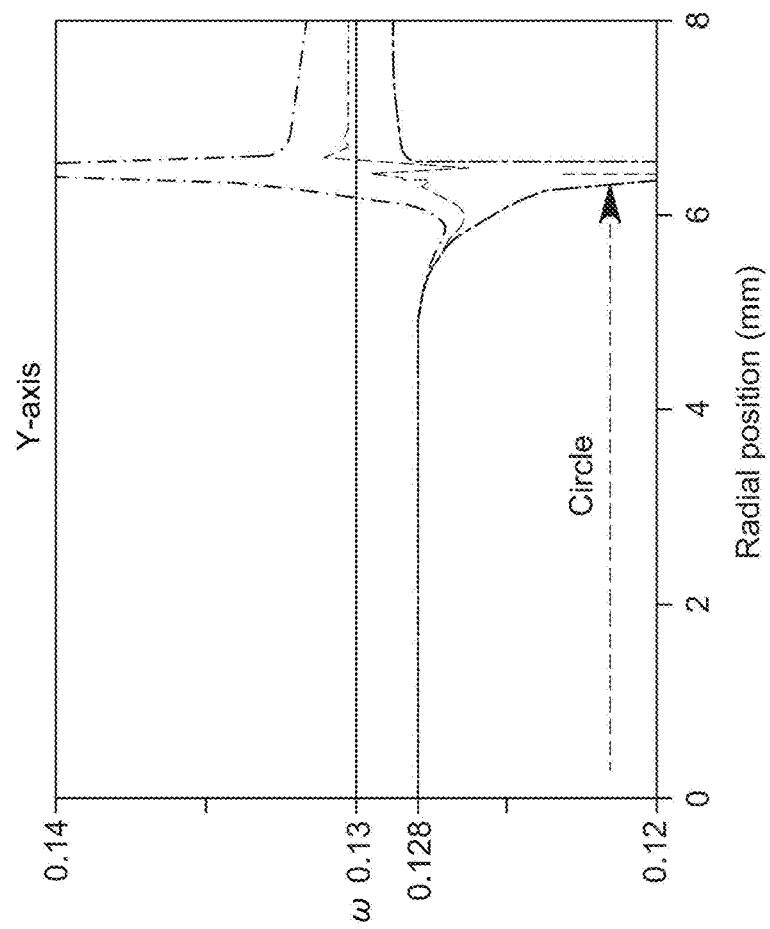
Figure 31B:
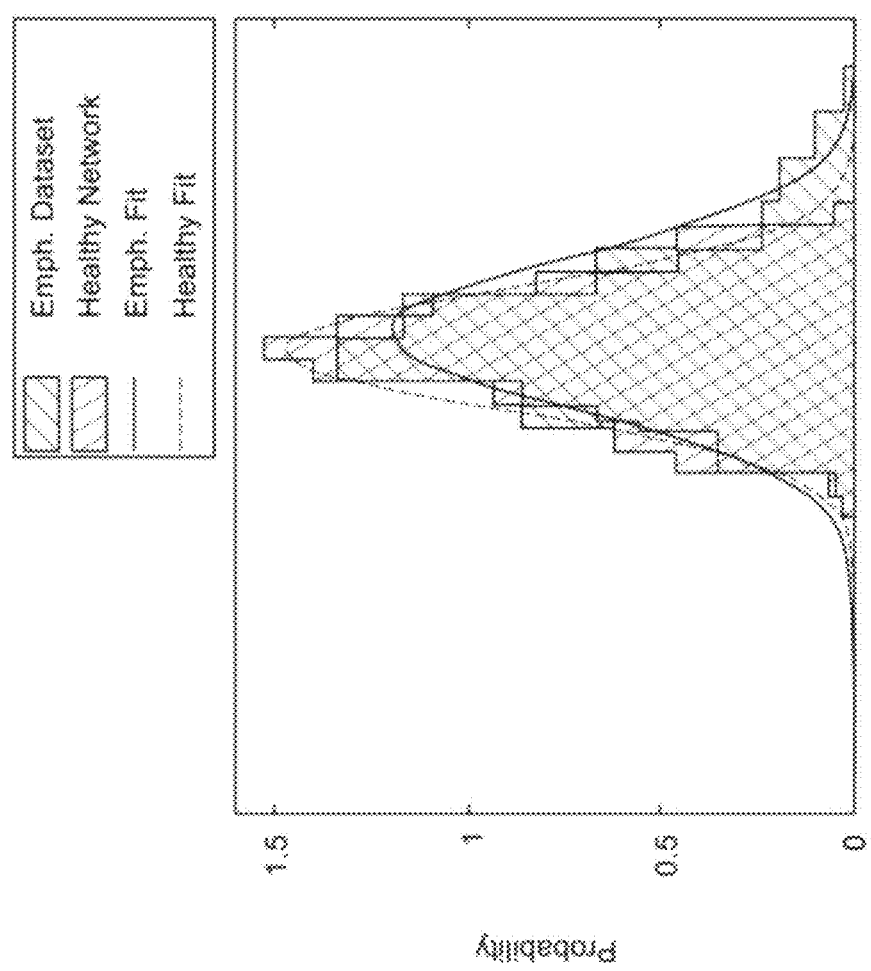
FIGS. 31A-31D show example of PDF matching in networks.
Figure 31A:
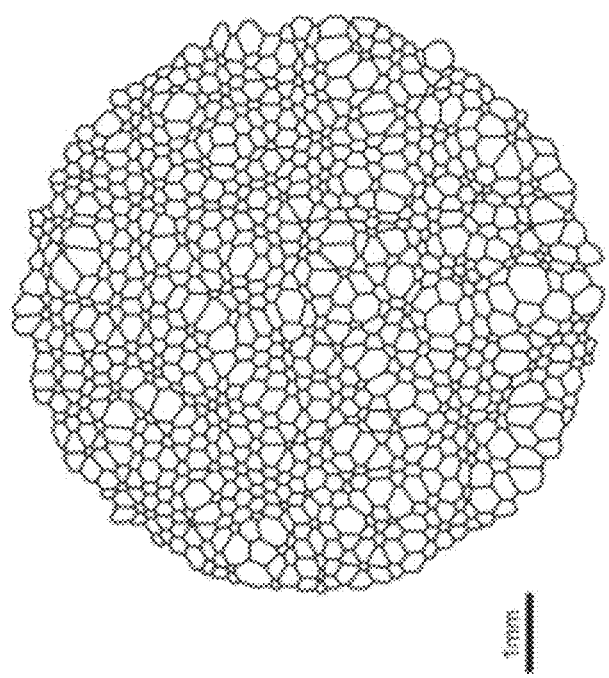
Figure 31C:
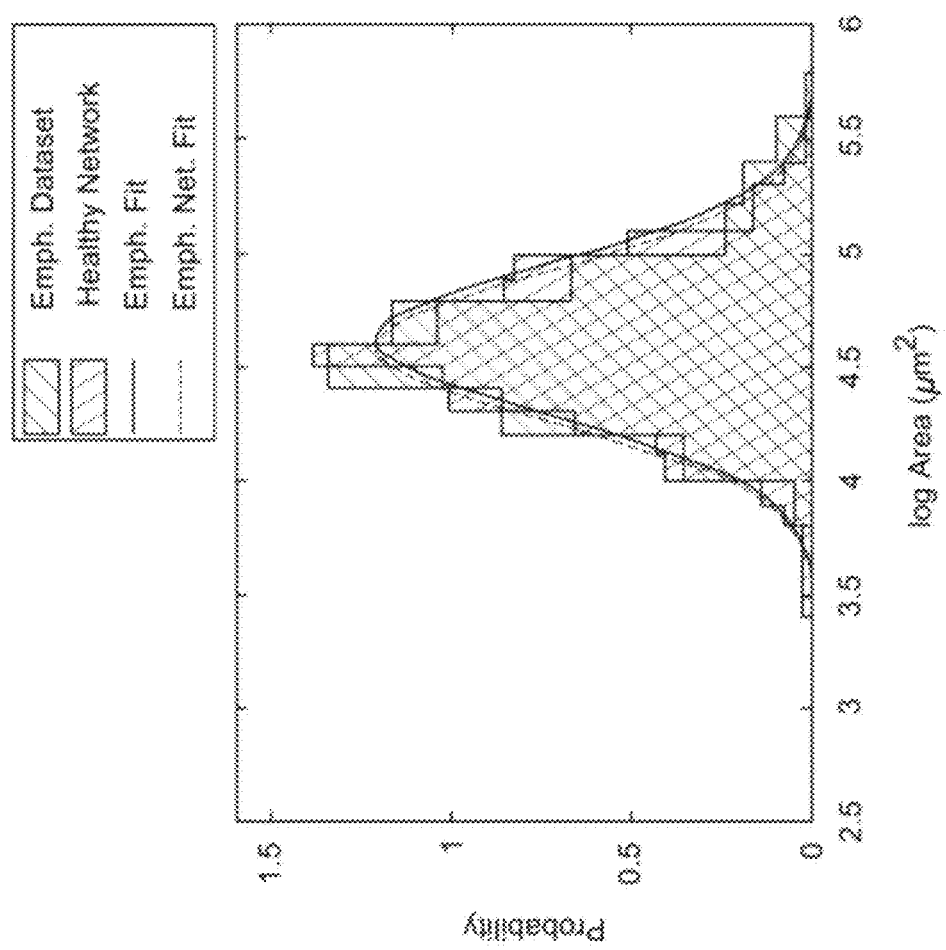
Figure 31D:
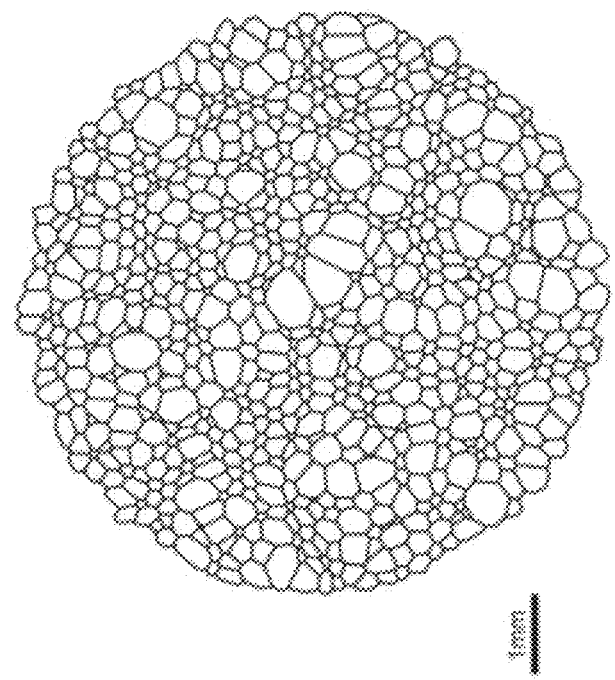
Figure 32D:
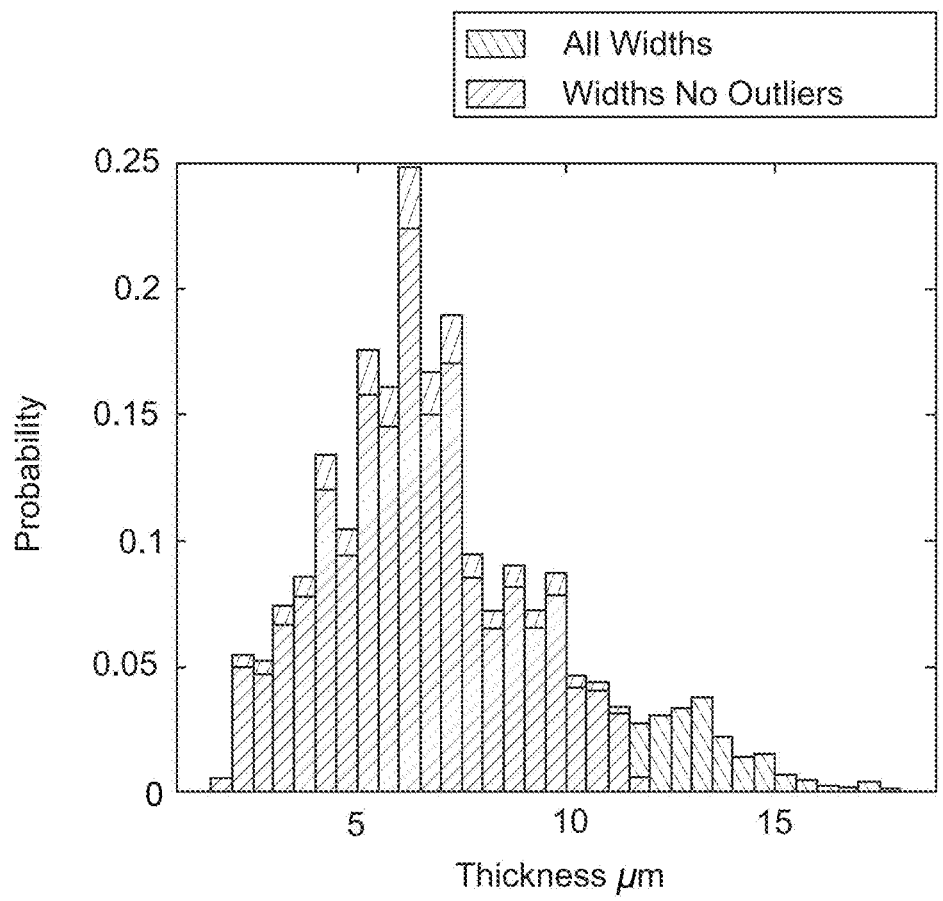
Figure 33B:
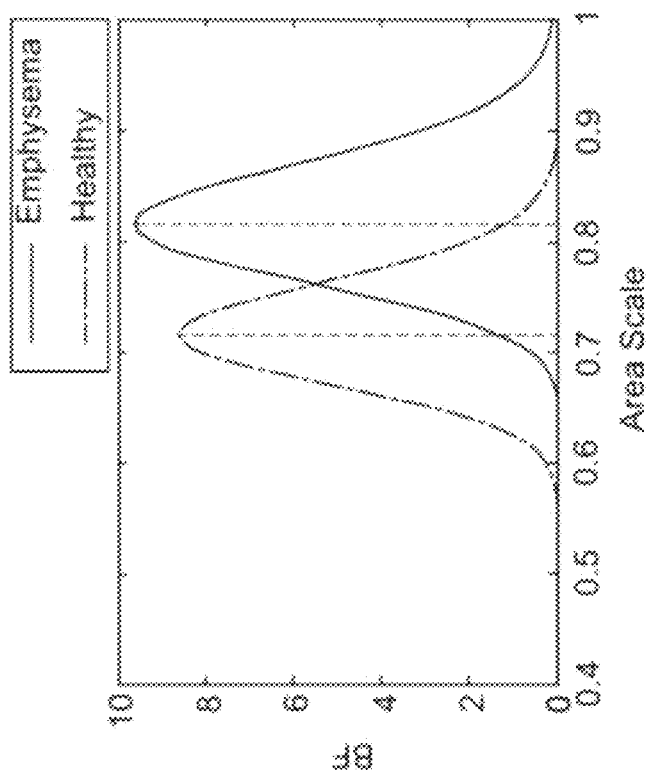
FIGS. 33A-33F show Bayesian analysis of tissue shrinkage.
Figure 33A:
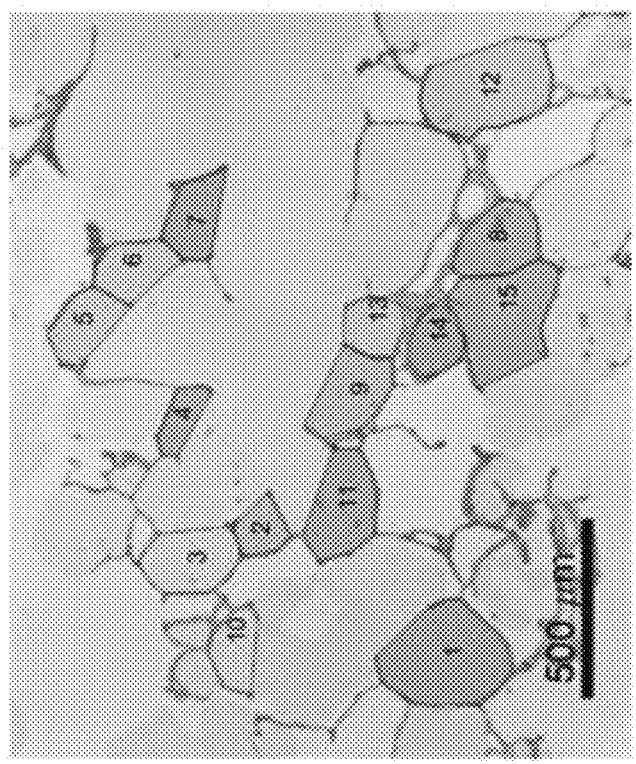
Figure 33D:
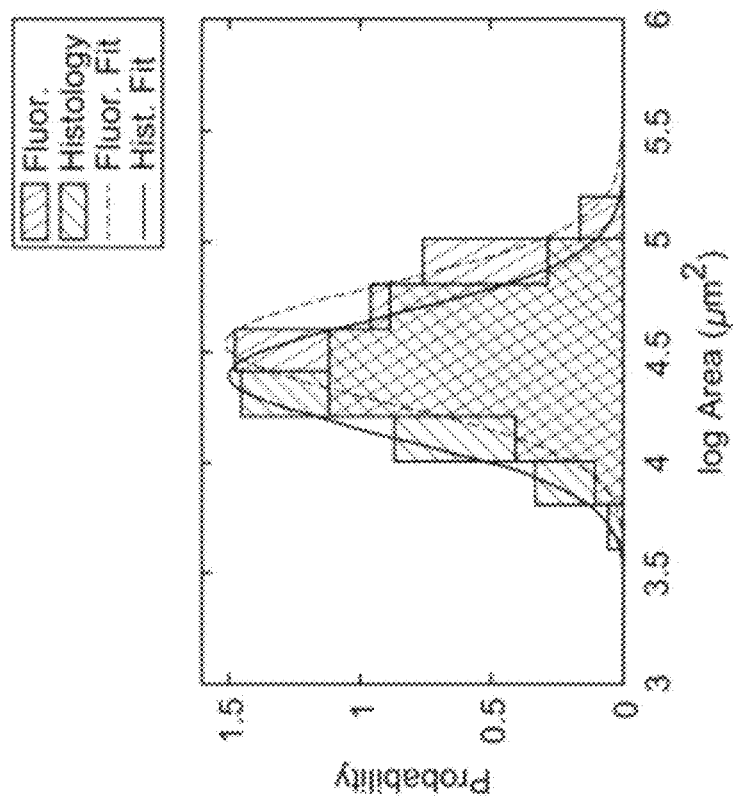
Figure 33C:
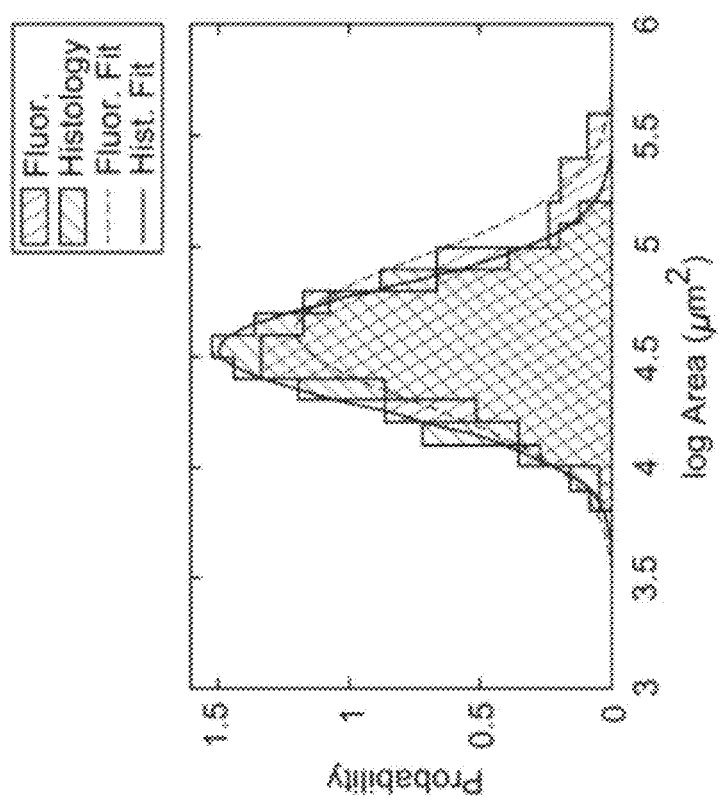
Figure 33F:
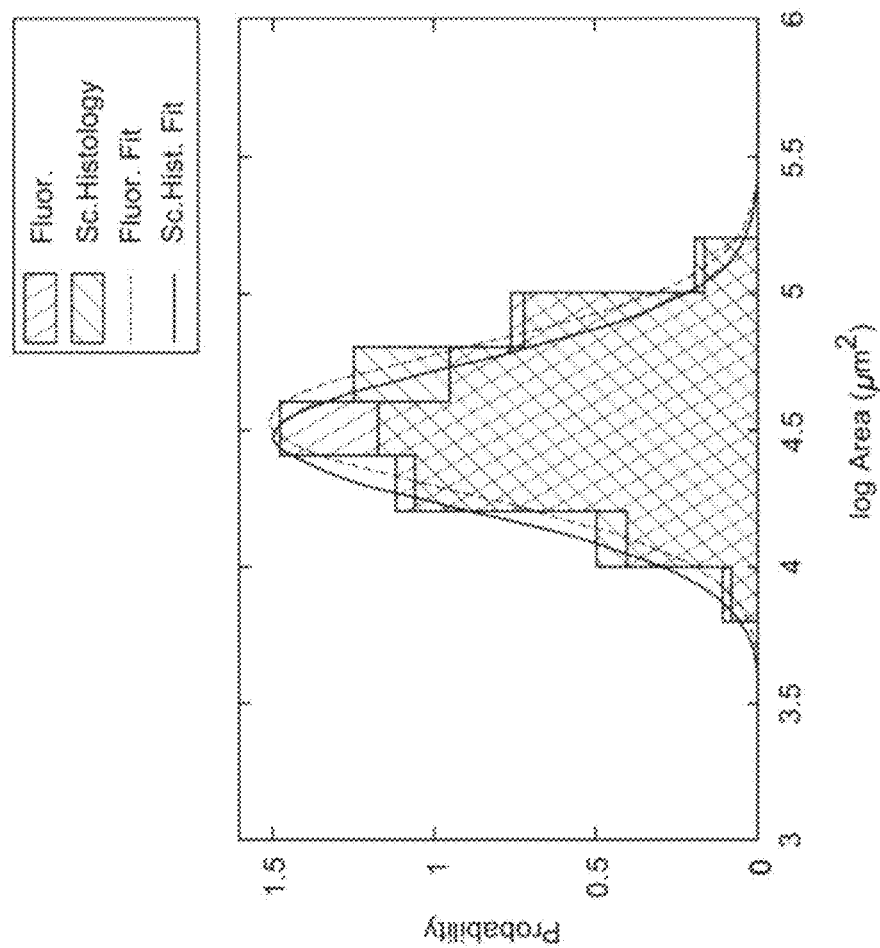
Figure 33E:
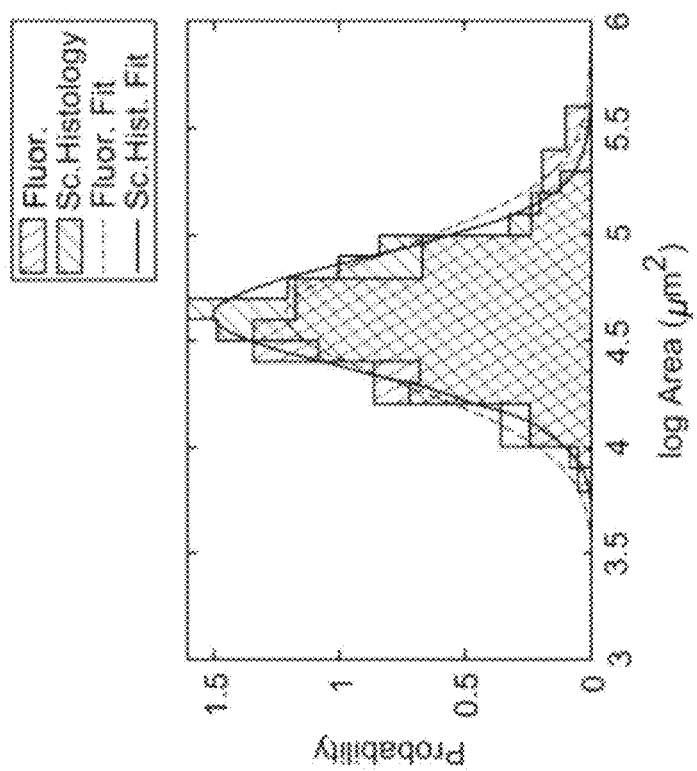

The fabrication proceeds as follows: 1) A section of the silicone membrane is stretched over a glass plate (110 mm×78 mm×1 mm) for support. The edges of the membrane are secured underneath the four corners of the glass plate with tape. Any trapped air pockets are eliminated by gentle rubbing so that the membrane becomes flush against the glass plate. 2) 40 µL of 0.5 µm diameter yellow-green fluorescent beads were dispersed in 10 mL of HBSS and added to the top of the membrane-on-plate. The bead solution is allowed to air dry overnight. The membrane-on-plate is then rinsed with distilled water and air-dried leaving behind a layer of yellow-green beads deposited to the top of the membrane. 3) Next, a gel mixture (NuSil 8100+0.15% Sylgard 184 cross-linking agent) is spin-coated on top of the membrane-on-plate, which is mounted on a spin coater (Laurell WS-650Mz-23, Laurell Technologies, USA). 3-4 ml of uncured gel mixture is added to and spun at 500 rpm/s for 50 sec. The gel/membrane/plate composite is cured at 90° C. for 8 h. This protocol produces a PDMS layer of approximately ~50 µm. This process is then repeated a second time to build up the layer to ~100 µm. 4) To form the top layer bearing fluorescent beads, ~10 ml of the uncured gel mixture is mixed with 800 uL stock solution of custom-made fluorescent beads to create a gel+bead mixture, which is added to the top surface and spin-coated at 2500 rpm/s for 1 min to achieve a thin, ~1 µm bead layer. The bead layer is cured at 90° C. for 8 h. The density of beads is shown in FIG. 28. The PDMS layer is also sticky, enabling the sample surface to be adhered to the composite (see 'Adhesion of A Sample to the Membrane Composite').

Stiffness of the Membrane Composite, and PDMS Gels Determined by Uniaxial Stretch
  The stiffnesses of the composite membrane and porous/non-porous PDMS gels were measured using the uniaxial stretch device following the protocol previously established (47). Briefly, membrane and PDMS samples of 3-9 mm in width and 10-15 mm in length were prepared using a blade. The thickness was measured by finding the distance between fluorescent beads deposited on the top and bottom surfaces of each membrane using an inverted confocal microscope (Olympus FV3000). The sample was assembled with 3D printed clips to avoid slippage. One clip was fixed, and the other was connected to a dual-mode lever arm system (model 300B, Aurora Scientific, Ontario, Canada), which can simultaneously serve both as a displacement generator and a force sensor. The sample was stretched uniaxially with a 0.005 Hz triangle signal generated by a computer. The output force and displacement signals were converted to stress and strain by normalizing with the cross area and initial length, respectively. The slope of a regression between stress and strain between 0-20% strain provided an estimate of the Young's modulus (FIGS. 29A and 29B). The Young's modulus of two composites were measured.

Measurements of Sample Stiffness

The center of the composite membrane was marked by depositing a droplet of 1 μm fluorescent bead solution (AFP-0865-2, Spherotech, IL, USA) on the bottom. First, images of beads embedded on the top surface were acquired near the center of the membrane before and after the composite membrane was stretched through rotation of a fixture, which resulted in a vertical displacement. After placing a sample near the center on the membrane, images were acquired before and after applying the prescribed stretch. Image sets with and without a sample were acquired within ~1.5 mm distance between each other. Each stretched image was acquired within ~2 min after applying the stretch. Stretch experiments were performed ~20 min apart. To compute the global strain $\varepsilon_{rr}^{o}$ or local strain $\varepsilon_{rr}$, strains were averaged over the entire field of view. Stiffness was estimated using Eq (2) and FIG. 17C. Each membrane was repeatedly used until the surface beads deteriorated during multiple sample measurements.

Imaging and Strain Mapping

All imaging experiments were conducted on an inverted confocal microscope (Olympus, FV3000) and a widefield scope (Olympus, ix83). Local displacements were quantified by applying particle imaging velocimetry (PIV) to the stretched image of beads and a reference image (48). The cross-correlation window size was chosen to be 32×32 pixels, and the window overlap was 28 pixels. To improve the accuracy of PIV in determining beads displacements, the stretched image was first shrunk by a factor of 12~13% before performing PIV. After performing PIV on the shrunk image, the image shrinkage factor was further adjusted until the average displacement measured from each PIV analysis became smaller than 3 pixels. Since both the PDMS and the membrane are optically clear, no special considerations were needed to account for a loss of optical clarity in fluorescent bead imaging through the composite membrane from below.

Agarose Preparation

Blocks of agarose samples with 1.5, 2.0 and 2.5% concentration were prepared by adding low-melting-point agarose (A9414, Sigma-Aldrich) to warm Hanks' balanced salt solution (HBSS, Corning Life Sciences, Tewksbury, MA) and cooling. Slices with 12 mm in diameter and 300~600 μm in thickness were prepared using a custom-built aluminum cylinder and a blade.

Porous PDMS

Porous PDMS samples were prepared using previously established protocols (49, 50). In brief, a soft PDMS elastomeric gel solution (see 'Preparation of a Composite Membrane') was mixed with a template solution for pores (EtOH: $H_2O$=2:1) at the final volume ratio of PDMS:template solution=The mixture solution was stirred using a magnetic stirrer at ~300 rpm while kept at ~80° C. for ~20 minutes until pores were trapped. The mixture was then cured in an oven at ~65° C. for 1 hour. As for the control non-porous PDMS, the inventors fabricated PDMS samples in the same manner using the PDMS solution alone. Finally, samples were cut into discs of 6.5 mm in radius and 2~2.5 mm in thickness and measured.

Mouse Lung Slices Preparation

Frozen mouse lung slices (C57BL/6J, 8-10 weeks old, 3 mice) were obtained as a gift from Drs. Xingbin Ai and Yan Bai at Massachusetts General Hospital, Boston. These slices were prepared and frozen as per established procedures (16) approved by the Institutional Animal Care and Use Committee at Massachusetts General Hospital. Briefly, excised mouse lungs were insufflated with 1.5% low-melting-point agarose in Hanks' balanced salt solution (HBSS, Corning Life Sciences, Tewksbury, MA), cooled, and then sectioned into 150 μm thick slices (VF-300; Precisionary Instruments, Greenville, NC). The slices were incubated overnight at 37° C. in 1:1 DMEM/F-12 supplemented with penicillin, streptomycin, kanamycin, and amphotericin B (Invitrogen, Cambridge, MA), transferred to cryovials comprising a cryopreservation medium of 10% DMSO diluted in Dulbecco's modified Eagle/F-12 medium, and stored in liquid nitrogen. On the day of the experiment, the frozen cryovial was thawed rapidly in a 37° C. water bath, and each slice carefully removed and washed once in fresh culture medium prior to use.

Digestion Experiment on Mouse Lung Slices

The tissue was allowed to equilibrate for 5 min at 37° C. in Krebs-Ringer Buffer solution prior to the start of the digestion. Bacterial collagenase (Sigma-Aldrich, Collagenase from *Clostridium* hystolyticum, type IA, crude, 7 mg/100 ul) was added to the bath and kept for 15 min. The tissue was taken out from the bath, washed with fresh HBSS twice, and measured on the device.

Human Lung Slices Preparation for COPD Study

Frozen human slices were purchased from the Institute for In Vitro Sciences (IIVS), Inc., Gaithersburg, MD. Normal (non-diseased) slices were obtained from of a donor (procured through Novabiosis, Durham, NC) who was a 59-year-old female subject without any history of lung related diseases. Emphysematous slices were obtained from of a donor (procured through IIAM, Edison, NJ) who was a 66-year-old male subject with a history of chronic obstructive lung disease (COPD) that is often accompanied emphysema causing parenchymal destruction. Lung slices were prepared and frozen according to established procedures outlined in IIVS's recent publication (51). In brief, the donor lung meeting the desired disease status was received on ice, had overt quality confirmed, and was filled with an isotonic 0.8% low melting point (Molecular Biology Grade) agarose (Bioworld, Dublin, OH; CAS #9012-36-6) in HBSS and DMEM/F12 (1:1 ratio) buffer also containing Antibiotic/Antimycotic. After storage on ice to allow the agarose to gel, the lung lobes are sectioned into ~1.5 cm thick tissue blocks, cored into 8 mm diameter cylinders, and sliced to approximately 500±100 μm mean thickness using a Krumdieck MD4000 slicer prior to cryopreservation.

Human Lung Slices Preparation for IPF Study

Frozen human slices were purchased from the Institute for In Vitro Sciences (IIVS), Inc., Gaithersburg, MD. Normal (non-diseased) slices were obtained from a donor who was a 66-year-old male subject without any history of lung related diseases. IPF slices were obtained from a donor who was a 65-year-old male subject with a history of IPF. Lung slices were prepared and frozen according to established procedures outlined herein above.

Adhesion of a Sample to the Membrane Composite

The agarose sample or PCLS was placed upon the membrane composite, and lightly air-dried with an airflow at a 2 psi (~14 kPa) pressure imposed for 1 min from a tube of 4-mm inner diameter held 3.5 cm above the slice, as previously described (26). This ensured prompt adhesion between the sample surface and the composite. To validate the adhesion of PCLS samples to the membrane composite, the inventors imaged the parenchymal structure of a mPCLS through a phase-contrast channel, and simultaneously, imaged beads through a fluorescence channel on an inverted widefield scope (Olympus, ix83) (FIGS. 38A-38E). The means of average in-plane strain $(\varepsilon_{xx}+\varepsilon_{yy})/2$, computed from structure (FIG. 38C; 13.31%) and beads (FIG. 38E; 13.33%) were identical, confirming that the PCLS and the substrate were stretched without slip.

Autocorrelation Analysis for Spatial Structure

The spatial correlations of the strain maps and the autofluorescent images were estimated by computing the spatial autocorrelation function (20):

$$C(r) = \frac{1}{N \, \text{var}(\bar{q})} \sum_{k,h=1}^{N} \left[ \sum_{|r_i - r_j| = r} \delta \overline{q_i q_j} \right] \quad (4)$$

where q is the signal of interest (strain or autofluorescence), $\delta \overline{q_i}$ is the circularly averaged local departure of q at position $r_i$ from its spatial mean $\bar{q}$, $\text{var}(\bar{q})$ is the variance of q, and $|r_i - r_j| = r$ denotes equality within a uniform bin width of 10 μm, within which there are N points. The characteristic length p of the autocorrelation was calculated as a distance at which C decreased to 0.5. The decay of C(r) indicates the length scale of spatial heterogeneity. For example, if the heterogeneity in an image is correlated over larger distances, C(r) will decay slower toward larger distances, and hence ρ will be larger.

Alveolar Area Distributions

Alveolar areas were used as a metric to quantify structure, and datasets for alveolar areas from both emphysematous and non-emphysematous tissue samples were collected via manual alveolar tracing from fluorescent images. A chi-square test failed to reject the null hypothesis that these distributions were fit by a lognormal distribution at p<0.05. A best-fit lognormal distribution was used to describe the area datasets.

Creation of Network Models

Next, these area distributions were converted into spring networks that match the experimental distributions. To accomplish this, first the alveolar area probability distribution from a healthy tissue was used to create a population of 'input circles' having the same distribution. The circles were arranged randomly in 2D and then densely-packed. Each healthy network had approximately 980 input circles, and the networks as a whole were round and approximately 7 mm in diameter, similar to the hPCLSs. This size was chosen to have a sufficiently large number of alveoli while limiting the amount of time and computation necessary to create the networks. These densely-packed input circles were converted into polygons with edges that are the springs in the network model.

Between sets of 3 circles there is an area that represents a septal junction, and it was found that a node placed at a point within the triangle weighted by the inverse of the areas of the input circles that made that triangle well-maintained the structure of the densely-packed circle diagram, similar to a Voronoi diagram. These nodes are then connected by edges that connect adjacent triangles, and these edges became the springs of the network with each representing a slab of tissue. Once this modified Voronoi diagram was made, the input circles were discarded. These polygons bordered by springs that represent alveoli are referred to as 'cells' (FIGS. 30A-30C).

Once a nascent spring network was created, the parameters of the springs were established as follows. This model utilized linear springs, due to the low strain values, with their spring constants $k_s$ linked to the Young's modulus Y of the septal wall as follows, $$k_s = \frac{Yhw}{Lo} \quad (5)$$

Where h and w are the height and width of the slab and $L_0$ is resting length of the spring. Since the initial state of the spring network is not at equilibrium, the nodes on the border of the network were fixed, and the internal node positions were moved iteratively until the total elastic energy was minimized. Once this was accomplished, an initial spring network was created.

Matching the Network with Sample Structure

The initial networks created as described above had cell area distributions that were slightly larger than the input alveolar area distributions. Hence, the networks were scaled down by the mean ratio of the radii of the experimental data and the cells of the network. However, there still remained some difference between the experimental and network area distributions. Further correction was accomplished by iteratively modifying the springs to change the areas and structure of the network. For this correction, physiological units of the springs are not necessary. Hence, the Ywh term in Eq. 4 was set to 1, and the resting length of the springs was set to 20% the Vononoi diagram edge length of that spring. This provides heterogeneity in spring constant and simulates a prestress such that if a spring is softened, the network will be out of equilibrium.

To match the area distribution of the network to the desired best-fit distribution of the data, a method was developed called 'Probability Density Function Matching' (PDF Matching) (FIGS. 31A-31D). For this process, the area distribution of cells in the network and the desired area distribution of alveolar areas in the samples were discretized and normalized, and the sample PDF was subtracted from the network PDF. Where the greatest difference between the two distributions occurred, a random cell from the network from that discretized bin was selected. A random spring from that cell was elongated by 20%, the corresponding stiffness was changed to reflect the spring length using Eq. 4, and then the entire spring network was solved for equilibrium. This causes the selected cell to increase in area, and the cells around that cell to decrease in area, effectively flattening the area distribution at that location and reducing the difference between the distributions. This process was repeated iteratively until the coefficient of determination between the input distribution and the network distribution was >0.99, indicating that the two PDFs matched well. Once this threshold was reached, the spring network was deemed statistically equivalent to the healthy hPCLS samples. This provided the healthy network.

A similar PDF matching approach was applied to the healthy network to convert it into an emphysematous network. The emphysematous sample area PDF was subtracted from the healthy network area PDF, and where the greatest difference between the distributions occurred, a random cell from that bin was chosen, and a random spring from that cell was cut. This spring cutting reflects the experimental finding that septal walls rupture in emphysema (33). The cells adjoined by the cut spring were then merged. This was repeated iteratively until the network area distribution matched the emphysematous area distribution. Once the iterations were completed, the network was considered the emphysematous network. This process of converting the healthy network into an emphysematous network was chosen, rather than creating a new emphysematous network from the sample distribution, in part due to being substantially faster, but also so a direct network-to-network analysis of the number of cut springs to convert from a healthy network to an emphysematous network could be obtained. After the healthy and emphysematous networks were created, the resting lengths of the springs were set to their apparent length within the network such that the entire network was at equilibrium. This was done to represent the network at its initial prestress, and to eliminate discrepancies caused between networks during PDF matching. At this stage, the network configuration represents the structure of the tissue in personalized spring network form. From this process two corresponding networks were produced, one healthy and one emphysematous.

Model Parameters

In order for the networks to behave as the tissue they represent, it is necessary to define the mechanical properties of the springs in physiological units. To establish the material properties of the septal springs, the geometry of the alveolar septum was used to determine the stiffness of the springs. For this, Eq.4 was used again; however, the cross-sectional area was determined by the height of the hPCLS sample and the mean width of the alveolar septal walls. Although the height terms cancel out, they were included for clarity.

To estimate the width of the alveolar walls, histological images were taken of the tissue after fixation. These images were skeletonized such that a center-line for the walls was created, and then the distance from this centerline to the edge of the tissue was measured for each pixel in the skeleton (FIG. 32A-32D), creating a distribution of thicknesses for the network. Non-wall areas were manually removed from the images to prevent over-estimation of the septal wall thicknesses. To perform this analysis, based on the outline of IPSDK SMART Segmentation Machine Learning algorithm (Reactiv'IP, France), the inventors developed their own algorithm in Matlab.

The effect of tissue fixation on wall thickness was evaluated by comparing the alveolar areas between fluorescent images and histological images. Alveolar area distributions from the histological images were collected through manual tracing. Although the areas from the histological images also fit a lognormal distribution, the fixation caused the tissue to shrink. Based on conservation of mass, this would cause the walls to thicken. To correct for this, a Bayesian analysis was used to compare a scaled version of the area distribution from fluorescent images to the histological area distribution. The scaling multiplier that maximized the Bayes factor, the ratio of the probability of the null hypothesis to that of the alternative hypothesis (FIGS. 33A-33F), was used to calculate the linear strain on the septal walls due to sample shrinkage. The corresponding transverse strain was determined using a Poisson's ratio of 0.5 for the wall tissue, which was used to correct the wall thickness due to fixation.

Calculating the Network Modulus

Once the networks were created and the physiological units of the springs were defined, the networks were mechanically stretched in silico to determine their mechanical properties as follows. The total strain energy $E_{net}$ of the network is given by, $$E_{net} = \frac{1}{2} Y_{net} \epsilon^2 V_{net} \quad (6)$$

where $Y_{net}$ is the Young's modulus of the network, E is the linear radial strain on the network, and $V_{net}$ is the initial volume, defined by the area of the network multiplied by h, the sample thickness. Thus, $Y_{net}$ can be obtained by taking the second derivative of the strain energy density. The strain energy can also be calculated by summing the energy of all the linear springs within the network, using the following relation $$E_{net} = \sum_{i=1}^{n} \frac{1}{2} k_i \Delta x_i^2 \quad (7)$$

where n is the number of springs in the network, $k_i$ is the spring constant of spring i, calculated with Eq. 5, and $\Delta x_i$ is the extension of spring i. To find this relation between energy and strain, the network was stretched equi-biaxially to a set of strains up to 0.05, the network was solved at each strain, and the strain energy was calculated. The resulting energy-strain plot was fit with a second-order equation. The second derivative of this equation divided by the sample volume was then used as an estimate of the Young's modulus of the whole network.

With a known input wall modulus and a measured output network modulus for a given network configuration, it is possible to find the relation between the two moduli. Interestingly, the ratio of the input modulus to the output modulus was constant for all input moduli. This means that once the relation between the input wall modulus and the output network modulus is known, the measured Young's modulus from the hPCLS samples can be used to back-calculate the corresponding Young's modulus of the alveolar septal wall of that sample. For this reason, the Young's modulus of all the springs was set to 1, so the ratio of input septal modulus and output network modulus could be calculated directly.

Hematoxylin and Eosin Staining hPCLS (normal n=6, and emphysematous n=4) were fixed in neutral buffered formalin. 7 µm paraffin embedded sections were processed for routine histological analyses using H&E staining accordingly to the manufacturer's instructions (Hematoxylin and Eosin Stain Kit, Vector Laboratories).

Protein Profiling by Silver Staining hPCLS (normal n=6, and COPD n=4) were homogenized in the presence of protease inhibitors (Thermo Scientific™ Halt™ Protease and Phosphatase Inhibitor Cocktail, ThermoFisher Scientific). BCA protein assay (BioRad) was used for measuring total protein concentration. Equal amounts of protein (~6 µg) were separated by PAGE and gels were silver stained by Silver Stain Plus kit (BioRad).

Enzyme Profiling

Figure 36C:
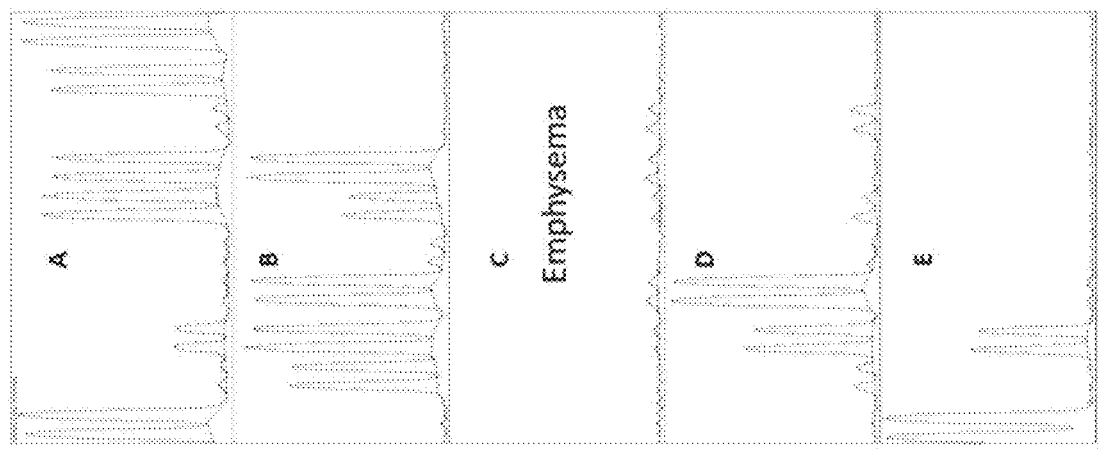
FIGS. 36A-36C show intensity profiles on protein array.
Figure 36B:
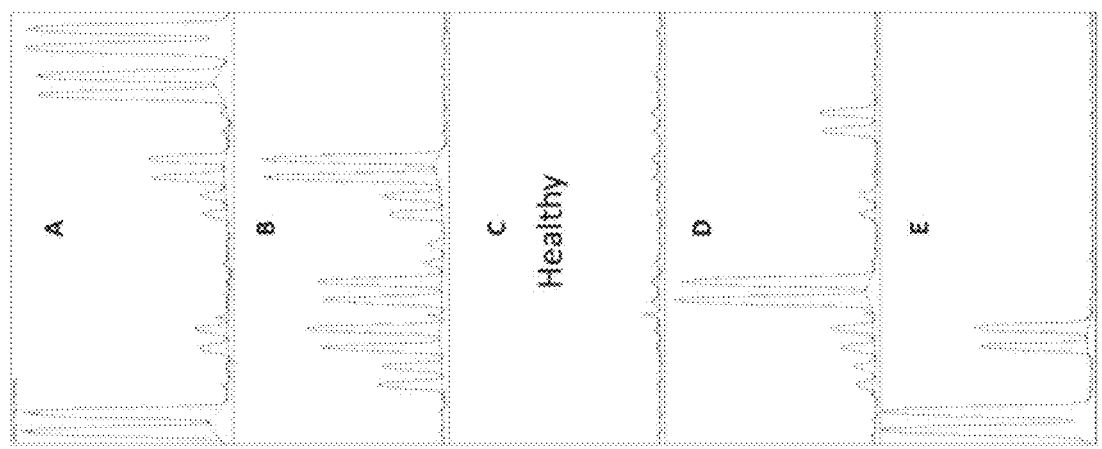
Figure 36A:
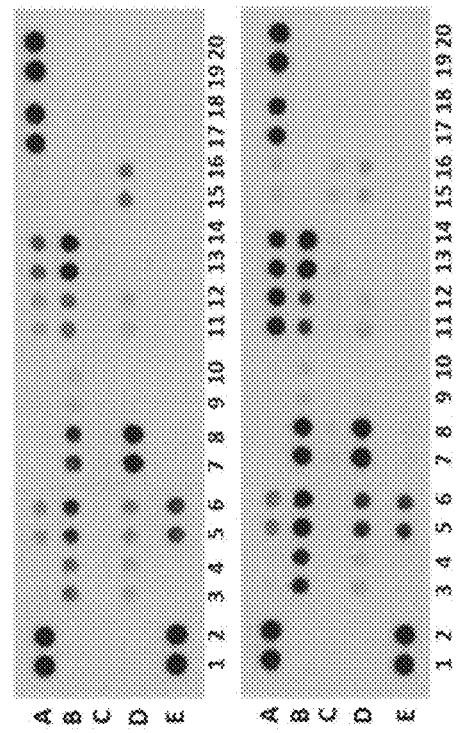

Proteome profiler array was performed using the Human Protease Array Kit (R&D Systems, Inc) accordingly to the manufacturer's instructions. Samples were homogenized (normal n=6, and emphysematous n=4) and after the BCA protein assay (BioRad). Equal amounts (150 µg) of total protein were used for each array membrane containing 35 enzymes. The array dot containing films were scanned and analyzed in ImageJ using the "gels" plugin. The details of the intensity profiles are given in FIGS. 36A-36C.

Statistical Analysis

The healthy and emphysematous hPCLS stiffness values were compared using unpaired Student's 1-way t-test because stiffness was expected to be smaller in emphysema. These analyses were carried out in SigmaPlot (Palo Alto, CA, USA). Significance was accepted for p<0.05. Distributions and lognormal fits were done in Matlab R2021a (MathWorks, MA, USA). Bayesian t-test were done in JASP 0.16 (University of Amsterdam). Posterior distributions were calculated in Matlab using a custom code that assumed unknown mean and variance in the form of a two-parameter gamma-normal distribution and a normal distribution for the likelihood function. To avoid bias, nearly uniform prior distributions were used in the calculations.

What is claimed is:

1. A system for determining a stretch condition of a biological tissue, the system comprising:
    a free-standing composite layer configured to receive a tissue sample of the biological tissue, the free-standing composite layer having a first surface, a second surface that is opposing to the first surface, and two opposing ends, the free-standing composite layer including
        a flexible membrane extending between the two opposing ends,
        a plurality of fiduciary markers interspersed with the flexible membrane, and
        an adhesive area extending at least a portion of the first surface, the adhesive area configured to receive with a no-slip interface the tissue sample; and
    a stretching device including
        an indenter having a plurality of inner points configured to contact the second surface of the free-standing composite layer, and
        a rim aligned with the indenter along a central axis, the rim having a plurality of outer points configured to contact the first surface near the two opposing ends of the free-standing composite layer, the plurality of outer points being farther from the central axis than the plurality of inner points;
    wherein at least one of the indenters and the rim is movable to cause an uniform equibiaxial mechanical stretch of the free-standing composite layer and the tissue sample.

2. The system of claim 1, wherein the plurality of fiduciary markers are interspersed on or within the flexible membrane.

3. The system of claim 1, wherein the flexible membrane is a first layer of the free-standing composite layer, the free-standing composite layer further including a second layer overlaying in a non-slip interface with the first layer, the plurality of fiduciary markers being embedded in the second layer.

4. The system of claim 1, wherein the flexible membrane is a first layer of the free-standing composite layer, the free-standing composite layer further including a second layer overlaying in a non-slip interface with the first layer, the adhesive area being part of the second layer.

5. The system of claim 1, wherein the flexible membrane is a first layer of the free-standing composite layer, the free-standing composite layer further including:
    a second layer overlaying in a non-slip interface with the first layer, the plurality of fiduciary markers being embedded in the second layer; and
    a third layer overlaying in a non-slip interface with the second layer, the third layer including the adhesive area.

6. The system of claim 1, wherein at least one of the plurality of fiduciary markers is a fluorescent bead.

7. The system of claim 1, wherein the flexible membrane includes one or more of a silicon material and a polydimethylsiloxane (PDMS) material.

8. The system of claim 1, wherein the indenter has a hollow interior between the plurality of inner points.

9. The system of claim 1, further comprising an inverted microscope configured for imaging the plurality of fiduciary markers, the inverted microscope providing a displaced image of the plurality of fiduciary markers in response to the uniform equibiaxial mechanical stretch.

10. The system of claim 1, wherein the displaced image is a displacement map of the plurality of fiduciary markers.

11. The system of claim 1, wherein the rim is configured to travel vertically towards the indenter.

12. The system of claim 1, wherein the stretching device includes a well within which the rim and indenter are both mounted.

13. The system of claim 1, wherein the rim is positioned above the indenter.

14. The system of claim 13, wherein each of the well, the rim, and the indenter have a circular shape.

15. The system of claim 13, wherein the rim and the indenter are aligned within the rim along a central axis.

16. The system of claim 13, wherein each of the well, the rim, and the indenter have a hollow interior, the hollow interior being positioned over at least a portion of the plurality of fiduciary markers, the hollow interior providing an imaging path for capturing a displaced image of the plurality of fiduciary markers in response to the uniform equibiaxial mechanical stretch.

17. The system of claim 1, further comprising a controller configured to determine a global radial strain of a substrate layer that is measured when the layer is stretched without a sample via a formula of:

$$\varepsilon_{rr}^{o} = \Delta r_{memb}/r_{memb}^{o} \times 100$$

wherein $\Delta r_{memb}$ denotes the change of the radius, and $r_{memb}^{o}$ is the stress-free radius, and the local radial strain $\varepsilon_{rr}$ that is measured when the substrate and substrate having an adhered sample is stretched, wherein difference between the global radial strain and the local strain is converted to a readout of the stiffness of the sample through a formula:

$$\phi = \frac{\varepsilon_{rr}^{0} - \varepsilon_{rr}}{\varepsilon_{rr}^{0} h} = AE$$

wherein h is the thickness of the sample, A is a constant that is computed through a linear regression, and E is the stiffness of a sample, and
wherein samples are classified as either having increased stiffness, decreased stiffness, or normal parameters.

18. A system for determining a stretch condition of a biological tissue, the system comprising:
    a free-standing composite layer configured to receive a tissue sample of the biological tissue, the free-standing composite layer having a first surface, a second surface that is opposing to the first surface, and two opposing ends, the free-standing composite layer including
        a first layer in the form of a flexible membrane that forms a base of the free-standing composite layer,
        a second layer with a tunable stiffness overlaying in a no-slip interface with the first layer, the second layer including a plurality of fiduciary markers, and a third layer overlaying in a no-slip interface with the second layer, the third layer having an adhesive surface opposing the no-slip interface with the second layer, the adhesive surface being configured to receive with a no-slip interface the tissue sample; and a stretching device including
an indenter having a plurality of inner points configured to contact the second surface of the free-standing composite layer, and
a rim aligned with the indenter along a central axis, the rim having a plurality of outer points configured to contact the first surface near the two opposing ends of the free-standing composite layer, the plurality of outer points being farther from the central axis than the plurality of inner points;

wherein at least one of the indenter and the rim is movable to cause an uniform equibiaxial mechanical stretch of the free-standing composite layer and the tissue sample.

19. A method of classifying a sample, the method comprising
a) applying radial stretch to a substrate and determining a global radial strain of the substrate layer that is measured when the layer is stretched;
b) adhering the sample to the substrate; and
c) applying radial stretch the substrate having an adhered sample and determining a global radial strain of the substrate layer that is measured when the layer is stretched, wherein measuring is done via a formula of:

$\varepsilon_{rr}^{o} = \Delta r_{memb}/r_{memb}^{o} \times 100$ wherein $\Delta r_{memb}$ denotes the change of the radius, and $r_{memb}^{o}$ is the stress-free radius, and the local radial strain $\varepsilon_{rr}$ that is measured when the substrate and substrate having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and
wherein samples are classified as either having increased stiffness, decreased stiffness, or normal parameters.

20. A method of assessing the effect of at least one agent on classification of a sample, the method comprising
a) applying radial stretch to a substrate and determining a global radial strain of the substrate layer that is measured when the layer is stretched;
b) adhering the sample to the substrate;
c) contacting the sample with the at least one agent; and
d) applying radial stretch the substrate having an adhered sample and determining a global radial strain of the substrate layer that is measured when the layer is stretched, wherein measuring is done via a formula of:

$\varepsilon_{rr}^{o} = \Delta r_{memb}/r_{memb}^{o} \times 100$ wherein $\Delta r_{memb}^{o}$ denotes the change of the radius, and $r_{memb}^{o}$ is the stress-free radius, and the local radial strain $\varepsilon_{rr}$ that is measured when the substrate and substrate having an adhered sample is stretched, wherein difference between the global radial strain and the local strain is converted to a readout of the stiffness of the sample through a formula:

$$\phi = \frac{\varepsilon_{rr}^0 - \varepsilon_{rr}}{\varepsilon_{rr}^0 h} = AE$$

wherein h is the thickness of the sample, A is a constant that is computed through a linear regression, and E is the stiffness of a sample, and
wherein samples are classified as either having increased stiffness, decreased stiffness, or normal parameters.

* * * * *